United States Patent
Hall et al.

(10) Patent No.: US 12,333,715 B2
(45) Date of Patent: Jun. 17, 2025

(54) METHOD AND SYSTEM FOR SELECTING EMBRYOS

(71) Applicant: ASTEC CO., Ltd., Fukuoka (JP)

(72) Inventors: Jonathan Michael MacGillivray Hall, Adelaide (AU); Donato Perugini, Adelaide (AU); Michelle Perugini, Adelaide (AU)

(73) Assignee: ASTEC CO., Ltd., Fukuoka (JP)

( * ) Notice: Subject to any disclaimer, the term of this patent is extended or adjusted under 35 U.S.C. 154(b) by 764 days.

(21) Appl. No.: 17/600,739

(22) PCT Filed: Apr. 2, 2020

(86) PCT No.: PCT/AU2020/000027
§ 371 (c)(1),
(2) Date: Oct. 1, 2021

(87) PCT Pub. No.: WO2020/198779
PCT Pub. Date: Oct. 8, 2020

(65) Prior Publication Data
US 2022/0198657 A1  Jun. 23, 2022

(30) Foreign Application Priority Data
Apr. 4, 2019  (AU) .............................. 2019901152

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06V 10/50* (2022.01); *G06V 10/54* (2022.01);
(Continued)

(58) Field of Classification Search
CPC ................... G06T 7/0012; G06T 7/11; G06T 2207/20081; G06T 2207/30044;
(Continued)

(56) References Cited

U.S. PATENT DOCUMENTS 9,984,278 B2   5/2018  Needleman et al.
10,489,904 B2  11/2019 Barnes et al.
(Continued)

FOREIGN PATENT DOCUMENTS

CA   3 068 194 A1    1/2019
CN   104462673 A     3/2015
(Continued)

OTHER PUBLICATIONS

Seundong, Aimee et al., Fetal cardiac activity at 4 weeks after in vitro fertilization predicts successful completion of the first trimester of Pregnancy, Nov. 2008, American Society for Reproductive Medicine, Published by Elsevier Inc., vol. 90 No. 5, pp. 1711-1715 (Year: 2008).*
(Continued)

*Primary Examiner* — Lewis G West
(74) *Attorney, Agent, or Firm* — Suzannah K. Sundby, Esq.; Canady + Lortz LLP

(57) ABSTRACT

An Artificial Intelligence (AI) computational system for generating an embryo viability score from a single image of an embryo to aid selection of an embryo for implantation in an In-Vitro Fertilisation (IVF) procedure is described. The AI model uses a deep learning method applied to images in which the Zona Pellucida region in the image is identified using segmentation, and ground truth labels such as detection of a heartbeat at a six week ultrasound scan.

21 Claims, 21 Drawing Sheets

(51) Int. Cl.
| | |
|---|---|
| *G06V 10/50* | (2022.01) |
| *G06V 10/54* | (2022.01) |
| *G06V 10/82* | (2022.01) |
| *G06V 20/69* | (2022.01) |

(52) U.S. Cl.
CPC ............ *G06V 10/82* (2022.01); *G06V 20/695* (2022.01); *G06T 2207/20081* (2013.01); *G06T 2207/30044* (2013.01)

(58) Field of Classification Search
CPC .... G06T 7/12; G06T 7/136; G06T 7/149; G06T 2200/28; G06T 2207/10016; G06T 2207/10024; G06T 2207/10056; G06T 2207/20061; G06T 2207/20084; G06V 10/50; G06V 10/54; G06V 10/82; G06V 20/695; G06F 18/24133; G06F 17/145; G06N 3/045; G06N 3/08; G06N 20/20; A61B 17/435
See application file for complete search history.

(56) References Cited

U.S. PATENT DOCUMENTS

| | | | | |
|---|---|---|---|---|
| 11,037,030 | B1* | 6/2021 | Kolouri | G01S 13/9027 |
| 11,169,064 | B2* | 11/2021 | Prien | G01N 33/4833 |
| 11,321,831 | B2 | 5/2022 | Shafiee et al. | |
| 11,335,000 | B2 | 5/2022 | Iwata et al. | |
| 11,494,578 | B1* | 11/2022 | Chian | G06T 7/0016 |
| 2003/0088565 | A1 | 5/2003 | Walter et al. | |
| 2007/0179746 | A1 | 8/2007 | Jiang et al. | |
| 2010/0188496 | A1 | 7/2010 | Xie et al. | |
| 2011/0230362 | A1 | 9/2011 | Craig et al. | |
| 2011/0254943 | A1 | 10/2011 | Ozinsky et al. | |
| 2012/0215727 | A1 | 8/2012 | Malik et al. | |
| 2013/0230230 | A1 | 9/2013 | Ajemba et al. | |
| 2014/0017717 | A1 | 1/2014 | Loewke et al. | |
| 2014/0247972 | A1 | 9/2014 | Wang et al. | |
| 2015/0160117 | A1 | 6/2015 | Wong et al. | |
| 2015/0346187 | A1 | 12/2015 | Loewke et al. | |
| 2015/0356461 | A1 | 12/2015 | Vinyals et al. | |
| 2016/0359886 | A1 | 12/2016 | Yadav et al. | |
| 2017/0089820 | A1* | 3/2017 | Wong | C12M 41/48 |
| 2017/0098172 | A1 | 4/2017 | Ellenbogen et al. | |
| 2017/0132528 | A1 | 5/2017 | Aslan et al. | |
| 2018/0039905 | A1 | 2/2018 | Anghel et al. | |
| 2018/0268292 | A1 | 9/2018 | Choi et al. | |
| 2019/0042958 | A1* | 2/2019 | Letterie | G06V 20/698 |
| 2019/0073591 | A1 | 3/2019 | Andoni et al. | |
| 2019/0110753 | A1* | 4/2019 | Zhang | A61B 3/0025 |
| 2019/0110754 | A1* | 4/2019 | Rao | G06N 7/00 |
| 2020/0126233 | A1 | 4/2020 | Shinoda et al. | |
| 2020/0226750 | A1* | 7/2020 | Shafiee | G06T 7/0012 |
| 2020/0311916 | A1* | 10/2020 | Tran | G16H 30/40 |

FOREIGN PATENT DOCUMENTS

| | | |
|---|---|---|
| CN | 109409182 A | 3/2019 |
| WO | 2014/089647 A1 | 6/2014 |
| WO | 2019/042571 A1 | 3/2019 |

OTHER PUBLICATIONS

Anil et al., "Large Scale Distributed Neural Network Training Through Online Distillation," arXiv:1804.03235v1 [cs.LG], Apr. 9, 2018, 12 pages.

Annan et al., "Biochemical Pregnancy During Assisted Conception: A Little Bit Pregnant," *J Clin Med Res* 5(4):269-274, 2013.

Bormann et al., "Performance of a deep learning based neural network in the selection of human blastocytes for implantation," *eLife* 9:e55301, 2020. (14 pages).

Breiman, "Random Forests," *Machine Learning* 45(1):5-32, 2001.

Chen et al., "Does time-lapse imaging have favorable results for embryo incubation and selection compared with conventional methods in clinical in vitro fertilization? A meta-analysis and systematic review of randomized controlled trials," *PLoS One* 12(6):e0178720, 2017. (18 pages).

Gardner et al., "Assessment of Embryo Viability: The Ability to Select a Single Embryo for Transfer—A Review," *Placenta* 24(Supplement B):S5-S12, 2003. (8 pages).

Gardner et al., "Diagnosis of human preimplantation embryo viability," *Hum Reprod Update* 21(6):727-747, 2015.

GBD 2017 Population and Fertility Collaborators, "Population and fertility by age and sex for 195 countries and territories, 1950-2017: a systematic analysis for the Global Burden of Disease Study 2017," *Lancet* 392(10159):1995-2051, 2018.

He et al., "Deep Residual Learning for Image Recognition," *2016 IEEE Conference on Computer Vision and Pattern Recognition (CVPR)*, Institute of Electrical and Electronics Engineers, Las Vegas, NV, Jun. 27-30, 2016, pp. 770-778.

Hearst et al., "Support vector machines," *IEEE Intelligent Systems and their Applications* 13(4):18-28, Jul.-Aug. 1998.

Huang et al., "Densely Connected Convolutional Networks," *2017 IEEE Conference on Computer Vision and Pattern Recognition (CVPR)*, Institute of Electrical and Electronics Engineers, Honolulu, HI, Jul. 21-26, 2017, pp. 2261-2269.

International Search Report and Written Opinion, mailed May 5, 2020, for International Application No. PCT/AU2020/000027, 10 pages.

Khan, "Automated Monitoring of Early Stage Human Embryonic Cells in Time-lapse Microscopy Images," doctoral dissertation, The Australian National University, 2016, 143 pages.

Kheradmand, "Human Embryo Component Detection using Computer Vision," master's thesis, Simon Fraser University, 2017, 89 pages.

Kingma et al., "Adam: A Method for Stochastic Optimization," conference paper, 3rd International Conference for Learning Representations, San Diego, CA, May 7-9, 2015, 15 pages.

Rokach, "Ensemble-based classifiers," *Artif Intell Rev* 33(1):1-39, 2010.

Rumelhart et al., "Learning representations by back-propagating errors," *Nature* 323(6088):533-536, 1986.

Segel et al., "Development of a Decision Tool to Predict Blastocyst Formation," *Fertility & Sterility* 109(3):e49-50, 2018.

Storr et al., "Inter-observer and intra-observer agreement between embryologists during selection of a single Day 5 embryo for transfer: a multicenter study," *Hum Reprod* 32(2):307-314, 2017.

Szegedy et al., "Inception-v4, Inception-ResNet and the Impact of Residual Connections on Learning," in *Proceedings of the Thirty-First AAAI Conference on Artificial Intelligence (AAAI-17)*, Association for the Advancement of Artificial Intelligence, San Francisco, CA, Feb. 4-9, 2017, pp. 4278-4284.

Wang et al., "In vitro fertilization (IVF): a review of 3 decades of clinical innovation and technological advancement," *Therapeutics and Clinical Risk Management* 2(4):355-364, 2006.

Wong et al., "Non-invasive imaging of human embryos before embryonic genome activation predicts development to the blastocyst stage," *Nat Biotechnol* 28(10):1115-1121, 2010.

Zhang et al., "Deep Mutual Learning," *2018 IEEE/CVF Conference on Computer Vision and Pattern Recognition*, Institute of Electrical and Electronics Engineers, Salt Lake City, UT, Jun. 18-23, 2018, pp. 4320-4328.

Khan et al., "Deep Convolutional Neural Networks for Human Embryonic Cell Counting," *ECCV 2016: Computer Vision—ECCV 2016 Workshops*, pp. 339-348, 2016. (23 pages).

Manna et al., "Artificial intelligence techniques for embryo and oocyte classification," *Reprod Biomed Online* 26(1):42-49, 2013.

Rocha et al., "A Method Based on Artificial Intelligence To Fully Automatize The Evaluation of Bovine Blastocyst Images," *Sci Rep* 7:7659, 2017. (10 pages).

\* cited by examiner outer axes: 44.55, 45.15 micron; inner axes: 39.97, 40.57 micron outer axes: 42.83, 48.0 micron; inner axes: 36.34, 39.3 micron

METHOD AND SYSTEM FOR SELECTING EMBRYOS

PRIORITY DOCUMENTS

The present application claims priority from Australian Provisional Patent Application No. 2019901152 titled "METHOD AND SYSTEM FOR SELECTING EMBRYOS" and filed on 4 Apr. 2019, the content of which is hereby incorporated by reference in its entirety.

TECHNICAL FIELD

The present disclosure relates to In-vitro Fertilisation (IVF). In a particular form the present disclosure relates to methods for selecting embryos.

BACKGROUND

An In-Vitro Fertilisation (IVF) procedure starts with an ovarian stimulation phase which stimulates egg production. Eggs (oocytes) are then retrieved from the patient and fertilized in-vitro with sperm which penetrates the Zona Pellucida, which is a glycoprotein layer surrounding the egg (oocyte) to form a zygote. An embryo develops over a period of around 5 days, after which time the embryo has formed a blastocyst (formed of the trophoblast, blastocoele and inner cell mass) suitable for transfer back into the patient. At around 5 days the blastocyst is still surrounded by the Zona Pellucida, from which the blastocyst will hatch to then implant in the endometrial wall. We will refer to the region bounded by the inner surface of the Zona Pellucida as the InnerZonal Cavity (IZC). The selection of the best embryo at the point of transfer is critical to ensure a positive pregnancy outcome. An embryologist visually assesses the embryos using a microscope to make this selection. Some clinics record images of the embryos at the point of selection and an embryologist may score each embryo based on various metrics and their visual assessment down the microscope. For example one commonly used scoring system is the Gardner Scale in which morphological features such as inner cell mass quality, trophectoderm quality, and embryo developmental advancement are evaluated and graded according to an alphanumeric scale. The embryologist then selects one (or more) of the embryos which is then transferred back to the patient.

Thus embryo selection is currently a manual process that involves a subjective assessment of embryos by an embryologist through visual inspection. One of the key challenges in embryo grading is the high level of subjectivity and intra- and inter-operator variability that exists between embryologists of different skill levels. This means that standardization is difficult even within a single laboratory and impossible across the industry as a whole. Thus the process relies heavily on the expertise of the embryologist, and despite their best efforts, the success rates for IVF are still relatively low (around 20%). Whilst the reasons for low pregnancy outcomes are complex, tools to more accurately select the most viable embryo's is expected to result in increases in successful pregnancy outcomes.

To date, several tools have been developed to assist embryologists in selecting viable embryos, including pre-implantation genetic screening (PGS) or time lapse photography. However each approach has crucial limitations. PGS involves the genetic assessment of several cells from the embryo by taking a biopsy, and then screening the extracted cells. Whilst this can be useful to identify genetic risks which may lead to a failed pregnancy, this also has the potential to harm the embryo during the biopsy process. It is also expensive and has limited or no availability in many large developing markets such as China. Another tool that has been considered is the use of time-lapse imaging over the course of embryo development. However this requires expensive specialized hardware that is cost prohibitive for many clinics. Further there is no evidence that it can reliably improve embryo selection. At best it can assist in determining whether an embryo at an early stage will develop through to a mature blastocyst, but it has not been demonstrated to reliably predict pregnancy outcomes and is therefore limited in its utility for embryo selection.

There is thus a need to provide an improved tool for assisting an embryologist to perform selection of an embryo for implantation, or at least to provide a useful alternative to existing tools and systems.

SUMMARY

According to a first aspect, there is provided a method for computationally generating an Artificial Intelligence (AI) model configured to estimate an embryo viability score from an image, the method comprising:

receiving a plurality of images and associated metadata, wherein each image is captured during a pre-determined time window after In-Vitro Fertilisation (IVF) and the pre-determined time window is 24 hours or less, and the metadata associated with the image comprises at least a pregnancy outcome label;

pre-processing each image comprising at least segmenting the image to identify a Zona Pellucida region;

generating an Artificial Intelligence (AI) model configured to generate an embryo viability score from an input image by training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model; and deploying the AI model.

In a further form the set of Zona Pellucida images comprising images in which regions bounded by the Zona Pellucida region are masked.

In a further form, generating the AI model further comprises training one or more additional AI models wherein each additional AI model is either a computer vision model trained using a machine learning method that uses a combination of one or more computer vision descriptors extracted from an image to estimate an embryo viability score, a deep learning model trained on images localised to the embryo comprising both Zona Pellucida and IZC regions, and a deep learning model trained on a set of IntraZonal Cavity (IZC) images in which all regions apart from the IZC are masked, and either using an ensemble method to combine at least two of the at least one Zona deep learning model and the one or more additional AI models to generate the AI model embryo viability score from an input image or using a distillation method to train an AI model to generate the AI model embryo viability score using the at least one Zona deep learning model and the one or more additional AI models to generate the AI model.

In one form, the AI model is generated using an ensemble model comprising selecting at least two contrasting AI models from the at least one Zona deep learning model and the one or more additional AI models, and selection of AI models is performed to generate a set of contrasting AI models and applying a voting strategy to the at least two contrasting AI models that defines how the selected at least two contrasting AI models are combined to generate an outcome score for an image.

In a further form, selecting at least two contrasting AI models comprises generating a distribution of embryo viability scores from a set of images for each of the at least one Zona deep learning model and the one or more additional AI models, and comparing the distributions and discarding a model if the associated distributions are too similar to another distribution to select AI models with contrasting distributions.

In one form, the pre-determined time window is a 24 hour timer period beginning 5 days after fertilisation. In one form, the pregnancy outcome label is a ground-truth pregnancy outcome measurement performed within 12 weeks after embryo transfer. In a further form, the ground-truth pregnancy outcome measurement is whether a foetal heartbeat is detected.

In one form the method further comprises cleaning the plurality of image comprising identifying images with likely incorrect pregnancy outcome labels, and excluding or re-labelling the identified images.

In a further form, cleaning the plurality of images comprises estimating the likelihood that a pregnancy outcome label associated with an image is incorrect and comparing against a threshold value, and then excluding or relabelling images with a likelihood exceeding the threshold value.

In a further form, estimating the likelihood a pregnancy outcome label associated with an image is incorrect is be performed by using a plurality of AI classification models and a k-fold cross validation method in which the plurality of images are split into k mutually exclusive validation datasets, and each of the plurality of AI classifications model is trained on k−1 validation datasets in combination and then used to classify images in the remaining validation dataset, and the likelihood is determined based on the number of AI classification models which misclassify the pregnancy outcome label of an image.

In one form, training each AI model or generating the ensemble model comprises assessing the performance of an AI model using a plurality of metrics comprising at least one accuracy metric and at least one confidence metric, or a metric combining accuracy and confidence.

In one form, pre-processing the image further comprises cropping the image by localising an embryo in the image using a deep learning or computer vision method.

In one form, pre-processing the image further comprises one or more of padding the image, normalising the colour balance, normalising the brightness, and scaling the image to a predefined resolution.

In one form, padding the image may be performed to generate a square aspect ratio for the image. In one form, the method further comprises generating one or more one or more augmented images for use in training an AI model. Preparing each image may also comprise generating one or more augmented images by making a copy of an image with a change or the augmentation may be performed on the image. It may be performed prior to training or during training (on the fly). Any number of augmentations may be performed with varying amounts of 90 degree rotations of the image, mirror flip, a non-90 degree rotation where a diagonal border is filled in to match a background colour, image blurring, adjusting an image contrast using an intensity histogram, and applying one or more small random translations in both the horizontal and/or vertical direction, random rotations, JPEG noise, random image resizing, random hue jitter, random brightness jitter, contrast limited adaptive histogram equalization, random flip/mirror, image sharpening, image embossing, random brightness and contrast, RGB colour shift, random hue and saturation, channel shuffle, swap RGB to BGR or RBG or other, coarse dropout, motion blur, median blur, Gaussian blur, random shift-scale-rotate (i.e. all three combined).

In one form, during training of an AI model one or more augmented images are generated for each image in the training set and during assessment of the validation set, the results for the one or more augmented images are combined to generate a single result for the image. The results may be combined using one of mean-confidence, median-confidence, majority-mean-confidence, max-confidence methods or other voting strategies for combining model predictions.

In one form pre-processing an image may further comprise annotating the image using one or more feature descriptor models, and masking all areas of the image except those within a given radius of the descriptor key point. The one or more feature descriptor models may comprise a Gray-Level Co-Occurrence Matrix (GLCM) Texture Analysis, a Histogram of Oriented Gradients (HOG), a Oriented Features from Accelerated Segment Test (FAST) and Rotated Binary Robust Independent Elementary Features (BRIEF), a Binary Robust Invariant Scalable Key-points (BRISK), a Maximally Stable Extremal Regions (MSER) or a Good Features To Track (GFTT) feature detector.

In one form each AI model generates an outcome score wherein the outcome is a n-ary outcome having n states, and training an AI model comprises a plurality of training-validation cycles further comprises randomly allocating the plurality of images to one of a training set, a validation set or a blind validation set, such that the training dataset comprises at least 60% of the images, the validation dataset comprises at least 10% of the images, and the blind validation dataset comprises at least 10% of the images, and after allocating the images to the training set, validation set and blind validation set, calculating the frequency of each of the n-ary outcome states in each of the training set, validation set and blind validation set, and testing that the frequencies are similar, and if the frequencies are not similar then discarding the allocation and repeating the randomisation until a randomisation is obtained in which the frequencies are similar.

In one form, training a computer vision model comprising performing a plurality of training-validation cycles, and during each cycle the images are clustered based on the computer vision descriptors using an unsupervised clustering algorithm to generate a set of clusters, and each image is assigned to a cluster using a distance measure based on the values of the computer vision descriptors of the image, and a supervised learning method is use to determine whether a particular combination of these features corresponds to an outcome measure, and frequency information of the presence of each computer vision descriptor in the plurality of images.

In one form the deep learning model may be a convolutional neural network (CNN) and for an input image each deep learning model generates an outcome probability.

In one form the deep learning method may use a loss function configured to modify an optimization surface is to emphasise global minima. The loss function may include a residual term defined in terms of the network weights, which encodes the collective difference in the predicted value from the model and the target outcome for each image, and includes it as an additional contribution to the normal cross entropy loss function.

In one form the method may be performed on a cloud based computing system using a webserver, a database, and a plurality of training servers, wherein the webserver receives one or more model training parameters from a user, and the webserver initiates a training process on one or more of the plurality of training servers, comprising uploading training code to one of the plurality the training server, and the training server requests the plurality of images and associated metadata from a data repository, and performs the steps of preparing each image, generating a plurality of computer vision models and generating a plurality of deep learning models, and each training server is configured to periodically save the models to a storage service, and accuracy information to one or more log files to allow a training process to be restarted. In a further form the ensemble model may be trained to bias residual inaccuracies to minimize false negatives.

In one form the outcome is a binary outcome of either viable or non-viable, and randomisation may comprise calculating the frequency of images with a viable classification and a non-viable classification, in each of the training set, validation set and blind validation set and testing if they are similar. In one form the outcome measure is a measure of embryo viability using the viability classification associated with each image. In one form each outcome probability may be a probability that the image is viable. In one form each image may be a phase contrast image.

According to a second aspect, there is provided a method for computationally generating an embryo viability score from an image, the method comprising:

generating, in a computational system, an Artificial Intelligence (AI) model configured to generate an embryo viability score from an image according to the method of the first aspect;

receiving, from a user via a user interface of the computational system, an image captured during a pre-determined time window after In-Vitro Fertilisation (IVF); and pre-processing the image according to the pre-processing steps used to generate the AI model;

providing the pre-processed image to the AI model to obtain an estimate of the embryo viability score; and sending the embryo viability score to the user via the user interface According to a third aspect, there is provided a method for obtaining an embryo viability score from an image, comprising:

uploading, via a user interface, an image captured during a pre-determined time window after In-Vitro Fertilisation (IVF) to a cloud based Artificial Intelligence (AI) model configured to generate an embryo viability score from an image wherein the AI model is generated according to the method of the first aspect;

receiving an embryo viability score from the cloud based AI model via the user interface.

According to a fourth aspect, there is provided a cloud based computational system configured to computationally generate an Artificial Intelligence (AI) model configured to estimate an embryo viability score from an image according to the method of the first aspect.

According to a fifth aspect, there is provided a cloud based computational system configured to computationally generate an embryo viability score from an image, wherein the computational system comprises:

an Artificial Intelligence (AI) model configured to generate an embryo viability score from an image wherein the AI model is generated according to the method of the first aspect;

receiving, from a user via a user interface of the computational system, an image captured during a pre-determined time window after In-Vitro Fertilisation (IVF);

providing the image to the AI model to obtain an embryo viability score; and sending the embryo viability score to the user via the user interface.

According to a sixth aspect, there is provided a computational system configured to generate an embryo viability score from an image, wherein the computational system comprises at least one processor, and at least one memory comprising instructions to configure the at least one processor to:

receive an image captured during a pre-determined time window after In-Vitro Fertilisation (IVF)

upload, via a user interface, the image captured during a pre-determined time window after In-Vitro Fertilisation (IVF) to a cloud based Artificial Intelligence (AI) model configured to generate an embryo viability score from an image wherein the AI model is generated according to the method of the first aspect;

receive an embryo viability score from the cloud based AI model; and display the embryo viability score via the user interface.

BRIEF DESCRIPTION OF DRAWINGS

Embodiments of the present disclosure will be discussed with reference to the accompanying drawings wherein.

In the following description, like reference characters designate like or corresponding parts throughout the figures.

DESCRIPTION OF EMBODIMENTS

Figure 1A:
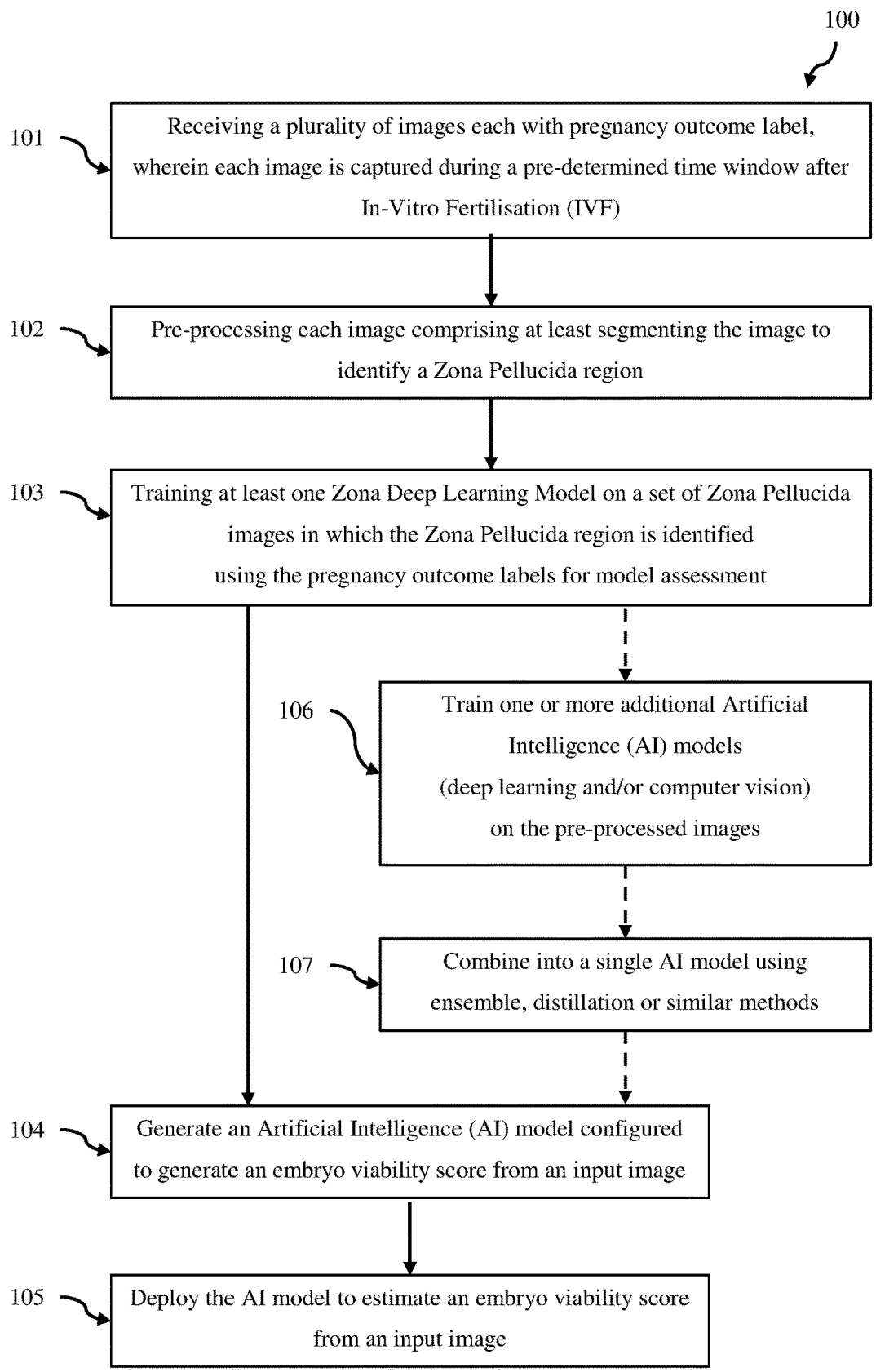
FIG. 1A is a schematic flowchart of the generation of an Artificial Intelligence (AI) model configured to estimate an embryo viability score from an image according to an embodiment.
Figure 1B:
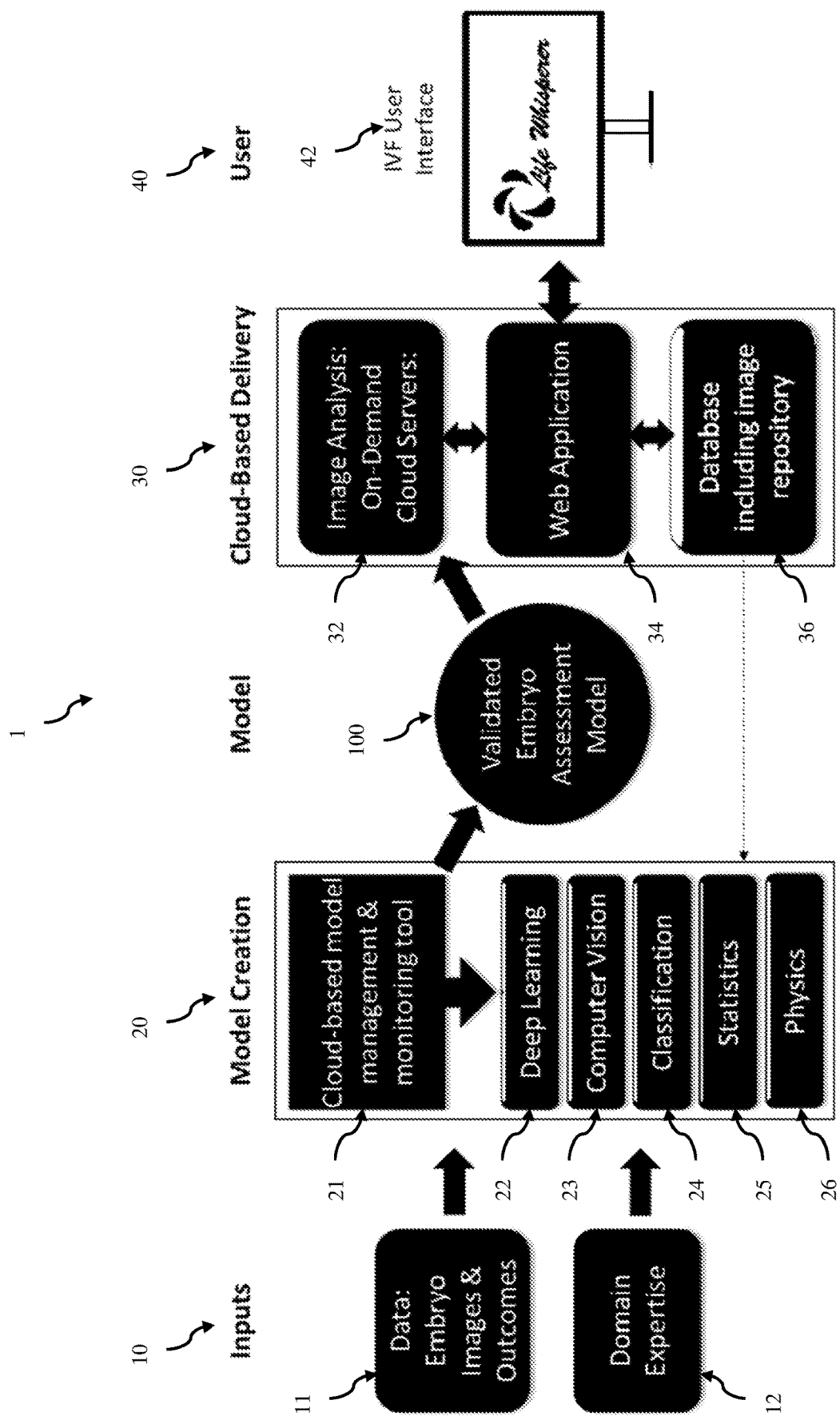
FIG. 1B is a schematic block diagram of a cloud based computation system configured to computationally generate and use an AI model configured to estimate an embryo viability score from an image according to an embodiment.
Figure 2:
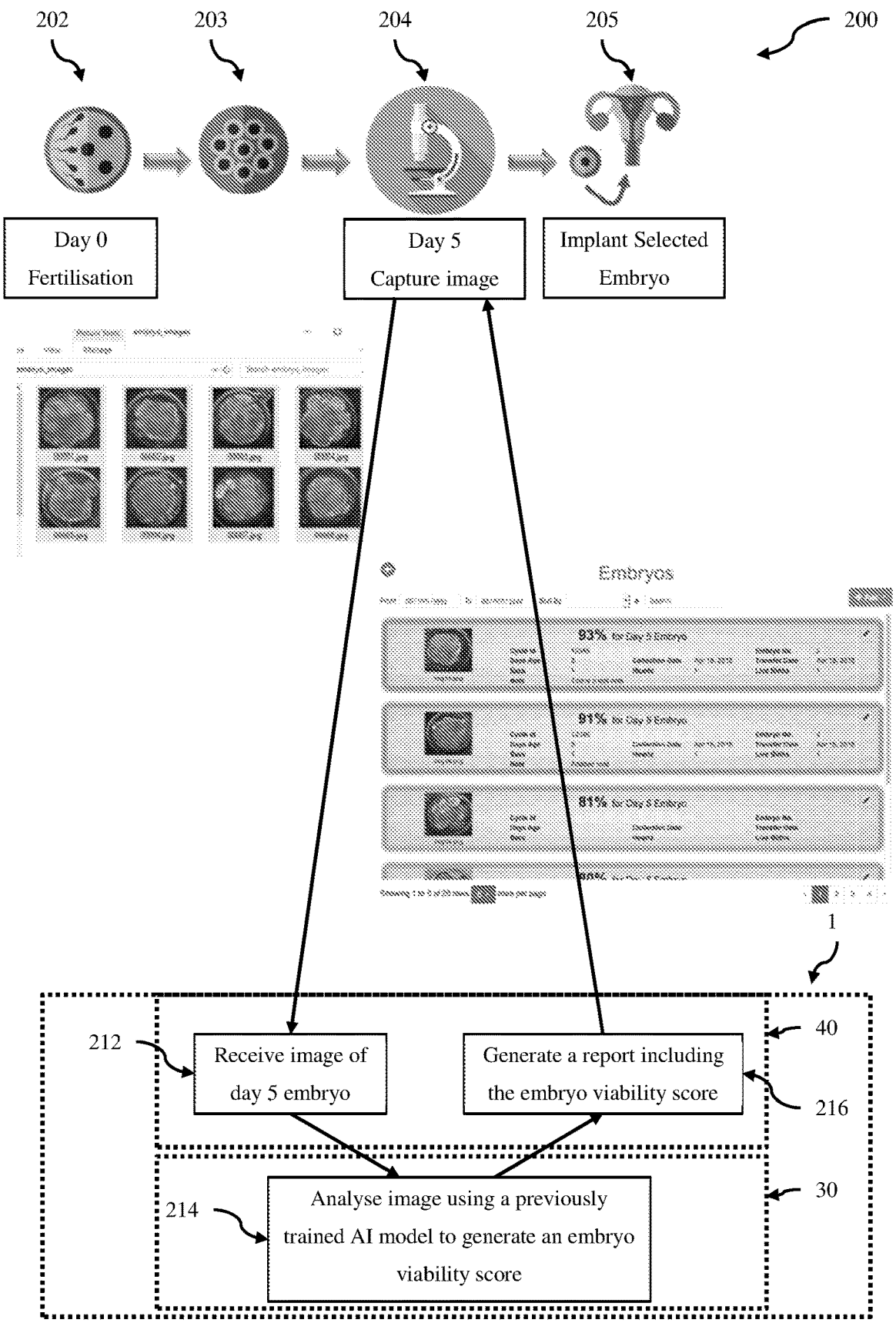
FIG. 2 is a schematic diagram of an IVF procedure using an AI model configured to estimate an embryo viability score from an image to assist in selecting an embryo for implantation according to an embodiment.

With reference to FIGS. 1A, 1B and 2, embodiments of a cloud based computation system 1 configured to computationally generate and use an Artificial Intelligence (AI) model 100 configured to estimate an embryo viability score from a single image of an embryo will now be discussed. We will also refer to this AI model 100 as an embryo viability assessment model. FIG. 1A is schematic flow chart of the generation of an AI model 100 using a cloud based computation system 1 according to an embodiment. A plurality of images and associated metadata is received (or obtained) from one or more data sources 101. Each image is captured during a pre-determined time window after In-Vitro Fertilisation (IVF), such as a 24 hour period starting at day 5 post fertilisation. The images and metadata can be sourced from IVF clinics and may be images captured using optical light microscopy including phase contrast images. The metadata includes a pregnancy outcome label (e.g. heart beat detected at first scan post IVF) and may include a range of other clinical and patient information.

The images are then pre-processed 102, with the pre-processing including segmenting the image to identify a Zona Pellucida region of the image. The segmentation may also include identification of the IntraZonal Cavity (IZC) which is surrounded by the Zona Pellucida region. Pre-processing an image may also involve one or more (or all) of object detection, alpha channel removal, padding, cropping/localising, normalising the colour balance, normalising the brightness, and/or scaling the image to a predefined resolution as discussed below. Pre-processing the image may also include calculating/determining computer vision feature descriptors from an image, and performing one or more image augmentations, or generating one or more augmented images.

At least one Zona Deep Learning model is trained on a set of Zona Pellucida images 103 in order to generate the Artificial Intelligence (AI) model 100 configured to generate an embryo viability score from an input image 104. The set of Zona Pellucida images are images in which the Zona Pellucida regions are identified (e.g. during segmentation in step 102). In some embodiments the set of Zona Pellucida images are images in all regions of the image apart from the Zona Pellucida region are masked (i.e. so the deep learning model is only trained on information from/relating to the Zona Pellucida region). The pregnancy outcome labels are used at least in the assessment of a trained model (i.e. to assess accuracy/performance) and may also be used in model training (e.g. by the loss function to drive model optimisation). Multiple Zona Deep Learning Models may be trained, with the best performing model selected as the AI model 100.

In another embodiment, one or more additional AI models are trained on the pre-processed images 106. These may be additional deep learning models trained directly on the embryo image, and/or on a set of IZC images in which all regions of the image apart from the IZC are masked, or Computer Vision (CV) models trained to combine computer vision features/descriptors generating in the pre-processing step 102 to generate an embryo viability score from an image. Each of the Computer Vision models uses a combination of one or more computer vision descriptors extracted from an image to estimate an embryo viability score of an embryo in an image, and a machine learning method performs a plurality of training-validation cycles to generate the CV model. Similarly each of the deep learning models is trained in a plurality of training-validation cycles so that each deep learning model learns how to estimate an embryo viability score of an embryo in an image. During training images may be randomly assigned to each of a training set, a validation set and a blind validation set and each training-validation cycle comprises a (further) randomisation of the plurality of images within each of the training set, validation set and blind validation set. That is the images within each set are randomly sampled each cycle, so that each cycle a different subset of images are analysed, or are analysed in a different ordering. Note however that as they are randomly sampled this does allow two or more sets to be identical, provided this occurred through a random selection process.

The multiple AI models are then combined into the single AI model 100, using ensemble, distillation or other similar techniques 107 to generate the AU model 100 in step 104. An ensemble approach involves selecting models from the set of available models and using a voting strategy that defines how an outcome score is generated from the individual outcomes of the selected models. In some embodiments, the models are selected to ensure that the results contrast to generate a distribution of results. These are preferably as independent as possible to ensure a good distribution of results. In a distillation method, the multiple AI models are used as teachers to train a single student model, with the student model becoming the final AI model 100.

In step 104 a final AI model is selected. This may be one of the Zona Deep Learning models trained in step 103, or it may be a model obtained using an ensemble, distillation or similar combination step (step 107) where the training included at least one Zona Deep Learning model (from 103) and one or more additional AI models (Deep Learning and/or CV; step 106). Once a final AI model 100 is generated (104), this is deployed for operational use to estimate an embryo viability score from an input image 105, e.g. on a cloud server that is configured to receive a phase contrast image of a day 5 embryo captured at an IVF clinic using a light microscope. This is further illustrated in FIG. 2 and discussed below. In some embodiments deployment comprises saving or exporting the trained model, such as by writing the model weights and associated model metadata to a file which is transferred to the operational computation system and uploaded to recreate the trained model. Deployment may also comprise moving, copying, or replicating the trained model onto an operational computational system, such as one or more cloud based servers, or locally based computer servers at IVF clinics. In one embodiment deployment may comprise reconfiguring the computational system the AI model was trained on to accept new images and generate viability estimates using the trained model, for example by adding an interface to receive images, run the trained model on the received images, and to send the results back to the source, or to store the results for later retrieval. The deployed system is configured to receive an input image, and perform any pre-processing steps used to generate the AI model (i.e. so new images are pre-processed in the same way as the trained images). In some embodiments the images may be pre-processed prior to uploading to the cloud system (i.e. local pre-processing). In some embodiments the pre-processing may be distributed between the local system and the remote (e.g. cloud) system. The deployed model is executed or run over the image to generate an embryo viability score that is then provided to the user.

FIG. 1B is schematic block diagram a cloud based computation system 1 configured to computationally generate an AI model 100 configured to estimate an embryo viability score from an image (i.e. an embryo viability assessment model), and then use this AI model 100 to generate an embryo viability score (i.e. an outcome score) which is an estimate (or assessment) of the viability of a received image. The input 10 comprises data such as the images of the embryo and pregnancy outcome information (e.g. heart beat detected at first ultrasound scan post IVF, live birth or not, or successful implantation) which can be used to generate a viability classification. This is provided as input to the model creation process 20 which creates and trains AI models. These include the Zona Deep Learning model (103) and in some embodiments also include additional deep learning and/or computer vision models (106). Models may be trained using a variety of methods and information including the use of segmented datasets (e.g. Zona images, IZC images) and pregnancy outcome data. Where multiple AI models are trained a best performing model may be selected according to some criteria, such as based on the pregnancy outcome information or multiple AI models may be combined using an ensemble model which selects AI models and generates an outcome based on a voting strategy, or a distillation method may be used in which the multiple AI models are used as teachers to train a student AI model, or some other similar method may be used to combine the multiple models into a single model. A cloud based model management and monitoring tool, which we refer to as the model monitor 21, is used to create (or generate) the AI models. This uses a series of linked services, such as Amazon Web Services (AWS) which manages the training, logging and tracking of models specific to image analysis and the model. Other similar services on other cloud platforms may be used. These may use deep learning methods 22, computer vision methods 23, classification methods 24, statistical methods 25 and physics based models 26. The model generation may also use domain expertise 12 as input, such as from embryologists, computer scientists, scientific/technical literature, etc., for example on what features to extract and use in a Computer Vision model. The output of the model creation process is an instance of an AI model (100) which we will also refer to as a validated embryo assessment model A cloud based delivery platform 30 is used which provides a user interface 42 to the system for a user 40. This is further illustrated with reference to FIG. 2 which is a schematic diagram of an IVF procedure 200 using a previously trained AI model to generate an embryo viability score to assist in selecting an embryo for implantation according to an embodiment. At day 0, harvested eggs are fertilised 202. These are then in-vitro cultured for several days and then an image of the embryo is captured, for example using a phase contrast microscope 204. As discussed below, it was generally found that images taken 5 days after in-vitro fertilisation produced better results than images taken at earlier days. Thus preferably the model is trained and used on day 5 embryos, however it is to be understood that a model could be trained and used on embryo's taken during a specific time window with reference to a specific epoch. In one embodiment the time is 24 hours, but other time windows such as 12 hours, 36 hours, or 48 hours could be used. Generally smaller time windows of 24 hours or less are preferable to ensure greater similarity in appearance. In one embodiment this could a specific day which is a 24 hour window starting at the beginning of the day (0:00) to the end of the day (23:39), or specific days such days 4 or 5 (a 48 hour window starting at the start of day 4). Alternatively the time window could define a window size and epoch, such as 24 hours centred on day 5 (i.e. 4.5 days to 5.5 days). The time window could be open ended with a lower bound, such as at least 5 days. As noted above whilst is preferable to use images of embryos from a time window of 24 hours around day 5, it is to be understood that earlier stage embryos could be used including day 3 or day 4 images.

Typically several eggs will be fertilised at the same time and thus a set of multiple images will be obtained for consideration of which embryo is the best (i.e. most viable) to implant. The user uploads the captured image to the platform 30 via user interface 42, for example using "drag and drop" functionality. The user can upload a single image or multiple images, for example to assist in selection which embryo from a set of multiple embryos being considered for implantation. The platform 30 receives the one or more images 312 which are is stored in a database 36 that includes an image repository. The cloud based delivery platform comprises on-demand cloud servers 32 that can do the image pre-processing (e.g. object detection, segmentation, padded, normalised, cropped, centred, etc.) and then provide the processed image to the trained AI (embryo viability assessment) model 100 which executes on one of the on-demand cloud servers 32 to generate an embryo viability score 314. A report including the embryo viability score is generated 316 and this is sent or otherwise provided to the user 40, such as through the user interface 42. The user (e.g. embryologist) receives the embryo viability score via the user interface and can then use the viability score to assist in a decision of whether to implant the embryo, or which is the best embryo in the set to implant. The selected embryo is then implanted 205. To assist in further refinement of the AI model, pregnancy outcome data, such as detection (or not) of a heartbeat in the first ultrasound scan after implantation (normally around 6-10 weeks post fertilisation) may be provided to the system. This allows the AI model to be retrained and updated as more data becomes available.

The image may be captured using a range of imaging systems, such as those found in existing IVF clinics. This has the advantage of not requiring IVF clinics to purchase new imaging systems or use specific imaging systems. Imaging systems are typically light microscopes configured to capture single phase contrast images embryos. However it will be understood that other imaging systems may be used, in particular optical light microscope systems using a range of imaging sensors and image capture techniques. These may include phase contrast microscopy, polarised light microscopy, differential interference contrast (DIC) microscopy, dark-field microscopy, and bright field microscopy. Images may be captured using a conventional optical microscope fitted with a camera or image sensor, or the image may be captured by a camera with an integrated optical system capable of taking a high resolution or high magnification image, including smart phone systems. Image sensors may be a CMOS sensor chip or a charge coupled device (CCD), each with associated electronics. The optical system may be configured to collect specific wavelengths or use filters including band pass filters to collect (or exclude) specific wavelengths. Some image sensors may be configured to operate or sensitive to light in specific wavelengths, or at wavelengths beyond the optical range including in the Infrared (IR) or near IR. In some embodiments the imaging sensor is a multispectral camera which collects an image at multiple distinct wavelength ranges. Illumination systems may also be used illuminate the embryo with light of a particular wavelength, in a particular wavelength band, or a particular intensity. Stops and other components may be used to restrict or modify illumination to certain parts of the image (or image plane).

Further the image used in embodiments described herein may be sourced from video and time lapse imaging systems. A video stream is a periodic sequence of image frames where the interval between image frames is defined by the capture frame rate (e.g. 24 or 48 frames per second). Similarly a time-lapse system captures a sequence of images with a very slow frame rate (e.g. 1 image per hour) to obtain a sequence of images as the embryo grows (post-fertilisation). Accordingly it will be understood that the image used in embodiments described herein may be a single image extracted from a video stream or a time lapse sequence of images of an embryo. Where an image is extracted from a video stream or a time lapse sequence, the image to use may be selected as the image with a capture time nearest to a reference time point such as 5.0 or 5.5 days post fertilisation.

In some embodiments pre-processing may include an image quality assessment so that an image may be excluded if it fails a quality assessment. A further image may be captured if the original image fails a quality assessment. In embodiments where the image is selected from a video stream or time lapse sequence, then the image selected is the first image which passes the quality assessment nearest the reference time. Alternatively a reference time window may be defined, (e.g. 30 minutes following the start of day 5.0) along with image quality criteria. In this embodiment the image selected is the image with the highest quality during the reference time window is selected. The image quality criteria used in performing quality assessment may be based on a pixel colour distribution, a brightness range, and/or an unusual image property or feature that indicates poor quality or equipment failure. The thresholds may be determined by analysing a reference set of images. This may be based on manual assessment or automated systems which extract outliers from distributions.

Figure 3A:
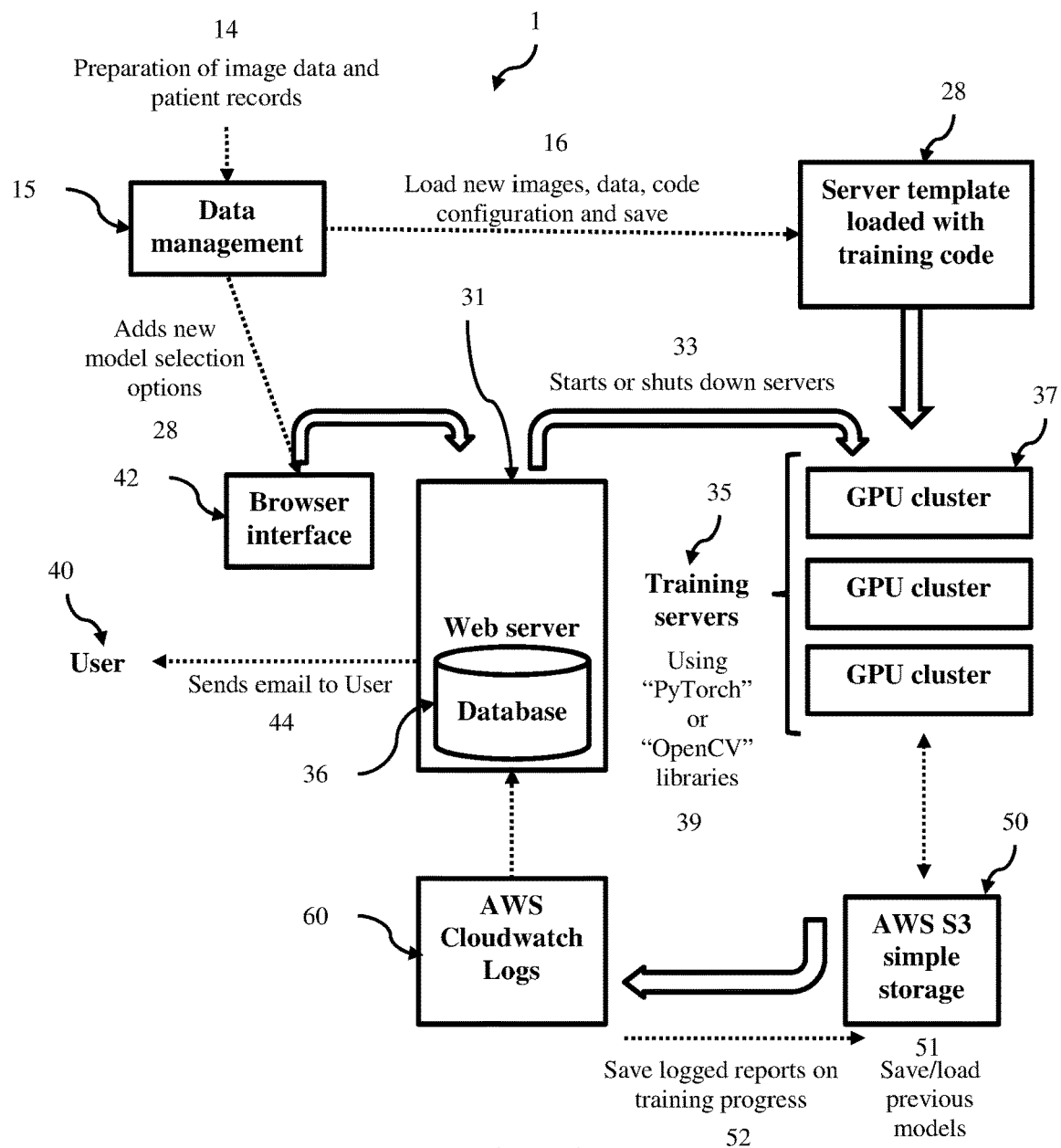
FIG. 3A is schematic architecture diagram of cloud based computation system configured to generate and use an AI model configured to estimate an embryo viability score from an image according to an embodiment.

The generation of the AI embryo viability assessment model 100 can be further understood with reference to FIG. 3A which is a schematic architecture diagram of cloud based computation system 1 configured to generate and use an AI model 100 configured to estimate an embryo viability score from an image according to an embodiment. With reference to FIG. 1B the AI model generation method is handled by the model monitor 21.

The model monitor 21 allows a user 40 to provide image data and metadata 14 to a data management platform which includes a data repository. A data preparation step is performed, for example to move the images to specific folder, and to rename and perform pre-processing on the image such as objection detection, segmentation, alpha channel removal, padding, cropping/localising, normalising, scaling, etc. Feature descriptors may also be calculated, and augmented images generated in advance. However additional pre-processing including augmentation may also be performed during training (i.e. on the fly). Images may also undergo quality assessment, to allow rejection of clearly poor images and allow capture of replacement images. Similarly patient records or other clinical data is processed (prepared) to extra an embryo viability classification (e.g. viable or non-viable) which is linked or associated with each image to enable use in training the AI models and/or in assessment. The prepared data is loaded 16 onto a cloud provider (e.g. AWS) template server 28 with the most recent version of the training algorithms. The template server is saved, and multiple copies made across a range of training server clusters 37, which may be CPU, GPU, ASIC, FPGA, or TPU (Tensor Processing Unit)-based, which form training servers 35. The model monitor web server 31 then applies for a training server 37 from a plurality of cloud based training servers 35 for each job submitted by the user 40. Each training server 35 runs the pre-prepared code (from template server 28) for training an AI model, using a library such as Pytorch, Tensorflow or equivalent, and may use a computer vision library such as OpenCV. PyTorch and OpenCV are open-source libraries with low-level commands for constructing CV machine learning models.

The training servers 37 manage the training process. This may include may dividing the images in to training, validation, and blind validation sets, for example using a random allocation process. Further during a training-validation cycle the training servers 37 may also randomise the set of images at the start of the cycle so that each cycle a different subset of images are analysed, or are analysed in a different ordering. If pre-processing was not performed earlier or was incomplete (e.g. during data management) then additional pre-processing may be performed including object detection, segmentation and generation of masked data sets (e.g. just Zona Pellucida images, or just IZC images), calculation/estimation of CV feature descriptors, and generating data augmentations. Pre-processing may also include padding, normalising, etc. as required. That is the pre-processing step 102 may be performed prior to training, during training, or some combination (i.e. distributed pre-processing). The number of training servers 35 being run can be managed from the browser interface. As the training progresses, logging information about the status of the training is recorded 62 onto a distributed logging service such as Cloudwatch 60. Key patient and accuracy information is also parsed out of the logs and saved into a relational database 36. The models are also periodically saved 51 to a data storage (e.g. AWS Simple Storage Service (S3) or similar cloud storage service) 50 so they can be retrieved and loaded at a later date (for example to restart in case of an error or other stoppage). The user 40 is sent email updates 44 regarding the status of the training servers if their jobs are complete, or an error is encountered.

Figure 3B:
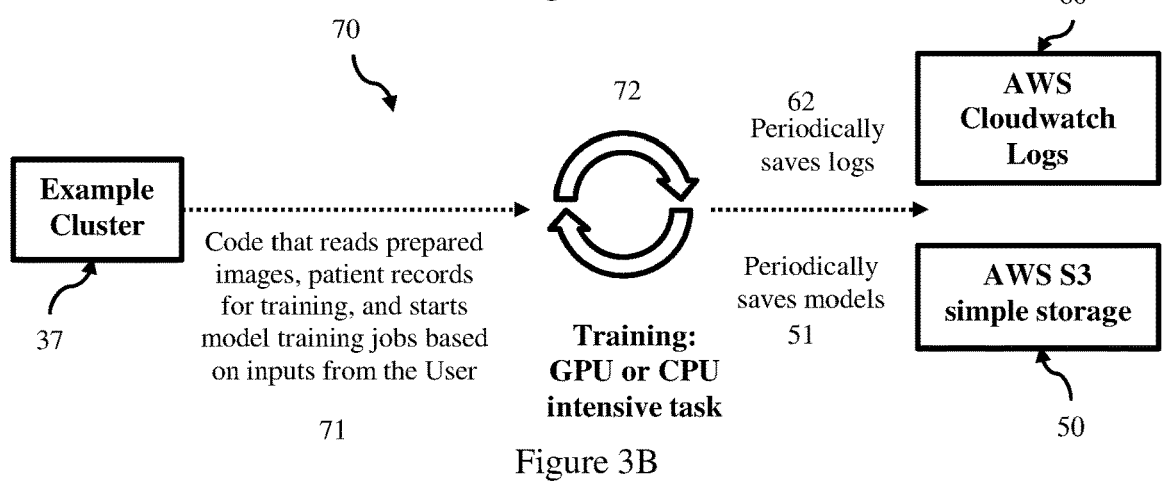
FIG. 3B is a schematic flowchart of a model training process on a training server according to an embodiment.

Within each training cluster 37, a number of processes take place. Once a cluster is started via the web server 31, a script is automatically run, which reads the prepared images and patient records, and begins the specific Pytorch/OpenCV training code requested 71. The input parameters for the model training 28 are supplied by the user 40 via the browser interface 42 or via a configuration script. The training process 72 is then initiated for the requested model parameters, and can be a lengthy and intensive task. Therefore, so as not to lose progress while the training is in progress, the logs are periodically saved 62 to the logging (e.g. AWS Cloudwatch) service 60 and the current version of the model (while training) is saved 51 to the data (e.g. S3) storage service 51 for later retrieval and use. An embodiment of a schematic flowchart of a model training process on a training server is shown in FIG. 3B. With access to a range of trained AI models on the data storage service, multiple models can be combined together for example using ensemble, distillation or similar approaches in order to incorporate a range of deep learning models (e.g. PyTorch) and/or targeted computer vision models (e.g. OpenCV) to generate a robust AI model 100 which is provided to the cloud based delivery platform 30.

The cloud-based delivery platform 30 system then allows users 10 to drag and drop images directly onto the web application 34, which prepares the image and passes the image to the trained/validated AI model 100 to obtain an embryo viability score which is immediately returned in a report (as illustrated in FIG. 2). The web application 34 also allows clinics to store data such as images and patient information in database 36, create a variety of reports on the data, create audit reports on the usage of the tool for their organisation, group or specific users, as well as billing and user accounts (e.g. create users, delete users, reset passwords, change access levels, etc.). The cloud-based delivery platform 30 also enables product admin to access the system to create new customer accounts and users, reset passwords, as well as access to customer/user accounts (including data and screens) to facilitate technical support.

The various steps and variations in generation of embodiments of an AI model configured to estimate an embryo viability score from an image will now be discussed in further detail. With reference to FIG. 1A, the model is trained and uses images captured 5 days post fertilisation (i.e. a 24 hour period from day 5:00:00 to day 5:23:59). Studies on a validated model indicate that model performance is significantly improved using images taken at day 5 post fertilisation compared to images taken at day 4 post fertilisation. However as noted above effective models can still be developed using a shorter time window such as 12 hours, or images taken at other days such as day 3 or day 4, or a minimum time period after fertilisation such as at least 5 days (e.g. open ended time window). What is perhaps more important than the exact time window (e.g. 4 day or 5 days) is that images used for training of an AI model, and then subsequent classification by the trained AI model, are taken during similar and preferably the same time windows (e.g. the same 12 or 24 hour time window).

Prior to analysis, each image undergoes pre-processing (image preparation) procedure 102 including at least segmenting the image to identify a Zona Pellucida region. A range of pre-processing steps or techniques may be applied. The may be performed after adding to the data store 14 or during training by a training server 37. In some embodiments an objection detection (localisation) module is used to detect and localise the image on the embryo. Objection detection/localisation comprises estimating the bounding box containing an embryo. This can be used for cropping and/or segmentation of the image. The image may also be padded with a given boundary, and then the color balance and brightness are normalized. The image is then cropped so that the outer region of the embryo is close to the boundary of the image. This is achieved using computer vision techniques for boundary selection, including the use of AI object detection models. Image segmentation is a computer vision technique that is useful for preparing the image for certain models to pick out relevant areas for the model training to focus on such as the Zona Pellucida, and the IntraZonal Cavity (IZC). The image may masked to generate images of just the Zona Pellucida (i.e. crop the border of the Zona Pellucida, and mask the IZC—see FIG. 6F) or just IZC (i.e. crop to the border of the IZC to exclude the Zona Pellucida (FIG. 6G). The background may be left in in the image or it may be masked as well. Embryo viability models may then be trained using just the masked images, for example Zona images which are masked to just contain the Zona Pellucida and background of the image, and/or IZC images which are masked to just contain the IZC. Scaling involves rescaling the image to a predefined scale to suit the particular model being trained. Augmentation involves incorporating making small changes to a copy of the images, such as rotations of the image in order to control for the direction of the embryo dish. The use of segmentation prior to deep learning was found to have a significant effect on the performance of the deep learning method. Similarly augmentation was important for generating a robust model.

A range of image pre-processing techniques may be used for the preparation of human embryo images prior to training an AI model. These include:

Alpha Channel Stripping comprises stripping an image of an alpha channel (if present) to ensure it is coded in a 3-channel format (e.g. RGB), for example to remove transparency maps;

Padding/Bolstering each image with a padded border, to generate a square aspect ratio, prior to segmentation, cropping or boundary-finding. This process ensured that image dimensions were consistent, comparable, and compatible for deep learning methods, which typically require square dimension images as input, while also ensuring that no key components of the image were cropped;

Normalizing the RGB (red-green-blue) or gray-scale images to a fixed mean value for all the images. For example this includes taking the mean of each RGB channel, and dividing each channel by its mean value. Each channel was then multiplied by a fixed value of 100/255, in order to ensure the mean value of each image in RGB space was (100, 100, 100). This step ensured that color biases among the images were suppressed, and that the brightness of each image was normalized;

Thresholding images using binary, Otsu, or adaptive methods. Includes morphological processing of the image using dilation (opening), erosion (closing) and scale gradients, and using a scaled mask to extract the outer and inner boundaries of a shape;

Object Detection/Cropping the image to localise the image on the embryo and ensure that there are no artefacts around the edges of the image. This may be performed using an Object Detector which uses an object detection model (discussed below) which is trained to estimate a bounding box which contains the embryo (including the Zona Pellucida);

Extracting the geometric properties of the boundaries using an elliptical Hough transform of the image contours, for example the best ellipse fit from an elliptical Hough transform calculated on the binary threshold map of the image. This method acts by selecting the hard boundary of the embryo in the image, and by cropping the square boundary of the new image so that the longest radius of the new ellipse is encompassed by the new image width and height, and so that the center of the ellipse is the center of the new image;

Zooming the image by ensuring a consistently centred image with a consistent border size around the elliptical region;

Segmenting the image to identify the Zona Pellucida region and the cytoplasmic IntraZonal Cavity (IZC) region. Segmentation may be performed by calculating the best-fit contour around an un-elliptical image using a Geometrical Active Contour (GAC) model, or morphological snake, within a given region. The inner and other regions of the snake can be treated differently depending on the focus of the trained model on the zona pellucida region or the cytoplasmic (IntraZonal Cavity) region, that may contain a blastocyst. Alternatively a Semantic Segmentation model may be trained which identifies a class for each pixel in an image. In one embodiment a semantic segmentation model was developed using a U-Net architecture with a pretrained ResNet-50 encoder to segment the Zona Pellucida and IZC. The model was trained using a BinaryCrossEntropy loss function;

Annotating the image by selecting feature descriptors, and masking all areas of the image except those within a given radius of the descriptor key point;

Resizing/scaling the entire set of images to a specified resolution; and

Tensor conversion comprising transforming each image to a tensor rather than a visually displayable image, as this data format is more usable by deep learning models. In one embodiment, Tensor normalization was obtained from standard pre-trained ImageNet values with a mean: (0.485, 0.456, 0.406) and standard deviation (0.299, 0.224, 0.225).

Figure 4:
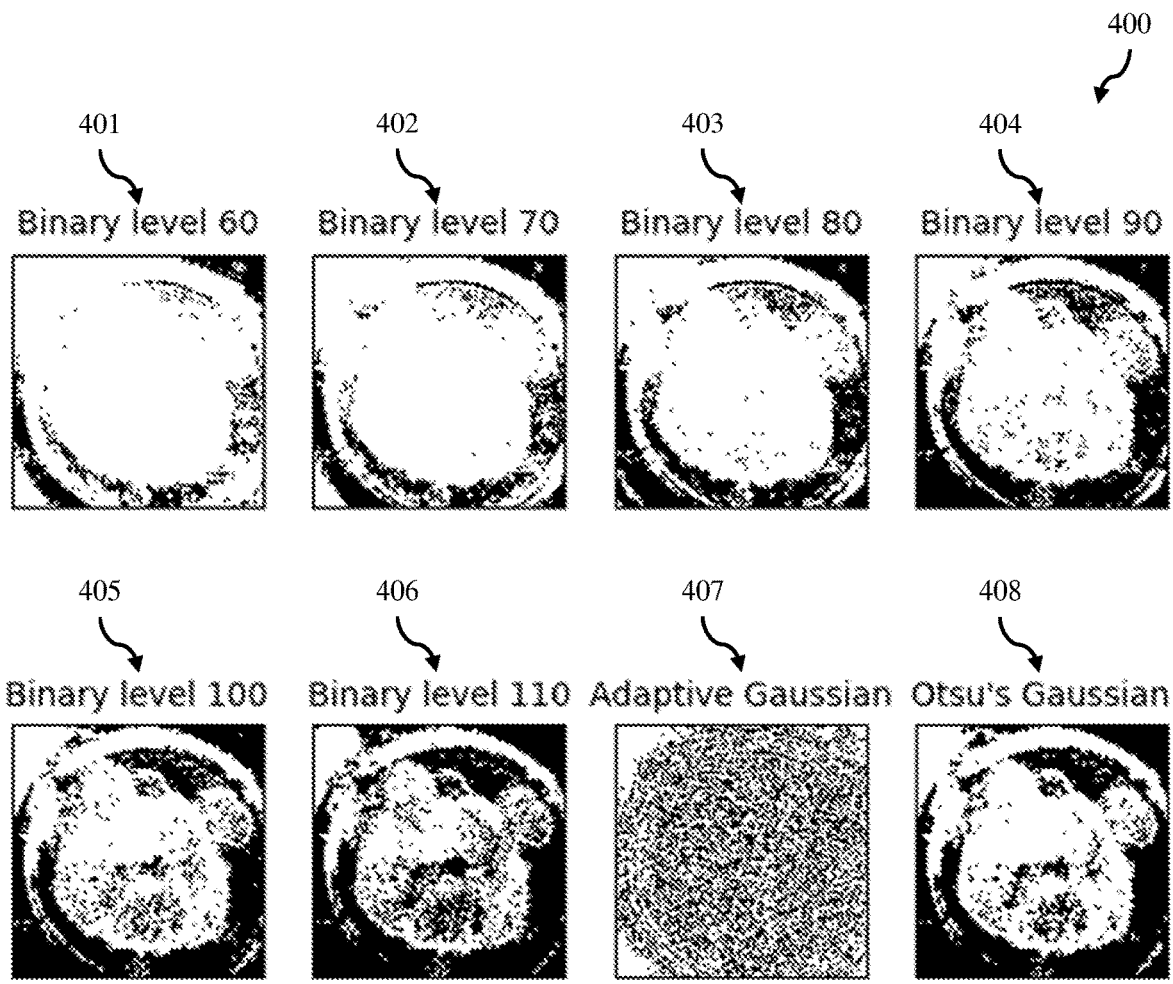
FIG. 4 is schematic diagram of binary thresholding for boundary-finding on images of human embryos according to an embodiment.
Figure 5:
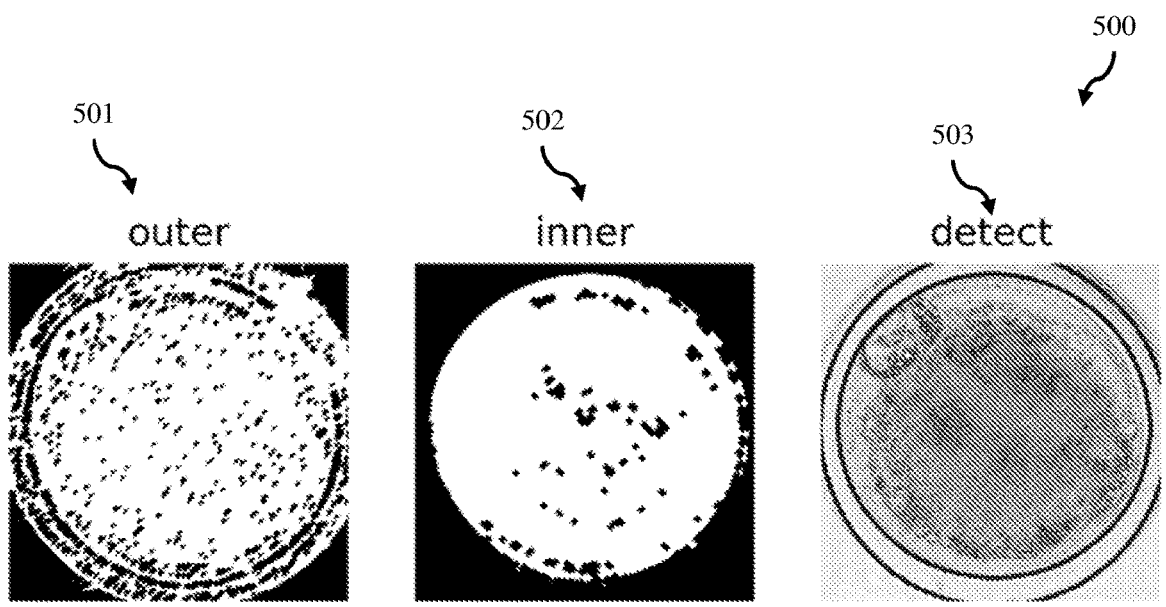
FIG. 5 is schematic diagram of a boundary-finding method on images of human embryos according to an embodiment

FIG. 4 is schematic diagram of binary thresholding 400 for boundary-finding on images of human embryos according to an embodiment. FIG. 4 shows 8 binary thresholds applied to the same image, namely levels 60, 70, 80, 90 100, 110 (images 401, 402, 403, 404, 405, 406, respectively), adaptive Gaussian 407 and Otsu's Gaussian 408. FIG. 5 is schematic diagram of a boundary-finding method 500 on an image of human embryo according to an embodiment. The first panel shows outer boundary 501, inner boundary 502, and the image with detected inner (and outer boundaries 503. The inner boundary 502 may approximately correspond to the IZC boundary, and the outer boundary 501 may approximately correspond to the outer edge of the Zona Pellucida region.

Figure 6A:
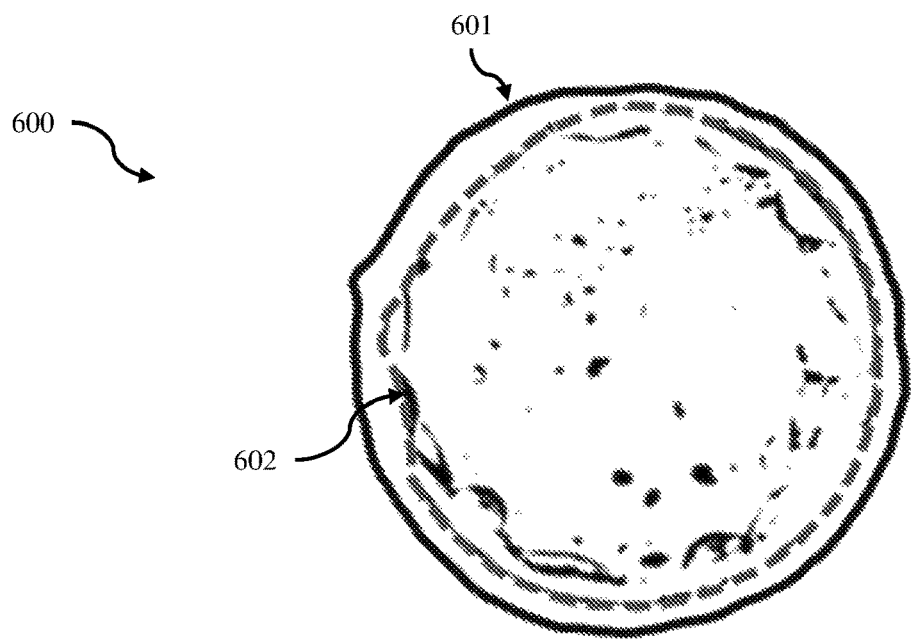
FIG. 6A is an example of the use of a Geometrical Active Contour (GAC) model as applied to a fixed region of an image for image segmentation according to an embodiment.
Figure 6B:
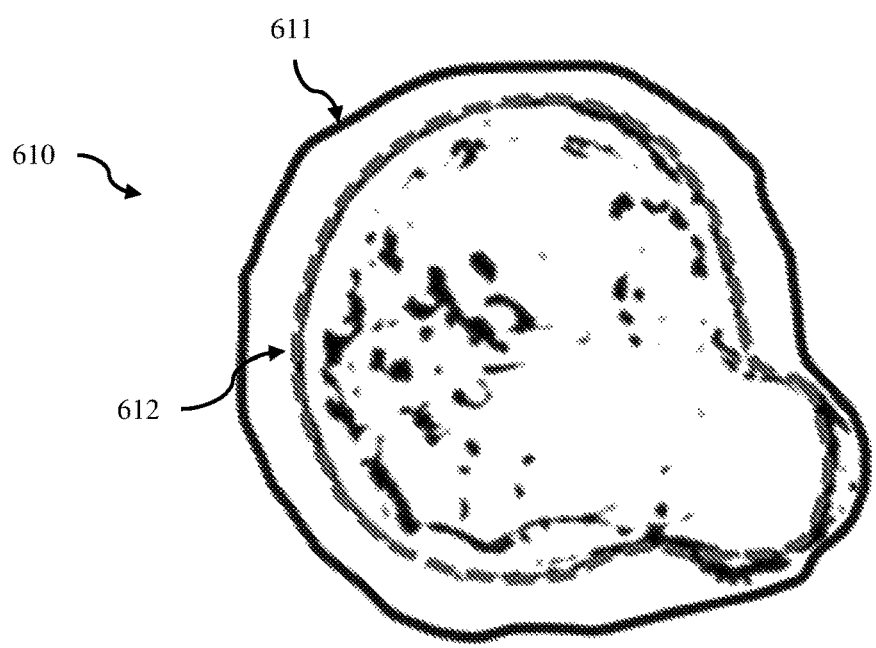
FIG. 6B is an example of the use of a morphological snake as applied to a fixed region of an image for image segmentation according.

FIG. 6A is an example of the use of a Geometrical Active Contour (GAC) model as applied to a fixed region of an image 600 for image segmentation according to an embodiment. The blue solid line 601 is the outer boundary of the Zona Pellucida region and the dashed green line 602 denotes the inner boundary defining the edge of the Zona Pellucida region and the cytoplasmic (IntraZonal Cavity or IZC) region. FIG. 6B is an example of the use of a morphological snake as applied to a fixed region of an image for image segmentation. Again the blue solid line 611 is the outer boundary of the Zona Pellucida region and the dashed green line 612 denotes the inner boundary defining the edge of the Zona Pellucida region and the cytoplasmic (inner) region. In this second image the boundary 612 (defining the cytoplasmic IntraZonal Cavity region) has an irregular shape with a bump or projecting portion in the lower right hand quadrant.

In another embodiment an object detector uses an object detection model which is trained to estimate a bounding box which contains the embryo. The goal of object detection is to identify the largest bounding box that contains all of the pixels associated with that object. This requires the model to both model the location of an object and a category/label (i.e. what's in the box) and thus detection models typically contain both an object classifier head and a bounding box regression head.

One approach is Region-Convolutional Neural Net (or R-CNN) which uses an expensive search process is applied to search for image patch proposals (potential bounding boxes). These bounding boxes are then used to crop the regions of the image of interest. The cropped images are then run through a classifying model to classify the contents of the image region. This process is complicated and computationally expensive. An alternative is Fast-CNN which uses a CNN that proposed feature regions rather a search for image patch proposals. This model uses a CNN to estimate a fixed number of candidate boxes, typically set to be between 100 and 2000. An even faster alternative approach is Faster-RCNN which uses anchor boxes to limit the search space of required boxes. By default, a standard set of 9 anchor boxes (each of different size) is used. Faster-RCNN. This uses a small network which jointly learns to predict the feature regions of interest, and this can speed up the runtime compared to R-CNN or Fast-CNN as expensive region search can be replaced.

For every feature activation coming out of the back one model is considered anchor point (Red in the image below). For every anchor point, the 9 (or more, or less, depending on problem) anchor boxes are generated. The anchor boxes correspond to common object sizes in the training dataset. As there are multiple anchor points with multiple anchor boxes, this results in 10s of thousands of region proposals. The proposals are then filtered via a process called Non-Maximal Suppression (NMS) that selects the largest box that has confident smaller boxes contained within it. This ensures that there is only 1 box for each object. As the NMS is relies on the confidence of each bounding box prediction, a threshold must be set for when to consider objects as part of the same object instance. As the anchor boxes will not fit the objects perfectly, the job of the regression head is to predict the offsets to these anchor boxes which morph them into the best fitting bounding box.

The detector can also specialise and only estimate boxes for a subset of objects e.g. only people for pedestrian detectors. Object categories that are not of interest are encoded into the 0-class which corresponds with the background class. During training, patches/boxes for the background class are usually sampled at random from image regions which contain no bounding box information. This step allows the model to become invariant to those undesirable objects e.g. it can learn to ignore them rather than classifying them incorrectly. Bounding boxes are usually represented in two different formats: The most common is (x1, y1, x2, y2) where the point p1=(x1, y1) is the top left hand corner of the box and p2=(x2, y2) is the bottom right hand side. The other common box format is (cx, cy, height, width), where the bounding box/rectangle is encoded as a centre point of the box (cx, cy) and the box size (height, width). Different detection methods will use different encodings/formats depending on the task and situation.

The regression head may be trained using a L1 loss and the classification head may be trained using a CrossEntropy loss. An objectness loss may also be used (is this background or an object) as well The final loss is computed as the sum of these losses. The individual losses may also be weighted such as:

$$loss = \lambda_1 \text{regression\_loss} + \lambda_2 \text{classification\_loss} + \lambda_3 \text{objectness\_loss} \quad (1)$$

In one embodiment, an embryo detection model based upon Faster-RNN was used. In this embodiment approximately 2000 images were hand labelled with the ground truth bounding boxes. The boxes were labelled such that the full embryo, including the Zona Pellucida region, were inside the bounding box. In the cases of there being more than one embryo present, a.k.a Double transfer, both embryos were labelled in order to allow the model to differentiate between double transfer and single transfer. As it is impossible to reconcile which embryo is which in a double transfer, then the model was configured to raise an error to the use if a double transfer was detected. Models with multiple 'lobes' are labelled as being a single embryo.

As an alternative to GAC segmentation, semantic segmentation may be used. Semantic Segmentation is the task of trying to predict a category or label for every pixel. Tasks like semantic segmentation are referred to as pixel-wise dense prediction tasks as an output is required for every input pixel. Semantic segmentation models are setup differently to standard models as they require a full image output. Typically, a semantic segmentation (or any dense prediction model) will have an encoding module and a decoding module. The encoding module is responsible for create a low-dimensional representation of the image (sometimes called a feature representation). This feature representation is then decoded into the final output image via the decoding module. During training, the predicted label map (for semantic segmentation) is then compared against the ground truth label maps that assign a category to each pixel, and the loss is computed. The standard loss function for Segmentation models is either BinaryCrossEntropy, standard Crossentopy loss (depending on if the problem is multi-class or not). These implementations are identical to their image classification cousins, except that the loss is applied pixel wise (across the image channel dimension of the tensor).

The Fully Convolutional Network (FCN) style architecture is commonly used in the field for generic semantic segmentation tasks. In this architecture, a pretrained model (such as a ResNet) is first used to encode a low resolution image (at approx ⅟₃₂ of the original resolution, but can be ⅛ if dilated convolutions are used). This low resolution label map is then up-sampled to the original image resolution and the loss is computed. The intuition behind predicted a low resolution label map, is that semantic segmentation masks are very low frequency and do not need all the extra parameters of a larger decoder. More complicated versions of this model exist, which use multi-stage upsampling to improve segmentation results. Simply stated, the loss is computed at multiple resolutions in a progressive manner to refine the predictions at each scale.

One down side of this type of model, is that if the input data is high resolution, or contains high frequency information (i.e. smaller/thinner objects), the low-resolution label map will fail to capture these smaller structures (especially when the encoding model does not use dilated convolutions). In a standard encoder/Convolutional Neural Network, the input image/image features are progressively downsampled as the model gets deeper. However, as the image/features are downsampled key high frequency details can be lost. Thus to address this, an alternative U-Net architecture may be used that instead uses skip connections between the symmetric components of the encoder and decoder. Simply put, every encoding block has a corresponding block in the decoder. The features at each stage are then passed to the decoder alongside the lowest resolution feature representation. For each of the decoding blocks, the input feature representation is upsampled to match the resolution of its corresponding encoding block. The feature representation from the encoding block and the upsampled lower resolution features are then concatenated and passed through a 2D convolution layer. By concatenating the features in this way, the decoder can learn to refine the inputs at each block, choosing which details to integrate (low-res details or high-res details) depending on its input.

Figure 6C:
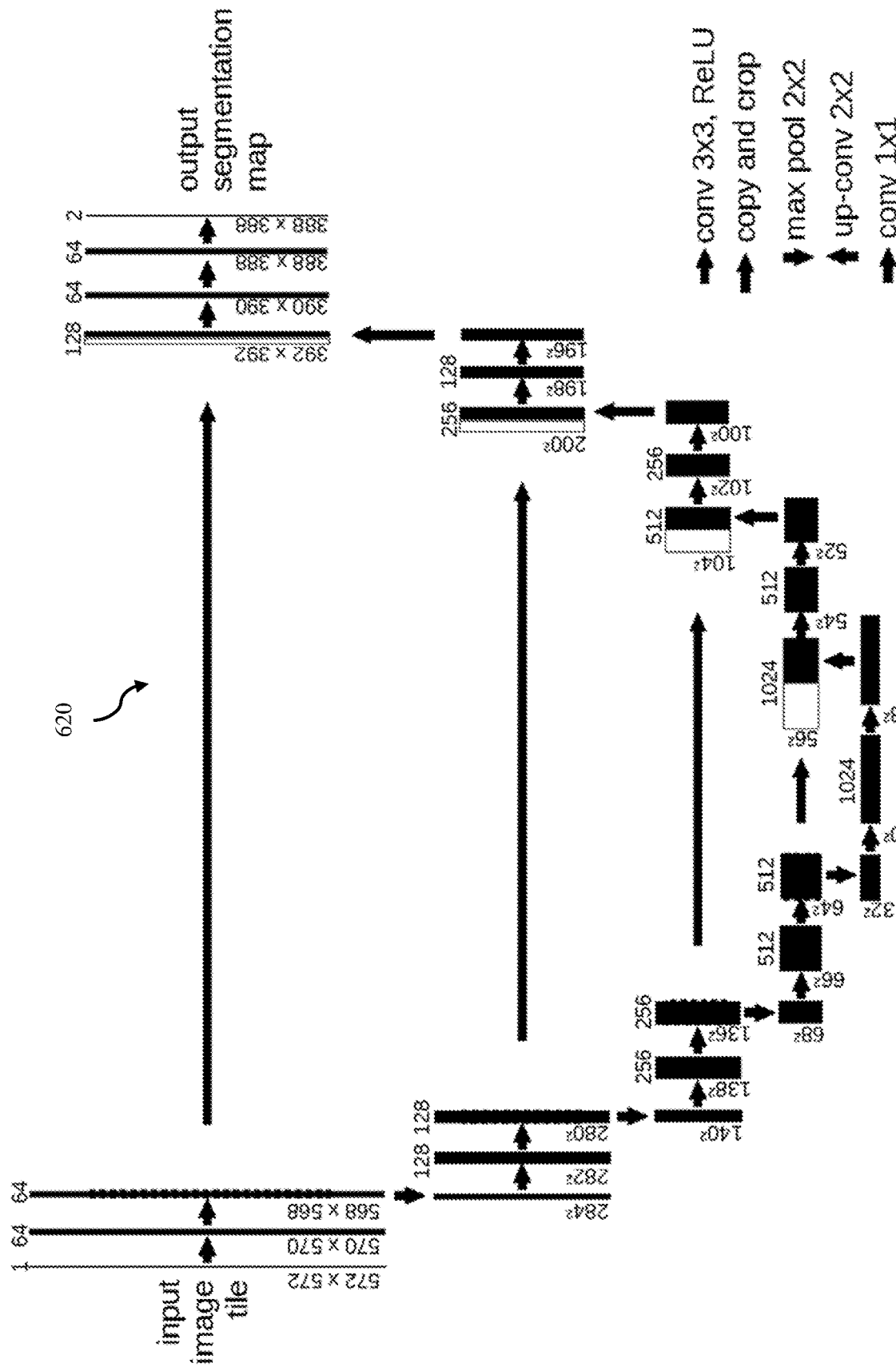
FIG. 6C is a schematic architecture diagram of a U-Net architecture for an semantic segmentation model according to an embodiment.

An example of a U-Net architecture 620 is shown in FIG. 6C. The main difference between FCN style models and U-Net style models is that in the FCN model, the encoder is responsible for predicting a low resolution label map that is then upsampled (possibly progressively). Whereas, the U-Net model does not have a fully complete label map prediction until the final layer. Ultimately, there do exist many variants of these models that trade off the differences between them (e.g. Hybrids). U-net architectures may also use pre-trained weights, such as ResNet-18 or ResNet-50, for use in cases where there is insufficient data to train models from scratch.

Figure 6D:
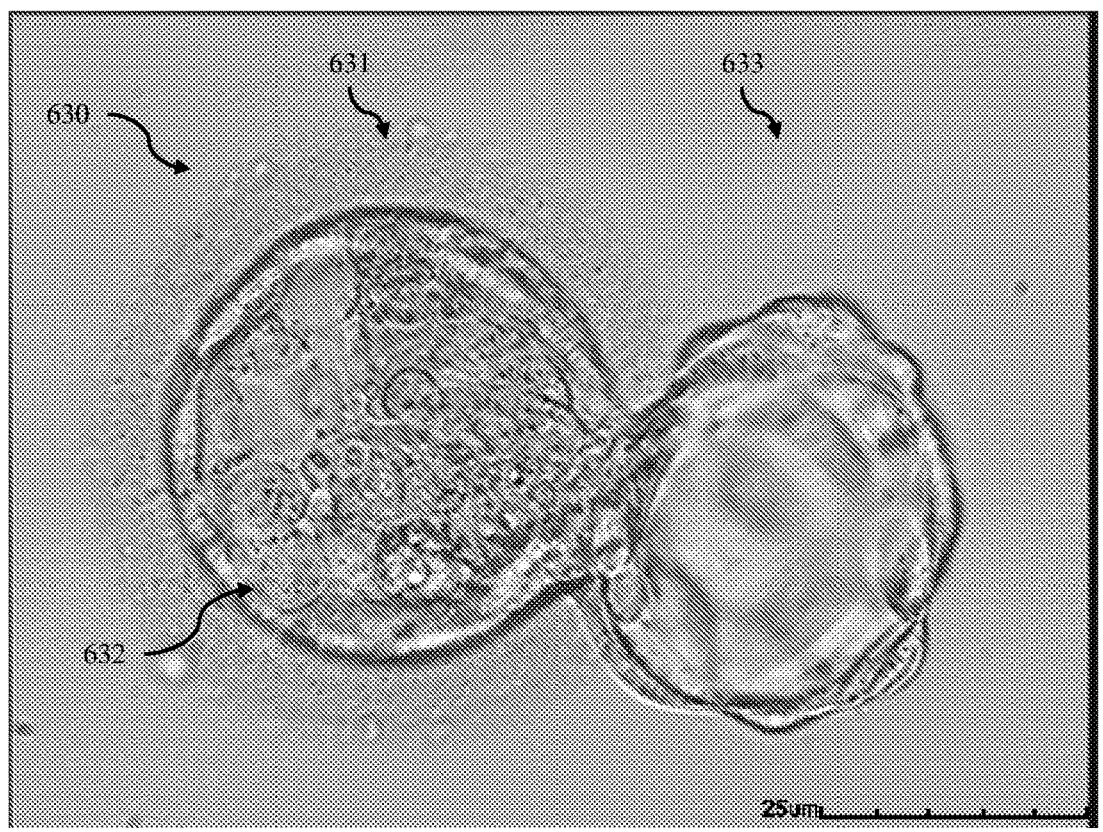
FIG. 6D is an image of a day 5 embryo.
Figure 6E:
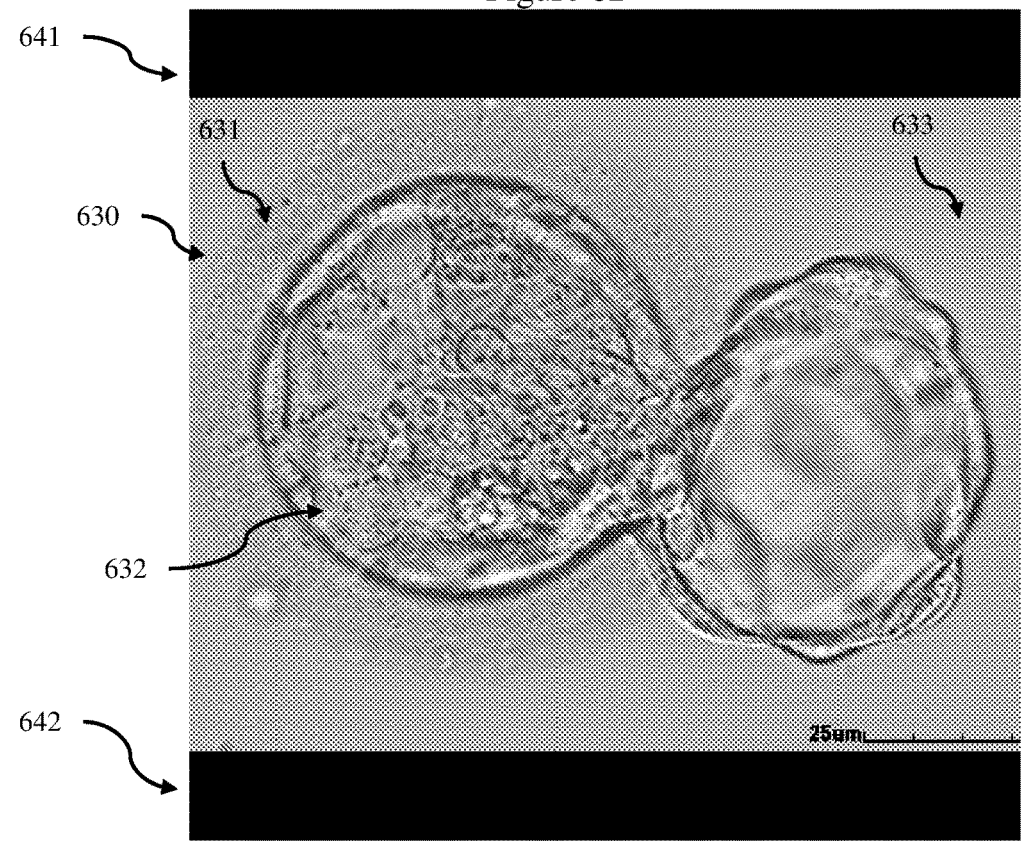
FIG. 6E is a padded version of FIG. 6D creating a square image.
Figure 6F:
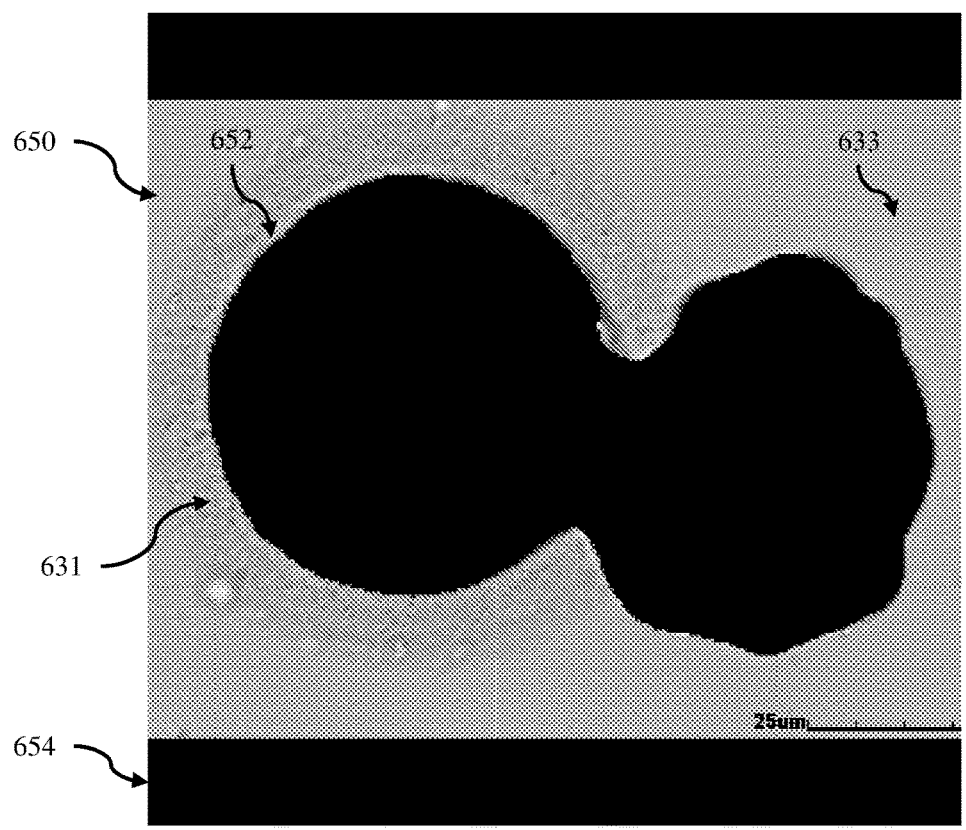
FIG. 6F shows a Zona Image based on FIG. 6E in which the IZC is masked according to an embodiment.
Figure 6G:
FIG. 6G shows a IZC image based on FIG. 6E in which the Zona Pellucida and background is masked according to an embodiment.

In some embodiments segmentation was performed using U-Net architecture with pre-trained ResNet-50 encoder trained using BinaryCrossEntropy to identify the Zona Pellucida region and the IntraZonal Cavity region. This U-Net architecture based segmenter generally outperformed active contour based segmentation, particularly on poorer quality images. FIGS. 6D to 6F illustrate segmentation according to an embodiment. FIG. 6D is an image of a day 5 embryo 630 comprising a Zona Pellucida region 631 surrounding the IntraZonal Cavity (IZC, 632). In this embodiment the embryo is starting to hatch with the ISZ emerging (hatching) from the Zona Pellucida. The embryo is surrounded by background pixels 633. FIG. 6E is a padded image 640 created from FIG. 6D by adding padding pixels 641 642 to create a square image more easily processed by the deep learning methods. FIG. 6F shows a Zona Image 650 in which the IZC is masked 652 to leave the Zona Pellucida 631 and background pixels 633, and FIG. 6G shows a IZC image 660 in which the Zona Pellucida and background is masked 661 leaving only the IZC region 632. Once segmented, images sets could be generated in which all regions other than a desired region were masked. AI Models could then be trained on these specific image sets. That is AI models could be separated into two groups: first, those that included additional image segmentation, and second those that required the entire unsegmented image. Models that were trained on images that masked the IZC, exposing the zona region, were denoted as Zona models. Models that were trained on images that masked the Zona (denoted IZC models), and models that were trained on full-embryo images (i.e. second group), were also considered in training.

In one embodiment, to ensure uniqueness of each image, so that copies of records do not bias the results, the name of the new image is set equal to the hash of the original image contents, as a png (lossless) file. When run, the data parser will output images in a multi-threaded way, for any images that do not already exist in the output directory (which, if it doesn't exist, will create it), so if it is a lengthy process, it can be restarted from the same point even if it is interrupted. The data preparation step may also include processing the metadata to remove images associated with inconsistent or contradictory records, and identify any mistaken clinical records. For example a script may be run on a spreadsheet to conform the metadata into a predefined format. This ensures the data used to generate and train the models is of high quality, and has uniform characteristics (e.g. size, colour, scale etc.).

In some embodiments the data is cleaned by identifying images with likely incorrect pregnancy outcome labels (i.e. mis-labelled data), and excluding or re-labelling the identified images. In one embodiment this is performed by estimating the likelihood that a pregnancy outcome label associated with an image is incorrect and comparing the likelihood against a threshold value. If the likelihood exceeds the threshold value then the image is excluded or relabelled. Estimating the likelihood a pregnancy outcome label is incorrect may be performed by using a plurality of AI classification models and a k-fold cross validation method. In this approach the images are split into k mutually exclusive validation datasets. Each of the plurality of AI classifications model is trained on k-1 validation datasets in combination and then used to classify images in the remaining validation dataset. The likelihood is then determined based on the number of AI classification models which misclassify the pregnancy outcome label of an image. In some embodiments a deep learning model may further be used to learn the likelihood value.

Once the data is suitably pre-processed it can then be used to train one or more AI models. In one embodiment the AI model is a deep learning model trained on a set of Zona Pellucida images in all regions of the images except the Zona Pellucida are masked during pre-processing. In one embodiment multiple AI models are trained and then combined using an ensemble or distillation method. The AI models may be one or more deep learning models and/or one or more computer vision (CV) models. The deep learning models may be trained on full embryo images, Zona images or IZC images. The computer vision (CV) models may be generated using a machine learning method using a set feature descriptors calculated from each image Each of the individual models are configured to estimate an embryo viability score of an embryo in an image, and the AI model combines selected models to produce an overall embryo viability score that is returned by the AI model.

Training is performed using randomised datasets. Sets of complex image data, can suffer from uneven distribution, especially if the data set is smaller than around 10,000 images, where exemplars of key viable or non-viable embryos are not distributed evenly through the set. Therefore, several (e.g. 20) randomizations of the data are considered at one time, and then split into the training, validation and blind test subsets defined below. All randomizations are used for a single training example, to gauge which exhibits the best distribution for training. As a corollary, it is also beneficial to ensure that the ratio between the number of viable and non-viable embryos is the same across every subset. Embryo images are quite diverse, and thus ensuring even distribution of images across test and training sets can be used to improve performance. Thus after performing a randomisation the ratio of images with a viable classification to images with a non-viable classification in each of the training set, validation set and blind validation set is calculated and tested to ensure that the ratios are similar. For example this may include testing if the range of the ratios is less than a threshold value, or within some variance taking into account the number of images. If the ranges are not similar then the randomisation is discarded and a new randomisation is generated and tested until a randomisation is obtained in which the ratios are similar. More generally if the outcome is a n-ary outcome having n states then after randomisation is performed the calculation step may comprise calculating the frequency of each of the n-ary outcome states in each of the training set, validation set and blind validation set, and testing that the frequencies are similar, and if the frequencies are not similar then discarding the allocation and repeating the randomisation until a randomisation is obtained in which the frequencies are similar.

Training further comprises performing a plurality of training-validation cycles. In each train-validate cycle each randomization of the total useable dataset is split into typically 3 separate datasets known as the training, validation and blind validation datasets. In some variants more than 3 could be used, for example the validation and blind validation datasets could be stratified into multiple sub test sets of varying difficulty.

The first set is the training dataset and comprises at least 60% and preferably 70-80% of images. These images are used by deep learning models and computer vision models to create an embryo viability assessment model to accurately identify viable embryos. The second set is the Validation dataset, which is typically around (or at least) 10% of images: This dataset is used to validate or test the accuracy of the model created using the training dataset. Even though these images are independent of the training dataset used to create the model, the validation dataset still has a small positive bias in accuracy because it is used to monitor and optimize the progress of the model training. Hence, training tends to be targeted towards models that maximize the accuracy of this particular validation dataset, which may not necessarily be the best model when applied more generally to other embryo images. The third dataset is the Blind validation dataset which is typically around 10-20% of the images. To address the positive bias with the validation dataset described above, a third blind validation dataset is used to conduct a final unbiased accuracy assessment of the final model. This validation occurs at the end of the modelling and validation process, when a final model has been created and selected. It is important to ensure that the final model's accuracy is relatively consistent with the validation dataset to ensure that the model is generalizable to all embryos images. The accuracy of the validation dataset will likely be higher than the blind validation dataset for the reasons discussed above. Results of the blind validation dataset are a more reliable measure of the accuracy of the model.

In some embodiments pre-processing the data further comprises augmenting images, in which a change is made to the image. This may be performed prior to training, or during training (i.e. on the fly). Augmentation may comprise directly augmenting (altering) and image or by making a copy of an image with a small change. Any number of augmentations may be performed with varying amounts of 90 degree rotations of the image, mirror flip, a non-90 degree rotation where a diagonal border is filled in to match a background colour, image blurring, adjusting an image contrast using an intensity histogram, and applying one or more small random translations in both the horizontal and/or vertical direction, random rotations, adding JPEG (or compression) noise, random image resizing, random hue jitter, random brightness jitter, contrast limited adaptive histogram equalization, random flip/mirror, image sharpening, image embossing, random brightness and contrast, RGB colour shift, random hue and saturation, channel shuffle: swap RGB to BGR or RBG or other, coarse dropout, motion blur, median blur, Gaussian blur, random shift-scale-rotate (i.e. all three combined). The same set of augmented images may be used for multiple training-validation cycles, or new augmentations may be generated on the fly during each cycle. An additional augmentation used for CV model training is the alteration of the 'seed' of the random number generator for extracting feature descriptors. The techniques for obtaining computer vision descriptors contain an element of randomness in extracting a sample of features. This random number can be altered and included among the augmentations to provide a more robust training for CV models.

Computer vision models rely on identifying key features of the image and expressing them in terms of descriptors. These descriptors may encode qualities such as pixel variation, gray level, roughness of texture, fixed corner points or orientation of image gradients, which are implemented in the OpenCV or similar libraries. By selection on such feature to search for in each image, a model can be built by finding which arrangement of the features is a good indicator for embryo viability. This procedure is best carried out by machine learning processes such as Random Forest or Support Vector Machines, which are able to separate the images in terms of their descriptions from the computer vision analysis.

A range of computer vision descriptors are used, encompassing both small and large scale features, which are combined with traditional machine learning methods to produce "CV models" for embryo selection. These may optionally be later combined with deep learning (DL) models, for example into an Ensemble model or used in distillation to train a student model. Suitable computer vision image descriptors include:

Zona-Pellucida through Hough transformation: finds inner and outer ellipses to approximate the Zona Pellucida and IntraZonal Cavity split, and records the mean and difference in radii as features;

Gray-Level Co-Occurrence Matrix (GLCM) Texture Analysis: detects roughness of different regions by comparing neighbouring pixels in the region. The sample feature descriptors used are: angular second moment (ASM), homogeneity, correlation, contrast and entropy. The selection of the region is obtained by randomly sampling a given number of square sub-regions of the image, of a given size, and records the results of each of the five descriptors for each region as the total set of features;

Histogram of Oriented Gradients (HOG): detects objects and features using scale-invariant feature transform descriptors and shape contexts. This method has precedence for being used in embryology and other medical imaging, but does not itself constitute a machine learning model;

Oriented Features from Accelerated Segment Test (FAST) and Rotated Binary Robust Independent Elementary Features (BRIEF) (ORB): an industry standard alternative to SIFT and SURF features, which relies on a FAST key-point detector (specific pixel) and BRIEF descriptor combination, and which has been modified to include rotation invariance;

Binary Robust Invariant Scalable Key-points (BRISK): a FAST-based detector in combination with an assembly of intensity comparisons of pixels, which is achieved by sampling each neighbourhood around a feature specified at a key-point;

Maximally Stable Extremal Regions (MSER): a local morphological feature detection algorithm, through extracting covariant regions, which are stable connected components related to one or more gray-level sets extracted from the image.

Good Features To Track (GFTT): a feature detector that uses an adaptive window size to detect textures of corners, identified using Harris Corner Detection or Shi-Tomasi Corner Detection, and extracting points the exhibit a high standard deviation in their spatial intensity profile.

Figure 7:
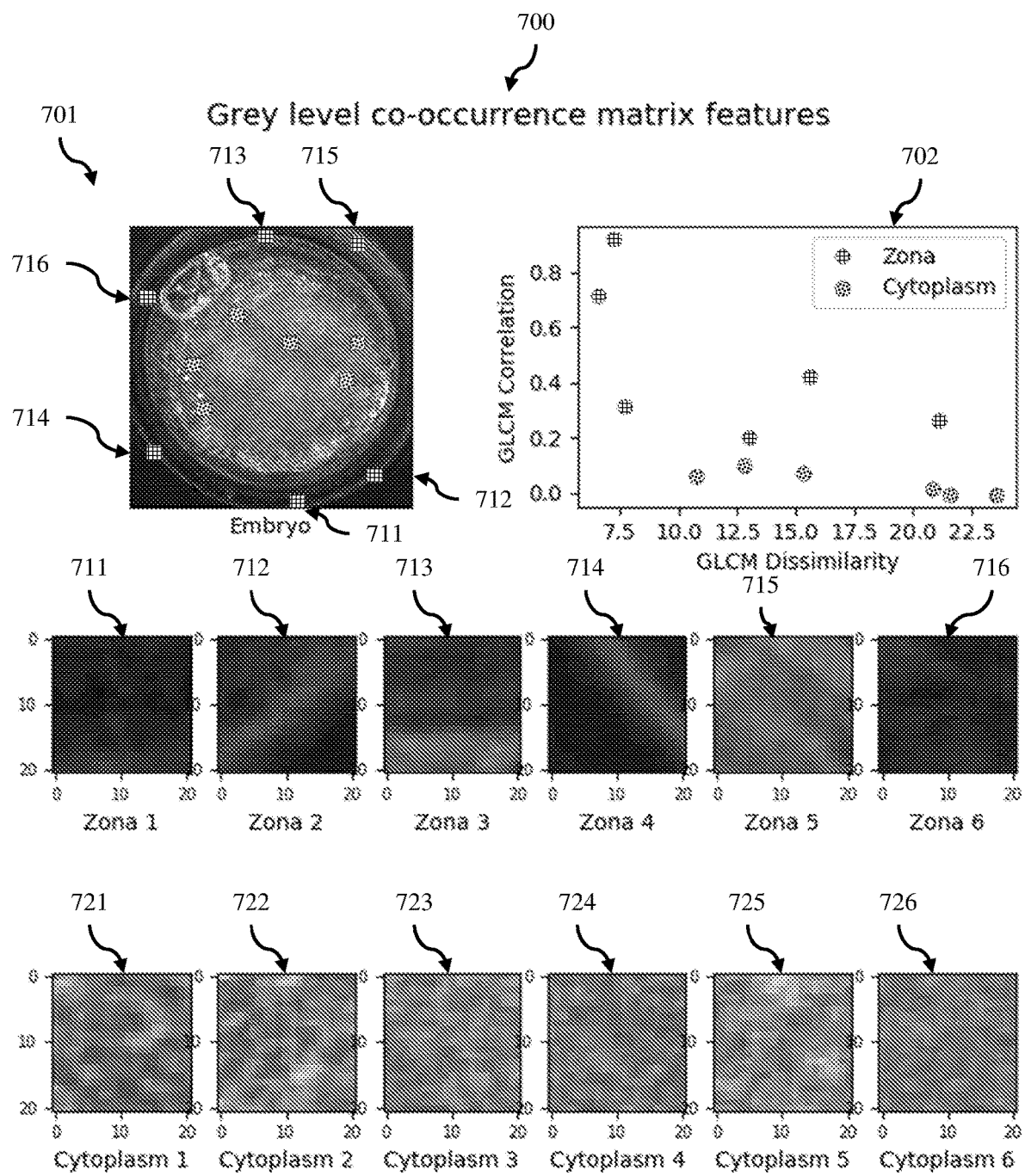
FIG. 7 is a plot of a Gray Level Co-occurrence Matrix (GLCM) showing GLCM correlation of sample feature descriptors: ASM, homogeneity, correlation, contrast and entropy, calculated on a set of six Zona Pellucida regions and six cytoplasm regions according to an embodiment associated.

FIG. 7 is a plot 700 of a Gray Level Co-occurrence Matrix (GLCM) showing GLCM correlation of sample feature descriptors 702: ASM, homogeneity, correlation, contrast and entropy, calculated on a set of six Zona Pellucida regions (labelled 711 to 716; cross hatch) and six cytoplasm/IZC regions (labelled 721 to 726; dotted) in image 701.

A computer vision (CV) model is constructed by the following method. One (or more) of the computer vision image descriptors techniques listed above is selected, and the features are extracted from all of the images in the training dataset. These features are arranged into a combined array, and then supplied to a KMeans unsupervised clustering algorithm, this array is called the Codebook, for a 'bag of visual words'. The number of clusters is a free parameter of the model. The clustered features from this point on represent the 'custom features' that are used, through whichever combination of algorithms, to which each individual image in the validation or test set will be compared. Each image has features extracted and is clustered individually. For a given image with clustered features, the 'distance' (in feature-space) to each of the clusters in the codebook is measured using a KDTree query algorithm, which gives the closest clustered feature. The results from the tree query can then be represented as a histogram, showing the frequency at which each feature occurs in that image. Finally, the question of whether a particular combination of these features corresponds to a measure of embryo viability needs to be assessed, using machine learning. Here, the histogram and the ground-truth outcomes are used to carry out supervised learning. The methods used to obtain the final selection model include Random Forest or Support Vector Machine (SVM).

A plurality of deep learning models may also be generated. Deep Learning models are based on neural network methods, typically convolutional neural network (CNN) that consist of a plurality of connected layers, with each layer of 'neurons' containing a non-linear activation function, such as a 'rectifier', 'sigmoid' etc. Contrasting with feature based methods (i.e. CV models), Deep Learning and neural networks instead 'learn' features rather than relying on hand designed feature descriptors. This allows them to learn 'feature representations' that are tailored to the desired task. These methods are suitable for image analysis, as they are able to pick up both small details and overall morphological shapes in order to arrive at an overall classification A variety of deep learning models are available each with different architectures (i.e. different number of layers and connections between layers) such as residual networks (e.g. ResNet-18, ResNet-50 and ResNet-101), densely connected networks (e.g. DenseNet-121 and DenseNet-161), and other variations (e.g. InceptionV4 and Inception-ResNetV2). Deep Learning models may be assessed based on stabilisation (how stable the accuracy value was on the validation set over the training process) transferability (how well the accuracy on the training data correlated with the accuracy on the validation set) and prediction accuracy (which models provided the best validation accuracy, for both viable and non-viable embryos, the total combined accuracy, and the balanced accuracy, defined as the weighted average accuracy across both class types of embryos). Training involves trying different combinations of model parameters and hyper-parameters, including input image resolution, choice of optimizer, learning rate value and scheduling, momentum value, dropout, and initialization of the weights (pre-training). A loss function may be defined to assess performing of a model, and during training a Deep Learning model is optimised by varying learning rates to drive the update mechanism for the network's weight parameters to minimize an objective/loss function.

Deep learning models may be implemented using a variety of libraries and software languages. In one embodiment, the PyTorch library is used to implement neural networks in the language of python. The library Pytorch additionally allows tensors to be created that utilize Hardware (GPU, TPU) acceleration, and includes modules for building multiple layers for neural networks. While deep learning is one of the most powerful techniques for image classification, it can be improved by providing guidance through the use of segmentation or augmentation described above. The use of segmentation prior to deep learning was found to have a significant effect on the performance of the deep learning method, and assisted in generating contrasting models. Thus preferably at least some deep learning models were trained on segmented images such images in which the Zona Pellucida has been identified, or the image is masked to hide all regions except the Zona Pellucida region. In some embodiments the plurality of deep learning models includes at least one model trained on segmented images, and one model trained on images not subject to segmentation. Similarly augmentation was important for generating robust models.

The effectiveness of an approach is determined by the architecture of the Deep Neural Network (DNN). However, unlike the feature descriptor methods, the DNN learns the features itself throughout the convolutional layers, before employing a classifier. That is, without adding in proposed features by hand, the DNN can be used to check existing practices in the literature, as well as developing previously unguessed descriptors, especially those that are difficult for the human eye to detect and measure.

The architecture of the DNN is constrained by the size of images as input, the hidden layers, which have dimensions of the tensors describing the DNN, and a linear classifier, with the number of class labels as output. Most architectures employ a number of down-sampling ratios, with small (3×3 pixel) filters to capture notion of left/right, up-down and centre. Stacks of a) Convolutional 2d layers, b) Rectified Linear Units (ReLU), and c) Max Pooling layers allow the number of parameters through the DNN to remain tractable, while allowing the filters to pass over the high level (topological) features of an image, mapping them onto the intermediate and finally microscopic features embedded in the image. The top layer typically includes one or more fully-connected neural network layers, which act as a classifier, similar to SVM. Typically, a Softmax layer is used to normalize the resulting tensor as containing probabilities after the fully connected classifier. Therefore, the output of the model is a list of probabilities that the image is either non-viable or viable.

Figure 8:
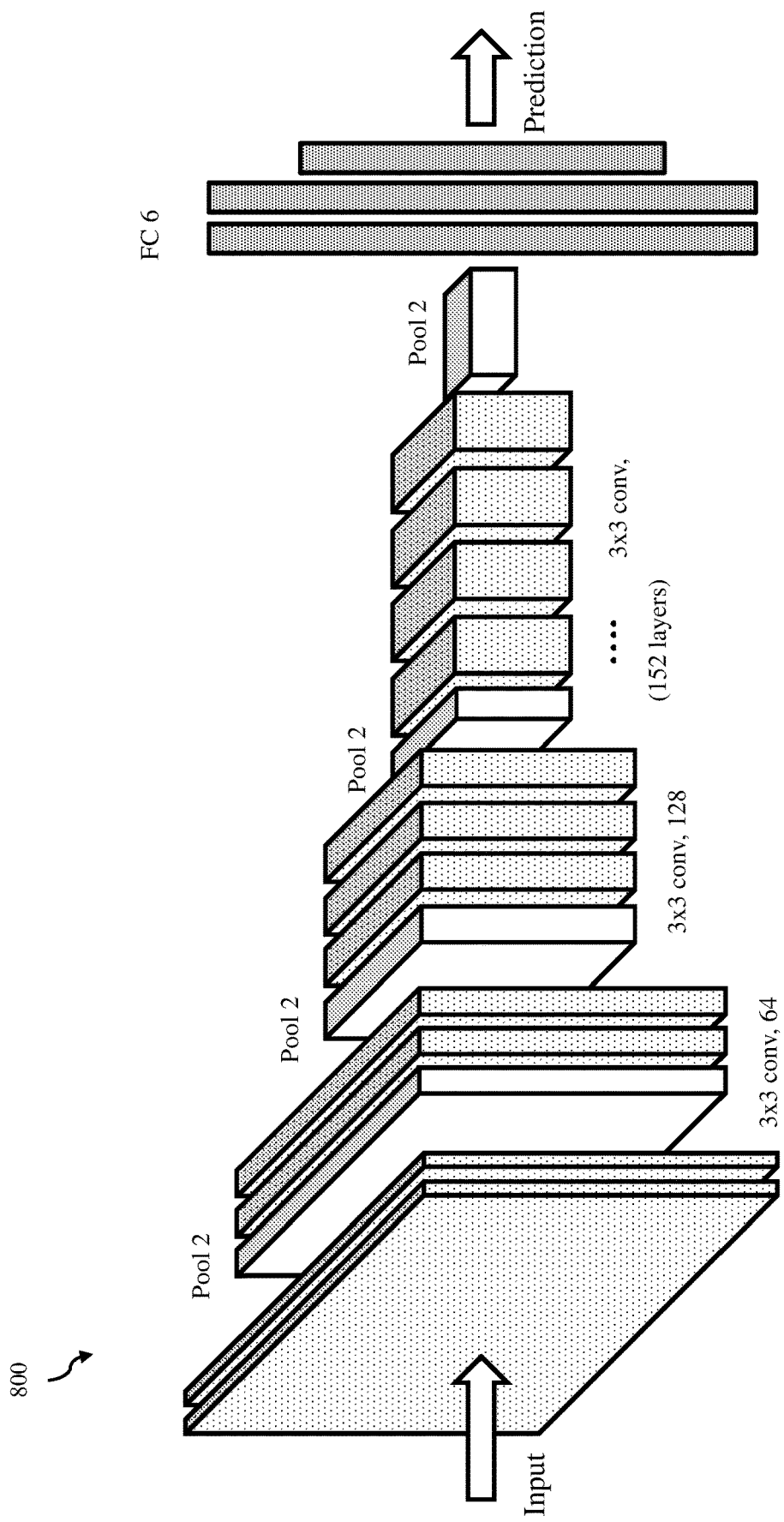
FIG. 8 is schematic architecture diagram of a deep learning method, including convolutional layers, which transform the input image to a prediction, after training, according to an embodiment.

FIG. 8 is schematic architecture diagram of a deep learning method, including convolutional layers, which transform the input image to a prediction, after training, according to an embodiment. FIG. 8 shows a series of layers based on a RESNET 152 architecture according to an embodiment. The components are annotated as follows. "CONV" indicates a convolutional 2D layer, which computes cross-correlations of the input from the layer below. Each element or neuron within the convolutional layer processes the input from its receptive field only, e.g. 3×3 or 7×7 pixels. This reduces the number of learnable parameters required to describe the layer, and allows deeper neural networks to be formed than those constructed from fully-connected layers where every neuron is connected to every other neuron in the subsequent layer, which is highly memory intensive and prone to overfitting. Convolutional layers are also spatial translation invariant, which is useful for processing images where the subject matter cannot be guaranteed to be precisely centred. "POOL" refers the max pooling layers, which is a down-sampling method whereby only representative neuron weights are selected within a given region, to reduce the complexity of the network and also reduce overfitting. For example, for weights within a 4×4 square region of a convolutional layer, the maximum value of each 2×2 corner block is computed, and these representative values are then used to reduce the size of the square region to 2×2 in dimension. RELU indicates the use of rectified linear units, which act as a nonlinear activation function. As a common example, the ramp function takes the following form for an input x from a given neuron, and is analogous to the activation of neurons in biology:

$$f(x)=\max(0,x) \quad (2)$$

The final layers at the end of the network, after the input has passed through all of the convolutional layers, is typically a fully connected (FC) layer, which acts as a classifier. This layer takes the final input and outputs an array of the same number of dimensions as the classification categories. For two categories, e.g. 'viable Day 5 embryo' and 'non-viable Day 5 embryo', the final layer will output an array of length 2, which indicates the proportion that the input image contains features that align with each category respectively. A final softmax layer is often added, which transforms the final numbers in the output array to percentages that fit between 0 and 1, and both together add up to a total of 1, so that the final output can be interpreted as a confidence limit for the image to be classified in one of the categories.

One suitable DNN architecture is Resnet (https://ieeexplore.ieee.org/document/7780459) such as ResNet152, ResNet101, ResNet50 or ResNet-18. ResNet advanced the field significantly in 2016 by using an extremely large number of hidden layers, and introducing 'skip connections' also known as 'residual connections'. Only the difference from one layer to the next is calculated, which is more time-cost efficient, and if very little change is detected at a particular layer, that layer is skipped over, thus create a network that will very quickly tune itself to a combination of small and large features in the image. In particular ResNet-18, ResNet-50, ResNet-101, DenseNet-121 and DenseNet-161 generally outperformed the other architectures. Another suitable DNN architecture is DenseNet (https://ieeexplore.ieee.org/document/8099726), such as DenseNet161, DenseNet201, DenseNet169, DenseNet121. DenseNet is an extension of ResNet, where now every layer can skip over to any other layer, with the maximal number of skip connections. This architecture requires much more memory, and so is less efficient, but can exhibit improved performance over ResNet. With a large number of model parameters, it is also easy to overtrain/overfit. All model architectures are often combined with methods to control for this In particular DenseNet-121 and DenseNet-161. Another suitable DNN architecture is Inception (-ResNet) (https://www.aaai.org/ocs/index.php/AAAI/AAAI17/paper/viewPaper/14806), such as: InceptionV4, InceptionResNetV2. Inception represents a more complicated convolutional unit, whereby instead of simply using a fixed size filter (e.g. 3×3 pixels) as described in Section 3.2, several sized filters are calculated in parallel: (5×5, 3×3, 1×1 pixels), with weights that are free parameters, so that the neural network may prioritize which filter is most suitable at each layer in the DNN. An extension of this kind if architecture is to combine it with skip connects in the same way as ResNet, to create an Inception-ResNet. In particular ResNet-18, ResNet-50, ResNet-101, DenseNet-121 and DenseNet-161 generally outperformed the other architectures.

As discussed above both computer vision and deep learning methods are trained using a plurality of Train-Validate Cycles on pre-processed data. The Train-Validate cycle follows the following framework:

The training data is pre-processed and split into batches (the number of data in each batch is a free model parameter but controls how fast and how stably the algorithm learns). Augmentation may be performed prior to splitting or during training.

After each batch, the weights of the network are adjusted, and the running total accuracy so far is assessed. In some embodiment weights are updated during the batch for example using gradient accumulation. When all images have been assessed 1 Epoch has been carried out, the training set is shuffled (i.e. a new randomisation with the set is obtained), and the training starts again from the top, for the next epoch.

During training a number of epochs may be run, depending on the size of the data set, the complexity of the data and the complexity of the model being trained. An optimal number of epochs is typically in the range of 2 to 100, but may be more depending on the specific case.

After each epoch, the model is run on the validation set, without any training taking place, to provide a measure of the progress in how accurate the model is, and to guide the user whether more epochs should be run, or if more epochs will result in overtraining. The validation set guides the choice of the overall model parameters, or hyperparameters, and is therefore not a truly blind set. However, it is important that the distribution of images of the validation set is very similar to the ultimate blind test set that will be run after training.

In reporting the validation set results, augmentations may also be included for each image (all), or not (noaug). Furthermore, the augmentations for each image may be combined to provide a more robust final result for the image. Several combination/voting strategies may be used including: mean-confidence (taking the mean value of the inference of the model across all the augmentations), median-confidence, majority-mean-confidence (taking the majority viability assessment, and only providing the mean confidence of those that agree, and if no majority, take the mean), max-confidence, weighted average, majority-max-confidence, etc.

Another method used in the field of machine learning is transfer learning, where a previously trained model is used as the starting point to train a new model. This is also referred to as Pre-training. Pre-training is used extensively, which allows new models to be built rapidly. There are two kinds of pre-training. One embodiment of pre-training is ImageNet pre-training. Most model architectures are provided with a set of pre-trained weights, using the standard image database ImageNet. While it is not specific for medical images, and includes one thousand different types of objects, it provides a method for a model to have already learnt to identify shapes. The classifier of the thousand objects is completely removed, and a new classifier for viability replaces it. This kind of pre-training outperforms other initialization strategies. Another embodiment of pre-training is custom pre-training which uses a previously-trained embryo model, either from a study with a different set of outcomes, or on different images (PGS instead of viability, or randomly assigned outcomes). These models only provide a small benefit to the classification.

For non pre-trained models, or new layers added after pre-training such as the classifier, the weights need to be initialized. The initialization method can make a difference to the success of the training. All weights set to 0 or 1, for example, will perform very poorly. A uniform arrangement of random numbers, or a Gaussian distribution of random numbers, also represent commonly used options. These are also often combined with a normalization method, such as Xavier or Kaiming algorithms. This addresses an issue where nodes in the neural network can become 'trapped' in a certain state, by becoming saturated (close to 1), or dead (close to 0), where it is difficult to measure in which direction to adjust the weights associated with that particular neuron. This is especially prevalent when introducing a hyperbolic-tangent or a sigmoid function, and is addressed by the Xavier initialization.

In the Xavier initialization protocol, the neural network weights are randomized in such a way that the inputs of each layer to the activation function will not fall too close to either the saturated or dead extreme ends. The use of ReLU, however, is better behaved, and different initializations provide a smaller benefit, such as the Kaiming initialization. The Kaiming initialization is better suited to the case where ReLU is used as the neuron's non-linear activation profile. This achieves the same process as the Xavier initialization effectively.

In deep learning, a range of free parameters is used to optimize the model training on the validation set. One of the key parameters is the learning rate, which determines by how much the underlying neuron weights are adjusted after each batch. When training a selection model, overtraining, or overfitting the data should be avoided. This happens when the model contains too many parameters to fit, and essentially 'memorizes' the data, trading generalizability for accuracy on the training or validation sets. This is to be avoided, since the generalizability is the true measure of whether the model has correctly identified true underlying parameters that indicate embryo health, among the noise of the data, and not compromised this in order to fit the training set perfectly.

During the Validation and Test phases, success rates can sometimes drop suddenly due to overfitting during the Training phase. This can be ameliorated through a variety of tactics, including slowed or decaying learning rates (e.g. halve the learning rate every n epochs) or the use of CosineAnnealling, incorporating the aforementioned methods of tensor initialization or pre-training, and the addition of noise, such as Dropout layers, or Batch Normalization. Batch Normalisation is used to counteract vanishing or exploding gradients which improves the stability of training large models resulting in improved generalisation. Dropout regularization effectively simplifies the network by introducing a random chance to set all incoming weights zero within a rectifier's receptive range. By introducing noise, it effectively ensures the remaining rectifiers are correctly fitting to the representation of the data, without relying on over-specialization. This allows the DNN to generalize more effectively and become less sensitive to specific values of network weights. Similarly, Batch Normalization improves training stability of very deep neural networks, which allows for faster learning and better generalization by shifting the input weights to zero mean and unit variance as a precursor to the rectification stage.

In performing deep learning, the methodology for altering the neuron weights to achieve an acceptable classification includes the need to specify an optimization protocol. That is, for a given definition of 'accuracy' or 'loss' (discussed below) exactly how much the weights should be adjusted, and how the value of the learning rate should be used, has a number of techniques that need to be specified. Suitable optimisation techniques include Stochastic Gradient Descent (SGD) with momentum (and/or Nesterov accelerated gradients), Adaptive Gradient with Delta (Adadelta), Adaptive Moment Estimation (Adam), Root-Mean-Square Propagation (RMSProp), and Limited-Memory Broyden-Fletcher-Goldfarb-Shanno (L-BFGS) Algorithm. Of these, SGD based techniques generally outperformed other optimisation techniques. Typical learning rates for phase contrast microscope images of human embryos were between 0.01 to 0.0001. However the learning rate will depend upon batch size, which is dependent upon hardware capacity. For example larger GPUs allow larger batch sizes and higher learning rates.

Stochastic Gradient Descent (SGD) with momentum (and/or Nesterov accelerated gradients) represents the most simple and commonly used optimizer. Gradient descent algorithms typically compute the gradient (slope) of the effect of a given weight on the accuracy. While this is slow if it is required to calculate the gradient for the whole dataset to perform an update to the weights, stochastic gradient descent performs an update for each training image, one at a time. While this can result in fluctuations in the overall objective accuracy or loss achieved, it has a tendency to generalize better than other methods, as it is able to jump into new regions of the loss parameter landscape, and find new minimum loss functions. For a noisy loss landscape in difficult problems such as embryo selection, SGD performs well. SGD can have trouble navigating asymmetrical loss function surface curves that are more steep on one side than the other, this can be compensated for by adding a parameter called momentum. This helps accelerate SGD in the direction and dampens high fluctuations in the accuracy, by adding an extra fraction to the update of the weight, derived from the previous state. An extension of this method is to include the estimated position of the weight in the next state as well, and this extension is known as the Nesterov accelerated gradient.

Adaptive Gradient with Delta (Adadelta), is an algorithm for adapting the learning rate to the weights themselves, performing smaller updates for parameters that are frequently occurring, and larger updates for infrequently occurring features, and is well-suited to sparse data. While this can suddenly reduce the learning rate after a few epochs across the entire dataset, the addition of a delta parameter in order to restrict the window allowed for the accumulated past gradients, to some fixed size. This process makes a default learning rate redundant, however, and the freedom of an additional free parameter provides some control in finding the best overall selection model.

Adaptive Moment Estimation (Adam) stores exponentially decaying average of both past squared and non-squared gradients, incorporating them both into the weight update. This has the effect of providing 'friction' for the direction of the weight update, and is suitable for problems that have relatively shallow or flat loss minima, without strong fluctuations. In the embryo selection model, training with Adam has a tendency to perform well on the training set, but often overtrain, and is not as suitable as SGD with momentum.

Root-Mean-Square Propagation (RMSProp) is related to the adaptive gradient optimizers above, and almost identical to Adadelta, except that the update term to the weights divides the learning rate by an exponentially decaying average of the squared gradients.

Limited-Memory Broyden-Fletcher-Goldfarb-Shanno (L-BFGS) Algorithm. While computationally intensive, the L-BFGS algorithm that actually estimates the curvature of the loss landscape rather than other methods than attempt to compensate for this lack of estimation with additional terms. It has a tendency to outperform Adam when the data set is small, but doesn't necessarily outperform SGD in terms of speed and accuracy.

In addition to the above methods, it is also possible to include non-uniform learning rates. That is, the learning rate of the convolution layers can be specified to be much larger or smaller than the learning rate of the classifier. This is useful in the case of pre-trained models, where changes to the filters underneath the classifier should be kept more 'frozen', and the classifier be retrained, so that the pre-training is not undone by additional retraining.

While the optimizer specifies how to update the weights given a specific loss or accuracy measure, in some embodiments the loss function is modified to incorporate distribution effects. These may include cross-entropy (CE) loss, weighted CE, residual CE, inference distribution or a custom loss function.

Cross Entropy Loss is a commonly used loss function, which has a tendency to outperform simple mean-squared-of-difference between the ground truth and the predicted value. If the result of the network is passed through a Softmax layer, such as is the case here, then the distribution of the cross entropy results in better accuracy. This is because is naturally maximizes the likelihood of classifying the input data correctly, by not weighting distant outliers too heavily. For an input array, batch, representing a batch of images, and class representing viable or non-viable, the cross entropy loss is defined as:

$$\text{loss}(p,C) = \Sigma_{i=1}^{M} y_i \log(p_i) \quad (3)$$

where C is the number of classes. In the binary case this can be simplified to:

$$\text{loss}(p,C) = -(y \log(p)) + (1-y)\log(1-p) \quad (4)$$

An optimised version is:

$$\text{loss (batch, class)} = -\log\left(\frac{\exp(\text{batch [class]})}{\Sigma_j \exp(\text{batch } [j])}\right) \quad (5)$$

If the data contains a class bias, that is, more viable than non-viable examples (or vice-versa), the loss function should be weighted proportionally so that misclassifying an element of the less numerous class is penalized more heavily. This is achieved by pre-multiplying the right hand side of Eq. (2) with the factor:

$$\text{weight [class]} = \frac{N}{C * N[\text{class}]} \quad (6)$$

where N[class] is the total number of images for each class, N is the total number of samples in the dataset and C is the number of classes. It is also possible to manually bias the weight towards the viable embryos in order to reduce the number of false negatives compared to false positives, if necessary.

In some embodiments an Inference Distribution may be used. While it is important to seek a high level of accuracy in classifying embryos, it is also important to seek a high level of transferability in the model. That is, it is often beneficial to understand the distribution of the scores, and that while seeking a high accuracy is an important goal, the separate of the viable and non-viable embryos confidently with a margin of certainty is an indicator that the model will generalize well to a test set. Since the accuracy on the test set is often used to quote comparisons with important clinical benchmarks, such as the accuracy of the embryologist classification on the same embryo, ensuring generalizability should also be incorporated into the batch-by-batch assessment of the success of the model, each epoch.

In some embodiments a Custom Loss function is used. In one embodiment, we have customized how we define the loss function so that the optimization surface is changed to make global minima more obvious and so improve the robustness of the model. To achieve this, a new term is added to the loss function which maintains differentiability, called a residual term, which is defined in terms of the networks weights. It encodes the collective difference in the predicted value from the model and the target outcome for each image, and includes it as an additional contribution to the normal cross entropy loss function. The formula for the residual term is as follows, for N images:

$$\text{residual} = \frac{1}{\sqrt{\Sigma_{i=1}^{N}(\text{target}-\text{prediction})[i]*(\text{target}-\text{prediction})[i]}} \quad (7)$$

For this Custom Loss function, well-space clusters of viable and non-viable embryo scores are thus considered consistent with an improve loss rating. It is noted that this custom loss function is not specific to the embryo detection application, and could be used in other Deep Learning Models.

In some embodiments the models are combined to generate a more robust final AI model 100. That is deep learning and/or computer vision models are combined together to contribute to the overall prediction of the embryo viability.

In one embodiment an ensemble method is used. First, models that perform well are selected. Then, each model 'votes' on one of the images (using augmentations or otherwise), and the voting strategy that leads to the best result is selected. Example voting strategies include maximum-confidence, mean-value, majority-mean-value, median-value, mean-confidence, median-confidence, majority-mean-confidence, weighted average, majority-max-confidence, etc. Once the voting strategy has been selected, the evaluation method for the combination of augmentations must also be selected, which describes how each of the rotations should be treated by the ensemble, as before. In this embodiment the final AI model 100 can thus be defined as a collection of trained AI models, using deep learning and/or computer vision models, together with a mode, which encodes the voting strategy that defines how the individual AI model results will be combined, and an evaluation mode that defines how the augmentations (if present) will be combined.

Selection of the models was performed in such a way that their results contrast from one another, i.e. their results are independent as possible, and the scores are well distributed. This selection procedure is carried out by examining which images in the test set have been correctly identified for each model. If the sets of correctly identified images are very similar when comparing two models, or the scores provided by each model are similar to each other for a given image, then the models are not considered contrasting models. If, however, there is little overlap between the two sets of correctly identified images, or the scores provided for each image are markedly different from each other, then the models are considered contrasting. This procedure effectively assesses whether the distributions of the embryo scores on a test set for two different models are similar or not. The contrasting criterion drives model selection with diverse prediction outcome distributions, due to different input images or segmentation. This method ensured translatability by avoiding selection of models that performed well only on specific clinic datasets, thus preventing overfitting. Additionally model selection may also use a diversity criterion. The diversity criterion drives model selection to include different model's hyper-parameters and configurations. The reason is that, in practice, similar model settings result in similar prediction outcomes and hence may not be useful for the final ensemble model.

In one embodiment this can be implemented by using a counting approach and specifying a threshold similarity, such as 50%, 75% or 90% overlapping images in the two sets. In other embodiments, the scores in a set of images (e.g. the viable set) could be totalled and two sets (totals) compared, and ranked similar if the two totals are less than a threshold amount. Statistical based comparisons could also be used, for example taking into account the number of images in the set, or otherwise comparing the distribution of images in each of the sets.

In other embodiments a distillation method could be used to combine the individual AI models. In this approach the AI models are used as teacher models to train a student model. Selection of the individual AI models may be performed using diversity and contrasting criterion as discussed for ensemble methods. Further other methods for selecting the best model from a range of models or for combining outputs from multiple models into a single output maybe used.

An embodiment of an ensemble based embryo viability assessment model was generated and two validation (or bench marking) studies were performed in IVF clinics to assess the performance of the embryo viability assessment model described herein compared to working embryologists. For ease of reference this will be referred to as the ensemble model. These validation studies showed that the embryo viability assessment model showed a greater than 30% improvement in accuracy in identifying the viability of embryos when compared directly with world-leading embryologists. The studies thus validates the ability of embodiments of the ensemble model described herein to inform and support embryologists' selection decision, which is expected to contribute to improved IVF outcomes for couples.

The first study was a pilot study conducted with an Australian clinic (Monash IVF) and the second study was conducted across multiple clinics and geographical sites. The studies assessed the ability of an embodiment of an ensemble based embryo viability assessment model as described, to predict Day 5 embryo viability, as measured by clinical pregnancy.

For each clinical study, each patient in the IVF process may have multiple embryos to select from. An embodiment of an embryo viability assessment model as described herein was used to assess and score the viability of each of these embryos. However, only embryos that are implanted and which the pregnancy outcome is known (e.g. foetal heartbeat detected at the first ultrasound scan) can be used to validate the accuracy of the model. The total data set thus comprises images of embryos that have been implanted into the patient, with associated known outcomes, for which the accuracy (and thus the performance) of the model can be validated.

To provide further rigor with respect to the validation, some of the images used for validation comprise the embryologist's score as to the viability of the embryo. In some cases, an embryo that is scored as 'non-viable' may still be implanted if it nevertheless still the most favorable embryo choice, and/or upon the request of the patient. This data enables a direct comparison of how the ensemble model performs compared with the embryologist. Both the ensemble model and the embryologists' accuracies are measured as the percentage of the number of embryos that were scored as viable and had a successful pregnancy outcome (true positives), in addition to the number of embryos that were scored non-viable and had an unsuccessful pregnancy outcome (true negatives), divided by the total number of scored embryos. This approach is used to validate whether the ensemble model performs comparably or better when directly compared with leading embryologists. It is noted that not all images have corresponding embryologist scores in the dataset.

In order to make a direct comparison of the accuracy of a selection model with the current manual method employed by embryologists, the following interpretation of the embryologist scores for each clinic is used, for a degree of expansion that is at least a blastocyst ('BL' in Ovation Fertility notation, or 'XB' in Midwest Fertility Specialists notation). Embryos that are listed as the cellular stage (e.g. 10 cell), as compacting from the cellular stage to the morula, or as cavitating morula (where the blastocoel cavity is less than 50% of the total volume at Day 5 after IVF) are considered likely to be non-viable.

The letter grades that denote the quality of the IntraZonal Cavity (first letter) and trophectoderm (second letter) are arranged into bands of embryo quality, as discerned by the embryologist. A division is then made to denote whether an embryo was judged likely to be non-viable or viable, using Table 1 below. Bands 1 through 3 are considered likely to be viable, and bands 4 and greater are considered likely to be non-viable. In band 6, the embryo is considered likely to be non-viable if either letter score is worse than 'C'. In band 7, a score of '1XX' from Midwest Fertility Specialists indicates an early blastocyst with early (large) trophectoderm cells and without a discernible IntraZonal Cavity, and is considered likely to be non-viable.

TABLE 1

Ovation Fertility and Midwest Fertility Specialists embryologist score bands for likely viability.

| Banding | IntraZonal Cavity Quality | Trophectoderm Quality | Likely viability |
| --- | --- | --- | --- |
| band 1 | A | A | viable |
| band 2 | A | B | viable |
| band 2 | B | A | viable |
| band 3 | A | C | viable |
| band 3 | C | A | viable |
| band 3 | B | B | viable |
| band 4 | B | C | non-viable |
| band 4 | C | B | non-viable |
| band 5 | C | C | non-viable |
| band 6 | <C | any | non-viable |
| band 6 | any | <C | non-viable |
| band 7 | N/A | 1XX | non-viable |
| 10 cell/compacting/ cavitating morula | N/A | N/A | non-viable |

A set of approximately 20,000 embryo images taken at Day 5 after IVF was obtained along with related pregnancy and pre-implantation genetic screening (PGS) outcomes, and demographic information, including patient age and clinic geographical location. The clinics that contributed data to this study are: Repromed (Adelaide, SA, Australia) as part of Monash IVF Group (Melbourne, VIC, Australia), Ovation Fertility (Austin, Tex., USA), San Antonio IVF (San Antonio, Tex., USA), Midwest Fertility Specialists (Carmel, Ind., USA), Institute for Reproductive Health (Cincinnati, Ohio, USA), Fertility Associates (Auckland, Hamilton, Wellington, Christchurch and Dunedin, New Zealand), Oregon Reproductive Medicine (Portland, Oreg., USA) and Alpha Fertility Centre (Petaling Jaya, Selangor, Malaysia).

The generation of an AI model for use in the trial proceeded as follows. First a range of model architectures (or model types) are generated and each AI model is trained with various settings of model parameters and hyper-parameters, including input image resolution, choice of optimizer, learning rate value and scheduling, momentum value, dropout, and initialization of the weights (pre-training). Initial filtering is performed to select models which exhibit stability (accuracy stable over the training process), transferability (accuracy stable between training and validation sets) and predictions accuracy. Prediction accuracy examined which models provided the best validation accuracy, for both viable and non-viable embryos, the total combined accuracy, and the balanced accuracy, defined as the weighted average accuracy across both class types of embryos. In one embodiment, the use of ImageNet pretrained weights demonstrated improved performance of these quantities. Evaluation of loss functions indicated that weighted CE and residual CE loss functions generally outperformed other models.

Next models were then separated into two groups: first, those that included additional image segmentation (Zona or IZC identification), and second those that use the entire unsegmented image (i.e. full embryo models). Models that were trained on images that masked the IZC, exposing the zona region, were denoted as zona models. Models that were trained on images that masked the zona (denoted IZC models), and models that were trained on full-embryo images, were also considered in training. A group of models encompassing contrasting architectures and pre-processing methods was selected in order to provide diversity and maximize performance on the validation set.

The final ensemble based AI model was an ensemble of the highest performing individual models selected on the basis of diversity and contrasting results. Well-performing individual models that exhibited different methodologies, or extracted different biases from the features obtained through machine learning, were combined using a range of voting strategies based on the confidence of each model. Voting strategies evaluated included mean, median, max, majority mean voting, maximum-confidence, mean-value, majority-mean-value, median-value, mean-confidence, median-confidence, majority-mean-confidence, weighted average, majority-max-confidence, etc. In one embodiment the majority mean voting strategy is used as in testing it outperformed other voting strategies giving the most stable model across all datasets.

In this embodiment the final ensemble based AI model includes eight deep learning models of which four are Zona models and four are full-embryo models. The final model configuration used in this embodiment is as follows:

One full-embryo ResNet-152 model, trained using SGD with momentum=0.9, CE loss, learning rate 5.0e-5, step-wise scheduler halving the learning rate every 3 epochs, batch size of 32, input resolution of 224×224, and a dropout value of 0.1;

One zona model ResNet-152 model, trained using SGD with momentum=0.99, CE loss, learning rate 1.0e-5, step-wise scheduler dividing the learning rate by 10 every 3 epochs, batch size of 8, input resolution of 299×299, and a dropout value of 0.1;

Three zona ResNet-152 models, trained using SGD with momentum=0.99, CE loss, learning rate 1.0e-5, step-wise scheduler dividing the learning rate by 10 every 6 epochs, batch size of 8, input resolution of 299×299, and a dropout value of 0.1, one trained with random rotation of any angle;

One full-embryo DenseNet-161 model, trained using SGD with momentum=0.9, CE loss, learning rate 1.0e-4, step-wise scheduler halving the learning rate every 5 epochs, batch size of 32, input resolution of 224×224, a dropout value of 0, and trained with random rotation of any angle;

One full-embryo DenseNet-161 model, trained using SGD with momentum=0.9, CE loss, learning rate 1.0e-4, step-wise scheduler halving the learning rate every 5 epochs, batch size of 32, input resolution of 299×299, a dropout value of 0; and One full-embryo DenseNet-161 model, trained using SGD with momentum=0.9, Residual CE loss, learning rate 1.0e-4, step-wise scheduler halving the learning rate every 5 epochs, batch size of 32, input resolution of 299×299, a dropout value of 0, and trained with random rotation of any angle.

The architecture diagram corresponding to ResNet-152, which features heavily in the final model configuration, is shown in FIG. 8. The final ensemble model was subsequently validated and tested on blind test datasets as described in the results section.

Measures of accuracy used in the assessment of model behaviour on data included sensitivity, specificity, overall accuracy, distributions of predictions, and comparison to embryologists' scoring methods. For the AI model, an embryo viability score of 50% and above was considered viable, and below 50% non-viable. Accuracy in identification of viable embryos (sensitivity) was defined as the number of embryos that the AI model identified as viable divided by the total number of known viable embryos that resulted in a positive clinical pregnancy. Accuracy in identification of non-viable embryos (specificity) was defined as the number of embryos that the AI model identified as non-viable divided by the total number of known non-viable embryos that resulted in a negative clinical pregnancy outcome. Overall accuracy of the AI model was determined using a weighted average of sensitivity and specificity, and percentage improvement in accuracy of the AI model over the embryologist was defined as the difference in accuracy as a proportion of the original embryologist accuracy (i.e. AI_accuracy−embryologist_accuracy)/embryologist_accuracy).

Pilot Study

Monash IVF provided the ensemble model with approximately 10,000 embryo images and related pregnancy and live birth data for each image. Additional data provided included patient age, BMI, whether the embryo was implanted fresh or was frozen prior, and any fertility related medical conditions. Data for some of the images contained the embryologist's score for the viability of the embryo. Preliminary training, validation and analysis showed that the model's accuracy is significantly higher for day 5 embryos compared with day 4 embryos. Hence all day 4 embryos were removed, leaving approximately 5,000 images. The usable dataset for training and validation was 4650 images. This initial dataset was split into 3 separate datasets. A further 632 images were then provided which was used as a second Blind validation dataset. The final datasets for training and validation include:

Training dataset: 3892 images;

Validation dataset: 390 images, of which 70 (17.9%) had a successful pregnancy outcome and 149 images included an embryologist score on the viability of the embryo;

Blind validation dataset 1: 368 images of which 76 (20.7%) had a successful pregnancy outcome and 121 images included an embryologist score on the viability of the embryo; and Blind validation dataset 2: 632 images of which 194 (30.7%) had a successful pregnancy outcome and 477 images included an embryologist score on the viability of the embryo Not all images have corresponding embryologist scores in the dataset. The sizes of the datasets, as well as the subsets that include embryologist scores, are listed below.

The ensemble based AI model was applied to the three validation datasets. The overall accuracy results for the ensemble model in identifying viable embryos are shown in Table 2. The accuracy results for the two blind validation datasets are the key accuracy indicators, however, results for the validation dataset are shown for completeness. The accuracy for identifying viable embryos is calculated as a percentage of the number of viable embryos (i.e. images that had a successful pregnancy outcome) that the ensemble model could identify as viable (a viability score of 50% or greater by the model) divided by the total number of viable embryos in the dataset. Similarly, the accuracy for identifying non-viable embryos is calculated as a percentage of the number of non-viable embryos (i.e. images that had an unsuccessful pregnancy outcome) that the ensemble model could identify as non-viable (a viability score of under 50% by the model) divided by the total number of non-viable embryos in the dataset.

Figure 9:
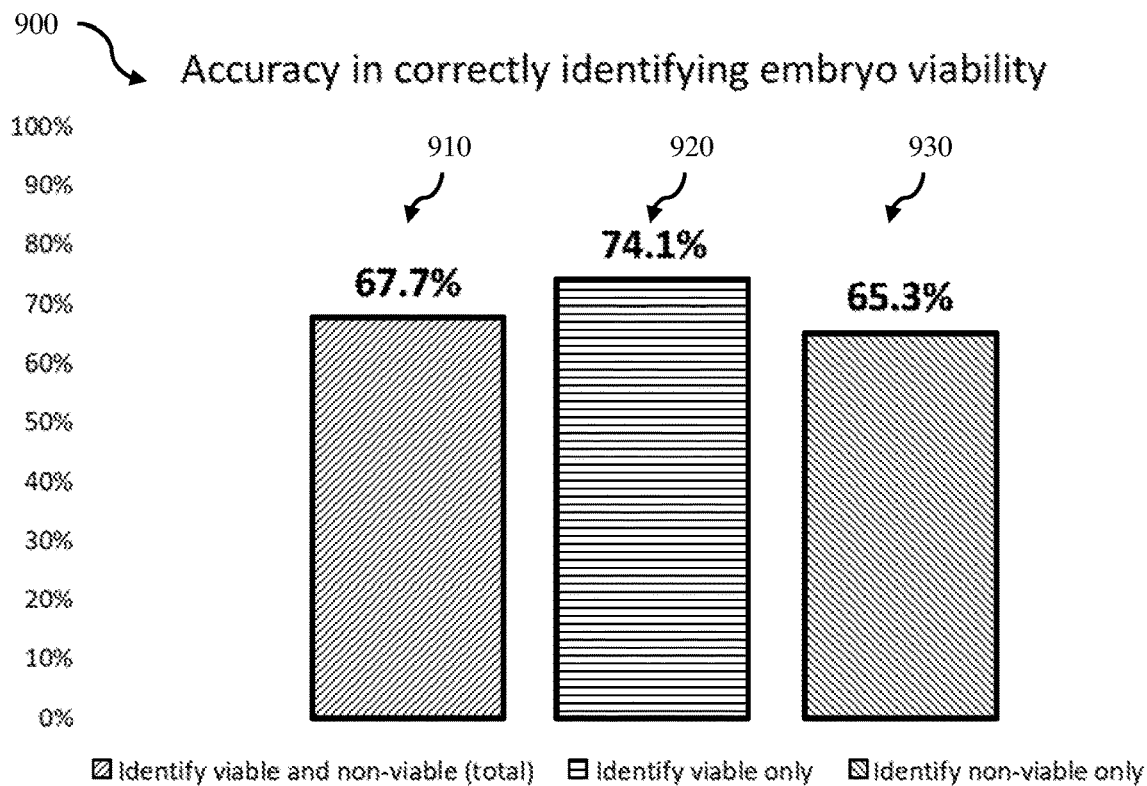
FIG. 9 is a plot of the accuracy of an embodiment of an ensemble model in identifying embryo viability according to an embodiment.

In the first stage of validation conducted with Monash IVF, the ensemble model's trained embryo viability assessment model was applied to two blind datasets of embryo images with known pregnancy outcomes, with a combined total of 1000 images (patients). FIG. 9 is a plot of the accuracy of an embodiment of an ensemble model in identifying embryo viability 900 according to an embodiment. The results showing that the ensemble model 910 had an overall accuracy of 67.7% in identifying embryo viability across the two blind validation datasets. Accuracy was calculated by summing the number of embryos that were identified as viable and led to a successful outcome, plus the number of embryos that were identified as non-viable and led to an unsuccessful outcome, divided by the total number of embryos. The ensemble model showed 74.1% accuracy in identifying viable embryos 920 and 65.3% accuracy in identifying non-viable embryos 930. This represents a significant accuracy improvement in this large dataset of embryos already pre-selected by embryologists and implanted into patients, where only 27% resulted in a successful pregnancy outcome.

To provide further rigor with respect to the validation, a subset of the images used for validation had an associated embryologist's score relating to the viability of the embryo (598 images). In some cases, an embryo that is scored as 'non-viable' by an embryologist may still be implanted if it is considered the most favorable embryo choice for that patient, and/or upon the request of the patient, despite a low likelihood of success. Embryo scores were used as a ground truth of the embryologists' assessment of viability and allow for a direct comparison of the ensemble model performance compared with leading embryologists.

The worst-case accuracy for the blind validation dataset 1 or 2 is 63.2% for identifying viable embryos in blind dataset 1, 57.5% for identifying non-viable embryos in blind dataset 2, and 63.9% total accuracy for blind dataset 2.

Table 3 shows the total mean accuracy across both blind datasets 1 and 2, which is 74.1% for identifying viable embryos, 65.3% for identifying non-viable embryos, and 67.7% total accuracy across both viable and non-viable embryos.

The accuracy values in both tables are high considering 27% of embryos result in a successful pregnancy outcome, and the ensemble model's difficult task of further classifying embryo images that have already been analyzed and selected as viable, or more favorable than other embryos in the same batch, by embryologists.

TABLE 3

Total mean accuracy of the embryo viability assessment model when applied to the blind validation datasets 1 and 2 only. Results show the accuracy in identifying viable embryos, non-viable embryos, and the total accuracy for both viable and non-viable embryos.

| Blind validation dataset 1 & 2 | Viable | Non-viable | Total |
|---|---|---|---|
| Total mean accuracy | 74.1% | 65.3% | 67.7% |

Table 4 shows the results comparing the model's accuracy with those of the embryologists. The accuracy values differ to those in the table above because not all embryos images in the datasets have embryo scores, and thus the results below are accuracy values on a subset of each dataset. The table shows that the model's accuracy in identifying viable embryos is higher than the embryologist. These results are illustrated in the bar chart 1000 in FIG. 10 with ensemble results 1010 on the left and embryologist results 1020 on the right.

TABLE 4

Comparison of the accuracy in identifying viable/non-viable embryos for the ensemble model versus world-leading embryologists.

| Dataset | Validation dataset | Blind validation dataset 1 | Blind validation dataset 2 | Total (Blind validation datasets 1 & 2 only) |
|---|---|---|---|---|
| Accuracy: the ensemble model | 74.5% | 71.9% | 65.4% | 66.7% |
| Accuracy: Embryologist | 39.6% | 47.1% | 52.0% | 51.0% |

Table 5 shows a comparison of the number of times that the model was able to correctly identify the viability of an embryo and the embryologist was not able to, and vice versa. The results show there were fewer occurrences where embryologists were correct and the model was incorrect compared with the cases where the model was correct and embryologists were incorrect. These results re illustrated in FIG. 11. This result further validates the high level of performance and accuracy of the ensemble model's embryo viability assessment model.

TABLE 2

Accuracy of the embryo viability assessment model when applied to the three types of validation datasets. Results show the accuracy in identifying viable embryos, non-viable embryos, and the total accuracy for both viable and non-viable embryos.

| Dataset | Validation dataset | | | Blind validation dataset 1 | | | Blind validation dataset 2 | | |
|---|---|---|---|---|---|---|---|---|---|
| Type | Viable | Non-viable | Total | Viable | Non-viable | Total | Viable | Non-viable | Total |
| Accuracy | 74.3% | 74.4% | 74.4% | 63.2% | 77.1% | 74.2% | 78.4% | 57.5% | 63.9% |

TABLE 5

Comparison of the accuracy in identifying viable/non-viable embryos for the ensemble model versus world-leading embryologists.

| Dataset | Validation dataset | Blind validation dataset 1 | Blind validation dataset 2 | Total (Blind validation datasets 1 & 2 only) |
|---|---|---|---|---|
| Ensemble model correct and embryologist incorrect | 62 out of 149 | 42 out of 121 | 106 out of 477 | 148 out of 598 |
| Embryologist correct and the ensemble model incorrect | 10 out of 149 | 12 out of 121 | 42 out of 477 | 54 out of 598 |

Figure 10:
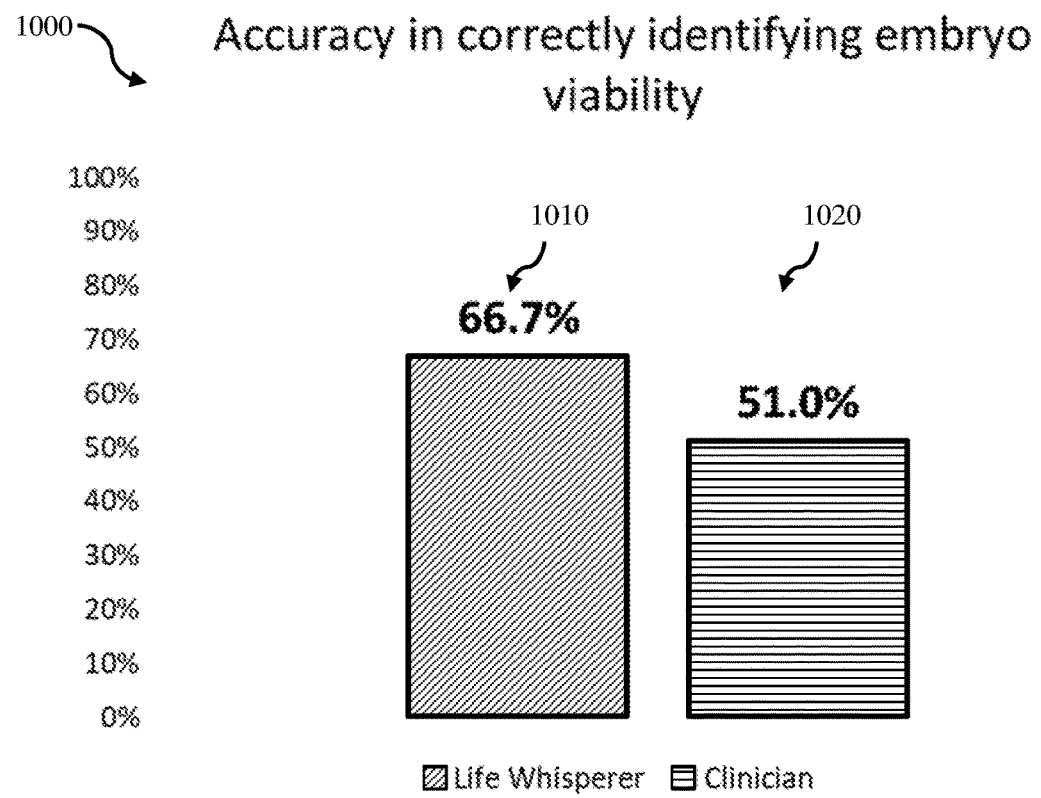
FIG. 10 is a bar chart showing the accuracy of an embodiment of the ensemble model compared to world-leading embryologists (clinicians) in accurately identifying embryo viability.
Figure 11:
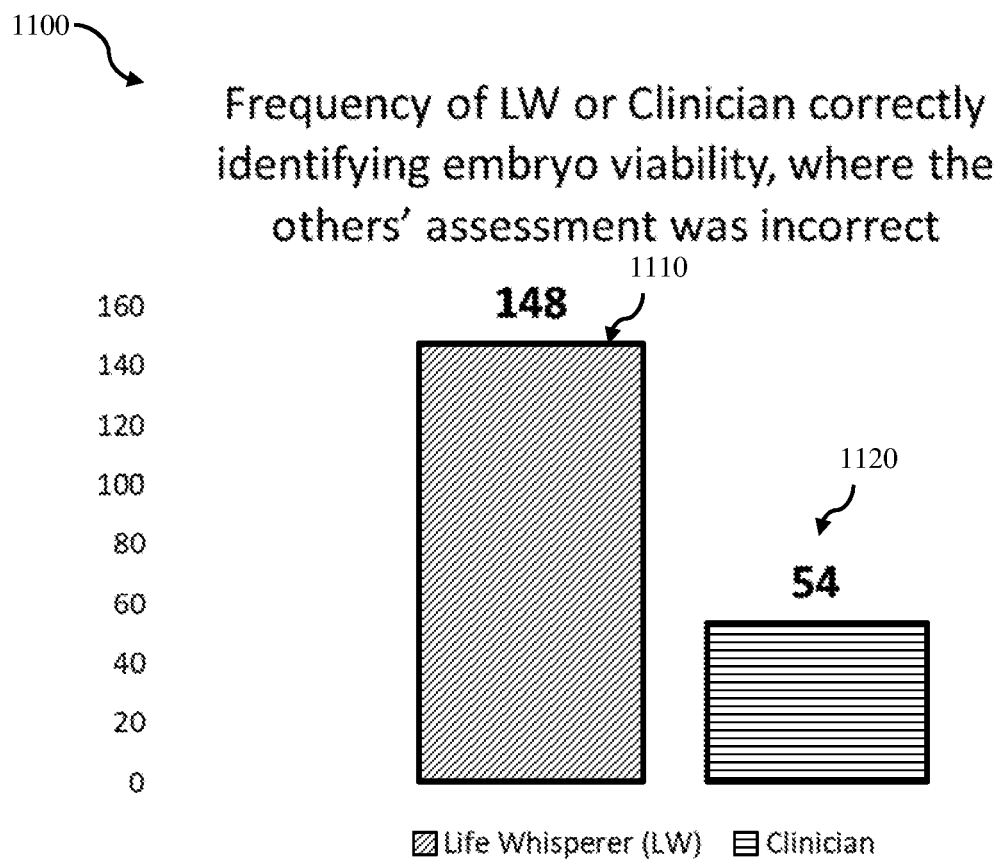
FIG. 11 is a bar chart showing the accuracy of an embodiment of the ensemble model compared to world-leading embryologists (clinicians) in correctly identifying embryo viability where the embryologists' assessment was incorrect, compared with embryologists correctly identifying embryo viability where the ensemble model assessment was incorrect.

Overall, the ensemble model achieved a total of 66.7% accuracy in identifying the viability of embryos, whereas embryologists' achieved 51% accuracy based on their scoring method (FIG. 10). The additional 15.7% accuracy represents a significant 30.8% performance (accuracy) improvement for the ensemble model compared with embryologists (p=0.021, n=2, Student's t test). Specifically, results show that the ensemble model was able to correctly classify embryo viability 148 times when embryologists were incorrect, and conversely embryologists' correctly classified embryo viability only 54 times where the ensemble model was incorrect. FIG. 11 is a bar plot showing the accuracy of an embodiment of the ensemble model (bar 1110) compared to world-leading embryologists (clinicians) (bar 1120) in correctly identifying embryo viability where the embryologists' assessment was incorrect, compared with embryologists correctly identifying embryo viability where the ensemble model assessment was incorrect. These results show a clear advantage of the ensemble model in identifying viable and non-viable embryos when compared with world-leading embryologists. A further validation study was performed for embryo images from Ovation Fertility with similar results.

The successful validations demonstrate that the ensemble model's approach and technology can be applied to embryos images to create a model that can accurately identify viable embryos and ultimately lead to improved IVF outcomes for couples. The model was then further tested in a larger cross clinic study Cross Clinic Study In a more general cross-clinic study following the Australian pilot study, over 10,000 embryo images were sourced from multiple demographics. Of these images, over 8,000 can be related to the embryologist's score for the viability of the embryo. For training, each image needs to be labeled as viable or non-viable to allow the deep learning and computer vision algorithms to identify patterns and features relating to the viability of the embryos.

In the first cross-clinic study, the usable dataset of 2217 images (and linked outcomes) for developing the ensemble model is split into three subsets in the same manner as the pilot study: the training dataset, validation dataset and blind validation dataset. These studies include data sourced from the clinics: Ovation Fertility Austin, San Antonio IVF, Midwest Fertility Specialists, and Institute for Reproductive Health and Fertility Associates NZ. This comprised:

Training dataset: 1744 images—886 non-viable, 858 viable;
Validation dataset: 193 images—96 non-viable, 97 viable; and
Blind validation dataset 1: 280 images—139 non-viable, 141 viable;

After completion of the training, validation and blind validation phases, a second study is conducted on a completed separate demographic, sourced from the clinic: Oregon Reproductive Medicine. This dataset comprised Blind validation dataset 2: 286 images—106 non-viable, 180 viable.

A third study utilizes the EmbryoScope images sourced from the clinic: Alpha Fertility Centre:

EmbryoScope validation dataset: 62 images—32 non-viable, 30 viable.

In producing the trained ensemble based AI model, the same training dataset is used for each model that is trained, so that they can be compared in a consistent manner.

The final results for the ensemble based AI model, as applied to the mixed demographic blind validation dataset, are as follows. A summary of the total accuracy can be found in Table 6.

TABLE 6

Accuracy of the ensemble based AI model, when applied to the blind validation dataset of Study 1 of the cross clinic study. Results show the accuracy in identifying viable embryos, non-viable embryos, and the total accuracy for both viable and non-viable embryos combined.

| Blind validation dataset | Viable | Non-viable | Total |
|---|---|---|---|
| Model accuracy | 99/141 = 70.21% | 87/139 = 62.59% | 181/280 = 66.43% |

Figure 12:
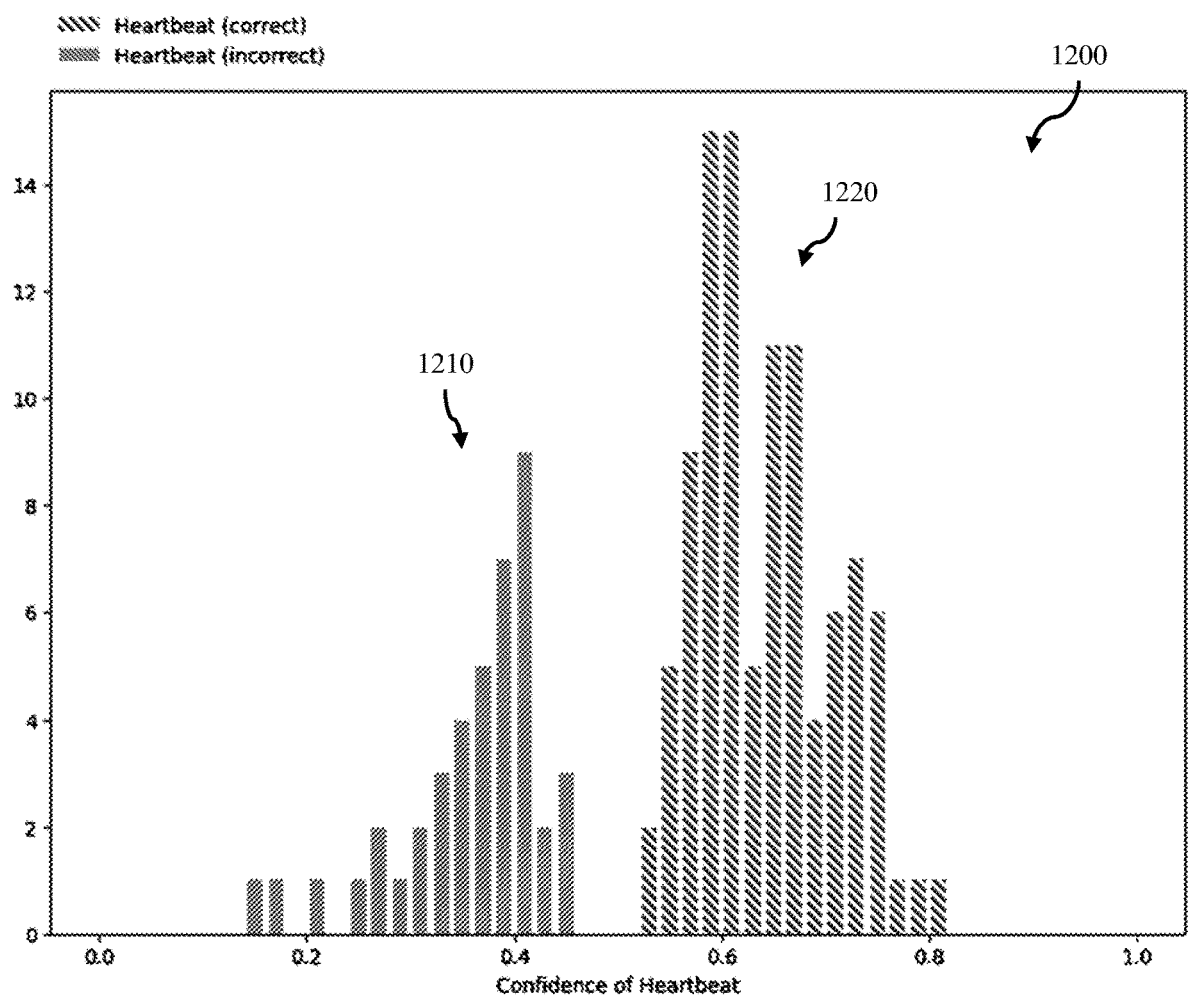
FIG. 12 is a plot of the distribution of inference scores for viable embryos (successful clinical pregnancy) using the embodiment of the ensemble model, when applied to the blind validation dataset of Study 1.
Figure 13:
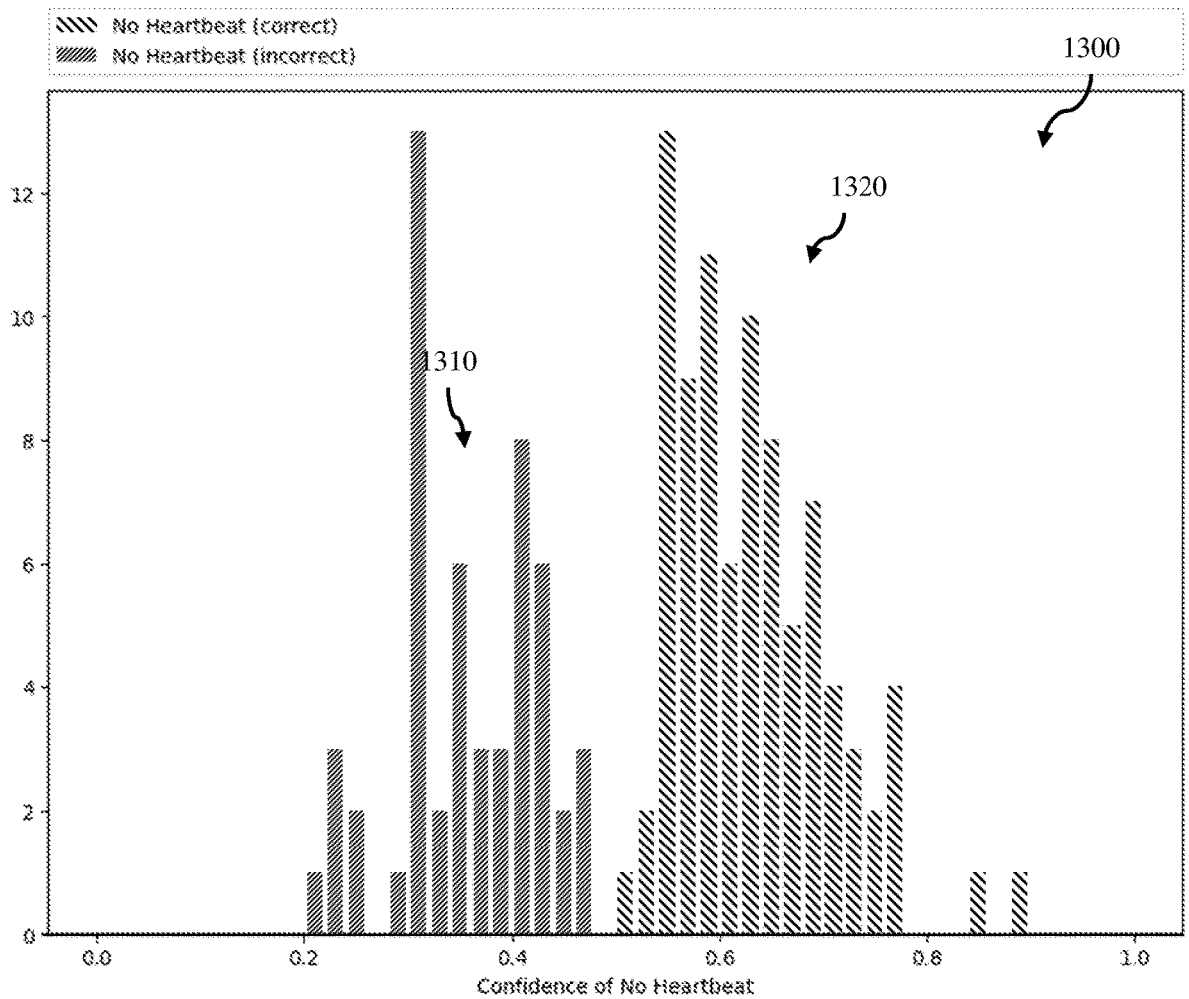
FIG. 13 is a plot of the distribution of inference scores for non-viable embryos (unsuccessful clinical pregnancy) using the embodiment of the ensemble model, when applied to the blind validation dataset of Study 1.

The distribution of the inferences, displayed as histograms, is shown in FIGS. 12 and 13. FIG. 12 is a plot of the distribution of inference scores 1200 for viable embryos (successful clinical pregnancy) using the embodiment of the ensemble based AI model, when applied to the blind validation dataset of Study 1. The inferences are normalized between 0 and 1, and can be interpreted as confidence scores. Instances where the model is correct are marked in boxes filled with thick downward diagonal lines (True Positives 1220); whereas instances where the model is incorrect are marked in in boxes filled with thin upward diagonal lines (False Negatives 1210). FIG. 13 is a plot of the distribution of inference scores for non-viable embryos (unsuccessful clinical pregnancy) 1300 using the embodiment of the ensemble based AI model, when applied to the blind validation dataset of Study 1. The inferences are normalized between 0 and 1, and can be interpreted as confidences scores Instances where the model is correct are marked in boxes filled with thick downward diagonal lines (True Negatives 1320), whereas instances where the model is incorrect are marked in boxes filled with thin upward diagonal lines (False Positives 1310). There is clear separation between the two groups. These histograms show good separation between the correctly and incorrectly identified embryo images, which provides evidence that the model will translate well to a blind validation set.

FIG. 13 contains a tall peak in the False Positives 1310 (boxes filled with thin upward diagonal lines), which is not as prominent in the equivalent histogram for the False Negatives in FIG. 12. The reason for this effect could be due to the presence of patient health factors, such as uterine scarring, that cannot be identified through the embryo image itself. The presence of these factors means that even an ideal embryo may not lead to a successful implantation. This also limits the upper value of the accuracy in predicting successful clinical pregnancy using embryo imagine analysis alone.

In the selection of an embryo, it is widely considered preferential to allow a non-viable embryo to be implanted (False Positive) than to jeopardize a potentially healthy embryo (False Negative). Therefore, in obtaining the final ensemble based AI model that forms the ensemble based AI model, effort has been made, where possible, to bias residual inaccuracies to minimize the False Negatives preferentially. Therefore, the final model will have a higher sensitivity than specificity, i.e. a higher accuracy at selecting viable embryos than non-viable embryos. To bias the model to prioritize minimizing the False Negatives, models are selected for inclusion in the final ensemble based AI model such that the ensemble based AI model accuracy on the set of viable embryo images is higher than the accuracy on the set of non-viable embryo images, if possible. If models cannot be found such that they combine together to provide a bias to the viability accuracy, then an additional parameter is sometimes supplied during training, which increases the penalty for misclassifying a viable embryo.

While the total accuracy is useful for roughly assessing the overall efficacy of the model, complexities regarding different demographics have necessarily been averaged. Therefore, it is instructive to consider a breakdown of the results into various key groups, described below.

Study 1: Demographic Cross-Sections

To explore the behavior of the ensemble based AI model, the following demographic groups are considered. First, the accuracy on the dataset provided by Fertility Associates NZ is lower than those of the US-based clinics. This is likely due to the diversity inherent in the data from this clinic, which encompasses a number of different cities, camera filters and brightness levels, over which the ensemble based AI model must take an average. It is anticipated that further training of the AI on much larger datasets will be able to account for the camera diversity by incorporating it into a fine-tuning training dataset. The accuracies including and excluding the NZ data are shown in Tables 7 and 8.

Because of the smaller number of images from the clinics Midwest Fertility Associates and San Antonio IVF, the sample sizes are too small individually to provide a reliable accuracy measure. Therefore, their outcomes have been combined together with the results from Ovation Fertility Austin in Table 7.

TABLE 7

Accuracy of the ensemble based AI model, when applied to the blind validation dataset of Study 1, as broken down by clinic.

| Blind validation clinic | Viable | Non-viable | Total |
| --- | --- | --- | --- |
| Total including NZ | 99/141 = 70.21% | 87/139 = 62.59% | 181/280 = 66.43% |
| Total excluding NZ | 62/79 = 78.48% | 47/77 = 61.04% | 109/156 = 69.87% |
| Fertility Associates NZ | 37/62 = 59.68% | 40/62 = 64.52% | 77/124 = 62.10% |
| Ovation Austin + Midwest Fertility | 26/30 = 86.67% | 19/31 = 61.29% | 45/61 = 73.77% |
| Ovation Austin + Midwest Fertility + San Antonio IVF | 33/39 = 84.62% | 20/35 = 57.14% | 53/74 = 71.62% |
| Institute for Reproductive Health | 29/40 = 72.50% | 27/42 = 64.29% | 56/82 = 68.29% |

A study of the effect of patient age on the accuracy of the ensemble based AI model was also conducted, shown in Table 7. It was found that embryo images corresponding to patients equal to or over 35 years were classified more accurately. If the age cutoff is lifted to 38 years, the accuracy improved again, indicating that the ensemble based AI model is more sensitive to morphological characteristics that become more prominent with age.

TABLE 8

Accuracy of the ensemble based AI model, when applied to the blind validation dataset of Study 1, as broken down into age, or hatched/non-hatched bandings.

| Blind validation demographic | Viable | Non-viable | Total |
| --- | --- | --- | --- |
| Patient age under 35 | 52/76 = 68.42% | 47/77 = 61.04% | 99/153 = 64.71% |
| Patient age over/ equal to 35 | 47/65 = 72.31% | 40/62 = 64.52% | 87/127 = 68.50% |
| Patient age under 38 | 78/111 = 70.27% | 65/107 = 60.75% | 143/218 = 65.60% |
| Patient age over/ equal to 38 | 21/30 = 70.00% | 22/32 = 68.75% | 43/62 = 69.35% |
| Non-hatched embryos | 70/107 = 65.42% | 69/108 = 63.89% | 139/215 = 64.65% |
| Hatched embryos | 28/31 = 90.32% | 11/23 = 47.83% | 39/54 = 72.22% |

Whether the embryo has been treated with a hatched or non-hatched protocol prior to transfer was also considered. It was found that while hatched embryos which exhibit more gross morphological features were more easily identified by the AI than non-hatched embryos, the specificity was reduced in the former case. This is likely a result of the fact that an ensemble based AI model trained on a mixed dataset of hatched and non-hatched embryos will have a tendency to associate successfully hatched embryos with viability.

Study 1: Embryologist Ranking Comparison

A summary of the accuracies of the ensemble based AI model and the embryologist can be found in Tables 9 and 10 for the same demographic breakdown considered in Section 5A. Only embryo images that have a corresponding embryologist score are considered in this Study.

The percentage improvement of the ensemble based AI model over the embryologist in accuracy is quoted, as defined by the difference in accuracy as a proportion of the original embryologist accuracy (AI_accuracy−embryologist_accuracy)/embryologist_accuracy. It is found that while the improvement across the total number of images was 31.85%, the improvement is highly variable across specific demographics, as the improvement factor is highly sensitive to the performance of the embryologist on each given dataset.

In the case of Fertility Associates NZ, the embryologists performed significantly better than other demographics, leading to an improvement of only 12.37% using the ensemble based AI model. In cases where the ensemble based AI model performed very well, such as Ovation Fertility Austin, the improvement was as high as 77.71%. A comparison of the performance of the ensemble based AI model compared to the embryologist is also reflected in the total number of images correctly assessed where its comparator incorrectly assessed the same image, as seen in the last two columns of both Tables 9 and 10.

TABLE 9

Embryologist comparison for images that have embryologist scores, as broken down by clinic.

| Blind validation demographic | Model accuracy | Embryologist accuracy | Percentage improvement | Model correct, embryologist incorrect (# images) | Model incorrect, embryologist correct (# images) |
|---|---|---|---|---|---|
| Total including NZ | 174/262 = 66.41% | 132/262 = 50.38% | 31.85% | 83 | 41 |
| Total excluding NZ | 105/148 = 69.59% | 69/148 = 46.62% | 49.87% | 53 | 19 |
| Fertility Associates NZ | 71/114 = 62.28% | 63/114 = 55.26% | 12.37% | 30 | 22 |
| Ovation Austin + Midwest Fertility | 39/53 = 73.58% | 22/53 = 41.51% | 77.71% | 22 | 5 |
| Ovation Austin + Midwest Fertility + San Antonio IVF | 47/66 = 71.21% | 29/66 = 43.94% | 63.00% | 27 | 9 |
| Institute for Reproductive Health | 56/82 = 68.29% | 40/82 = 48.78% | 40.00% | 26 | 10 |

If the embryologist score contains a numeral, or terminology representing a ranking of the embryos in terms of their advancement or arrestment (number of cells, compacting, morula, cavitation, early blastocyst, full blastocyst or hatched blastocyst), an alternative study comparing the efficacy of the ensemble based AI model and the embryologists assessment can be conducted. A comparison of the ranking of the embryos can be made by equating the embryologist assessment with a numerical score from 1 to 5, while dividing the AI inferences into 5 equal bands (from the minimum inference to the maximum inference), labeled 1 to 5. With both the ensemble based AI model and the embryologist scores expressed as an integer from 1 to 5, a comparison of ranking accuracy is made as follows.

If a given embryo image is given the same rank by the ensemble based AI model and the embryologist, this is noted as a concordance. If, however, the ensemble based AI model provides a higher rank than the embryologist and the ground-truth outcome was recorded as viable, or the ensemble based AI model provides a lower rank than the embryologist and the ground-truth outcome was recorded as non-viable, then this outcome is noted as model correct. Similarly, if the ensemble based AI model provides a lower rank than the embryologist and the ground-truth outcome was recorded as viable, or the ensemble based AI model provides a higher rank and the outcomes was recorded as non-viable, this outcome is noted as model incorrect. A summary of the proportions of images assessed as concordant, model correct or model incorrect can be found in Tables 11 and 12 for the same demographic breakdown considered above. The ensemble based AI model is considered to have performed well on a dataset if the model correct proportion is high, and the concordance and model incorrect proportions are low.

TABLE 10

Embryologist comparison for images that have embryologist scores, as broken down by clinic.

| Blind validation demographic | Model accuracy | Embryologist accuracy | Percentage improvement | Model correct, embryologist incorrect (# images) | Model incorrect, embryologist correct (# images) |
|---|---|---|---|---|---|
| Patient age under 35 | 95/146 = 65.07% | 74/146 = 50.68% | 27.66% | 45 | 24 |
| Patient age over/equal to 35 | 79/116 = 68.10% | 58/116 = 50.00% | 37.00% | 38 | 17 |
| Patient age under 38 | 134/204 = 65.67% | 103/204 = 50.49% | 29.92% | 64 | 33 |
| Patient age over/equal to 38 | 40/58 = 68.97% | 29/58 = 50.00% | 38.71% | 19 | 8 |
| Non-hatched embryos | 132/203 = 65.02% | 106/203 = 52.21% | 23.81% | 59 | 33 |
| Hatched embryos | 36/51 = 70.59% | 23/51 = 45.10% | 60.14% | 20 | 7 |

TABLE 11

Embryologist ranking study, where the proportions of rank concordance, model correct or model incorrect are expressed as percentages of the total images in each clinic.

| Blind validation demographic | Ranking: model correct | Ranking: model incorrect | Ranking: concordance |
|---|---|---|---|
| Total including NZ | 105/262 = 40.08% | 66/262 = 25.19% | 91/262 = 34.73% |

TABLE 11-continued

Embryologist ranking study, where the proportions of rank concordance, model correct or model incorrect are expressed as percentages of the total images in each clinic.

| Blind validation demographic | Ranking: model correct | Ranking: model incorrect | Ranking: concordance |
|---|---|---|---|
| Total excluding NZ | 65/148 = 43.92% | 31/148 = 20.95% | 52/148 = 35.14% |
| Fertility Associates NZ | 40/114 = 35.09% | 35/114 = 30.70% | 39/114 = 34.21% |
| Ovation Austin + Midwest Fertility | 31/53 = 58.49% | 15/53 = 28.30% | 7/53 = 13.21% |
| Ovation Austin + Midwest Fertility + San Antonio IVF | 39/66 = 59.09% | 19/66 = 28.79% | 8/66 = 12.12% |
| Institute for Reproductive Health | 26/82 = 31.71% | 12/82 = 14.63% | 44/82 = 53.66% |

TABLE 12

Embryologist ranking study, where the proportions of rank concordance, model correct or model incorrect are expressed as percentages of the total images in each demographic.

| Blind validation demographic | Ranking: model correct | Ranking: model incorrect | Ranking: concordance |
|---|---|---|---|
| Patient age under 35 | 52/146 = 35.62% | 40/146 = 27.40% | 54/146 = 36.99% |
| Patient age over/equal to 35 | 53/116 = 45.69% | 26/116 = 22.41% | 37/116 = 31.90% |
| Patient age under 38 | 75/204 = 36.76% | 57/204 = 27.94% | 72/204 = 35.29% |
| Patient age over/equal to 38 | 30/58 = 51.72% | 9/58 = 15.52% | 19/58 = 32.76% |
| Non-hatched embryos | 71/203 = 34.98% | 49/203 = 24.14% | 83/203 = 40.89% |
| Hatched embryos | 30/51 = 58.82% | 14/51 = 27.45% | 7/51 = 13.73% |

Figure 14:
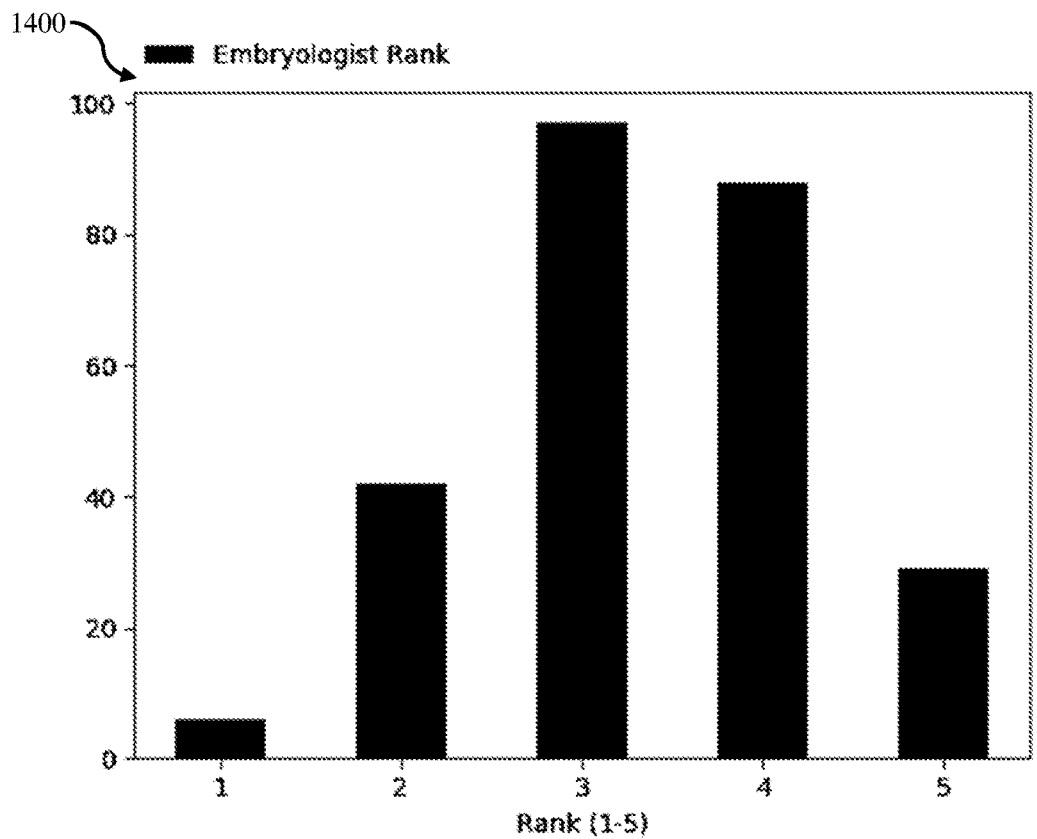
FIG. 14 is a histogram of the rank obtained from the embryologist scores across the total blind dataset.
Figure 15:
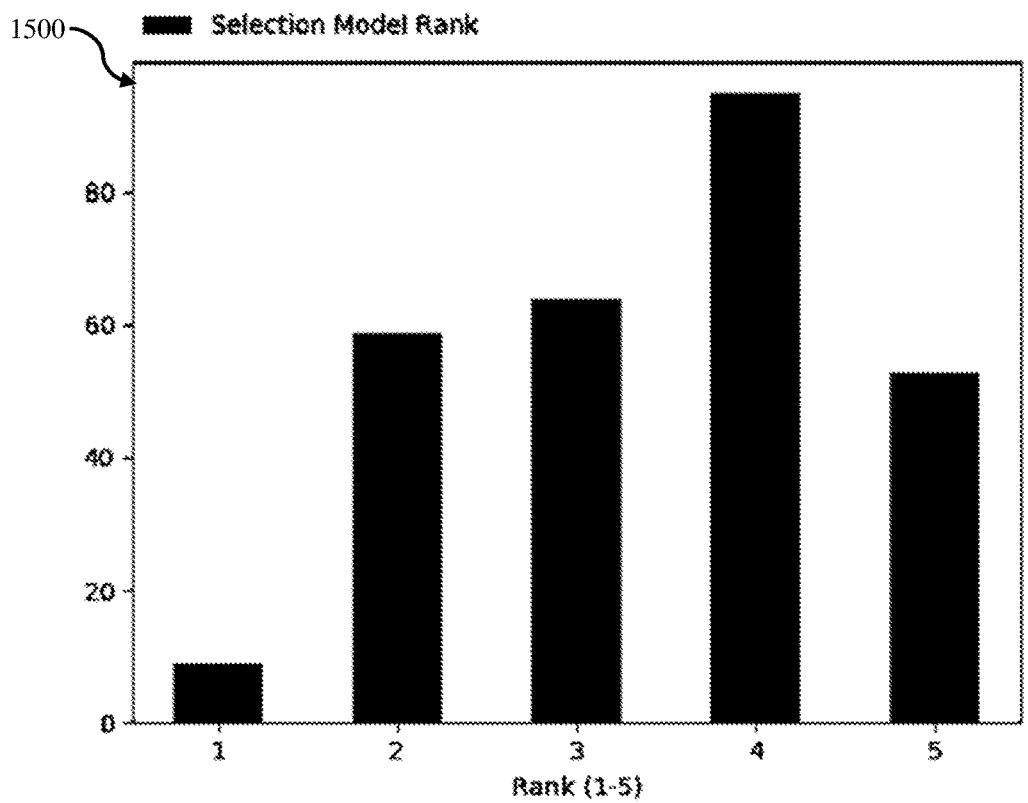
FIG. 15 is a histogram of the rank obtained from the embodiment of the ensemble model inferences across the total blind dataset.

A visual representation of the distribution of the rankings from the embryologist and the ensemble based AI model across the total blind dataset of Study 1 can be seen in the histograms in FIGS. 14 and 15, respectively. FIG. 14 is a histogram of the rank obtained from the embryologist scores across the total blind dataset 1400 and FIG. 15 is a histogram of the rank obtained from the embodiment of the ensemble based AI model inferences across the total blind dataset 1500.

Figure 16:
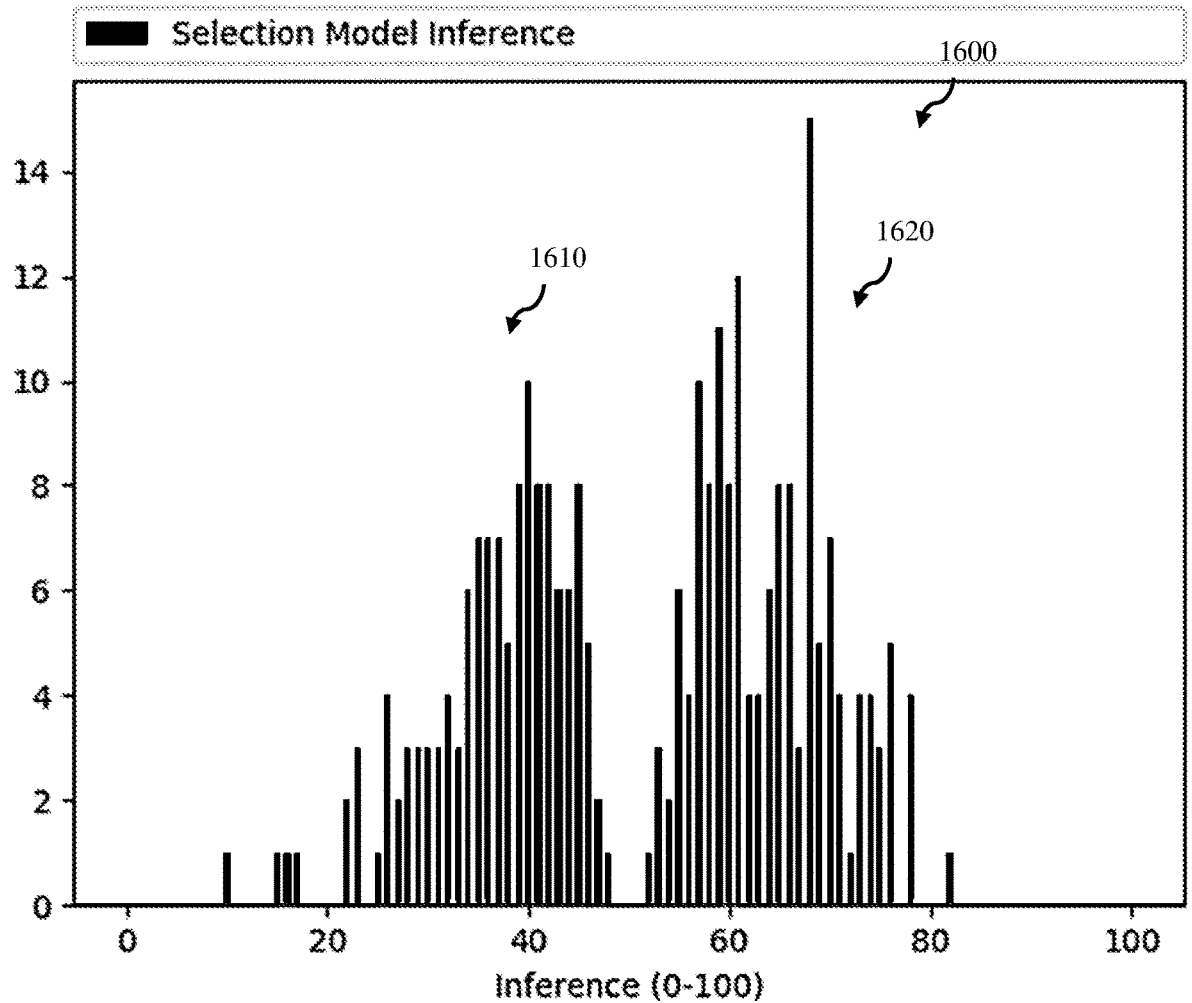
FIG. 16 is a histogram of the ensemble model inferences, prior to being placed into rank bandings from 1 to 5.

FIGS. 14 and 15 differ from each other in the shape of the distribution. While there is dominance in the embryologist scores around a rank value of 3, dropping off steeply for lower scores of 1 and 2, the ensemble based AI model has a more even distribution of scores around a value of 2 and 3, with a rank of 4 being the dominant score. FIG. 16 has been extracted directly from the inference scores obtained from the ensemble based AI model, which are shown as a histogram in FIG. 13 for comparison. The ranks in FIG. 12 are a coarser version of the scores in FIG. 13. The finer distribution in FIG. 16 shows that there is a clear separation between the scores below 50% (predicted non-viable) 1610 and those above (predicted viable) 1620. This suggests the ensemble based AI model provides greater granularity around embryo ranking than the standard scoring method, enabling a more definitive selection to be achieved.

Study 2—Secondary Blind Validation

In Study 2, embryo images were sourced from a separate clinic, Oregon Reproductive Medicine, to be used as a secondary blind validation. The total number of images with linked clinical pregnancy outcomes was 286, similar in size to the blind validation dataset in Study 1. The final results for the ensemble based AI model, as applied to the mixed demographic blind validation set can be found in Table 13. In this blind validation, there is a drop in accuracy of only (66.43%−62.64%=3.49%) compared to Study 1, which indicates that the model is translating across to the secondary blind set. However, the drop in accuracy is not uniform over the non-viable and viable embryos. The specificity is reduced, while the sensitivity remains stable. In this trial 183 low quality images sourced from an old (>1-years) Pixelink® camera were removed (failing quality criteria) before the commencement of the study to prevent them influencing the ensemble based AI model from correctly predict embryo viability.

TABLE 13

Accuracy of the ensemble based AI model, when applied to the blind validation dataset of Study 2 from Oregon Reproductive Medicine. Results show the accuracy in identifying viable embryos, non-viable embryos, and the total accuracy for both viable and non-viable embryos combined.

| Blind validation dataset 2 | Viable | Non-viable | Total |
|---|---|---|---|
| Accuracy on clinical pregnancy | 128/180 = 71.11% | 52/106 = 49.06% | 181/286 = 62.94% |

To explore this point further, a separate study was conducted in which embryo images were successively distorted, by introducing uneven cropping, scaling (blurring) or the addition of compression noise (such as jpeg artefacts). In each case it was found that the confidence in the ensemble based AI model prediction reduces as the artefacts are increased. Furthermore, it was found that there is a tendency for the ensemble based AI model to assign a non-viable prediction to a distorted image. This makes sense from the point of view of the ensemble based AI model, which cannot distinguish between an image of a damaged embryo, or a damaged image of a normal embryo. In both cases, a distortion is identified by the ensemble based AI model, and the likelihood of assigning the image a non-viable prediction increases.

As a confirmation of this analysis, the ensemble based AI model was applied to only the 183 Pixelink camera images removed from the main high quality image set from Oregon Reproductive Medicine, and the results are shown in Table 14.

TABLE 14

Accuracy of the ensemble based AI model, when applied to the low quality Pixelink images of Study 2 from Oregon Reproductive Medicine. Results show the accuracy in identifying viable embryos, non-viable embryos, and the total accuracy for both viable and non-viable embryos combined.

| Pixelink images only | Viable | Non-viable | Total |
|---|---|---|---|
| Accuracy on clinical pregnancy | 15/116 = 12.93% | 64/67 = 95.52% | 79/183 = 43.17% |

Figure 17:
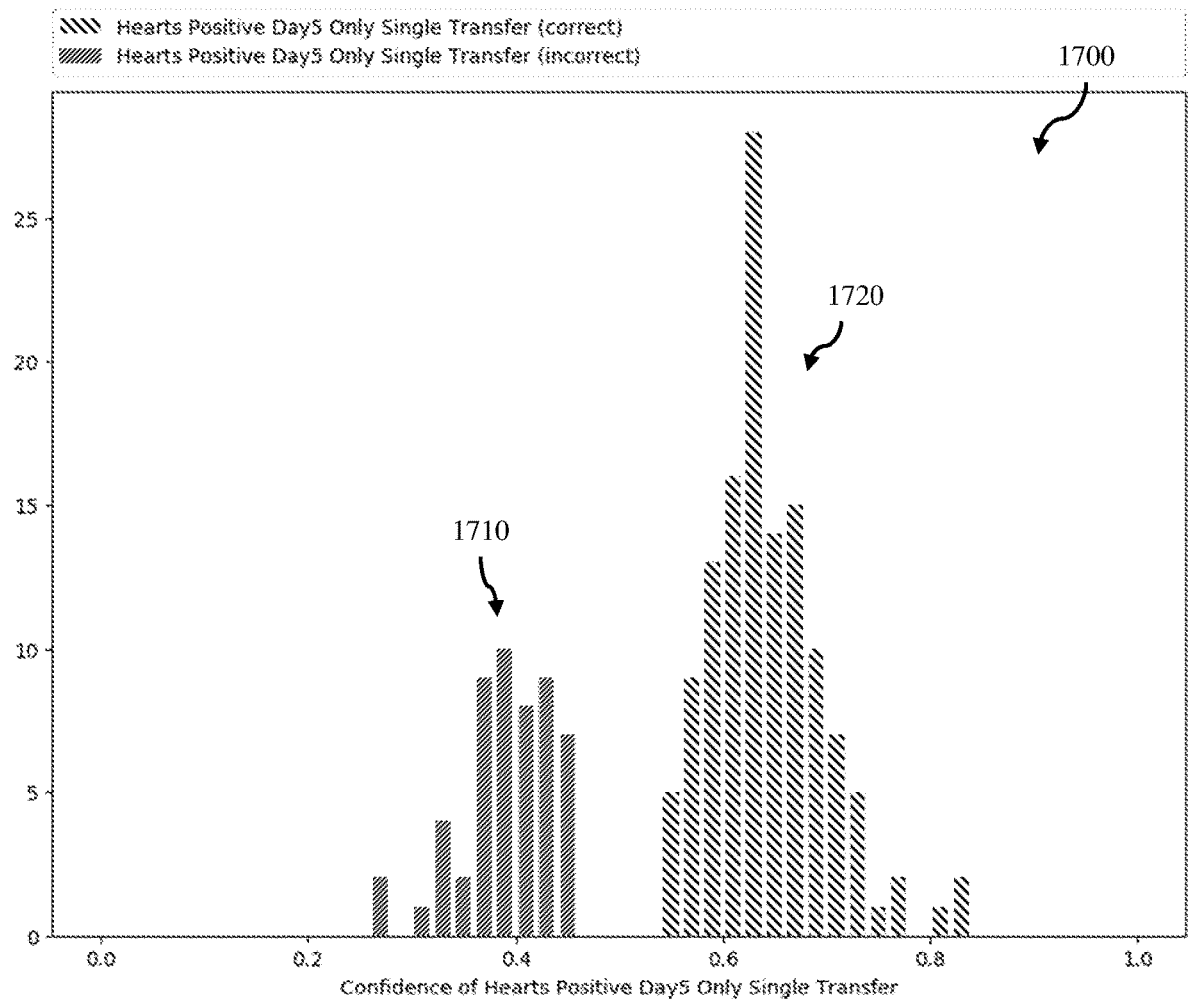
FIG. 17 is a plot of the distribution of inference scores for viable embryos (successful clinical pregnancy) using the ensemble model, when applied to the blind validation dataset of Study 2.
Figure 18:
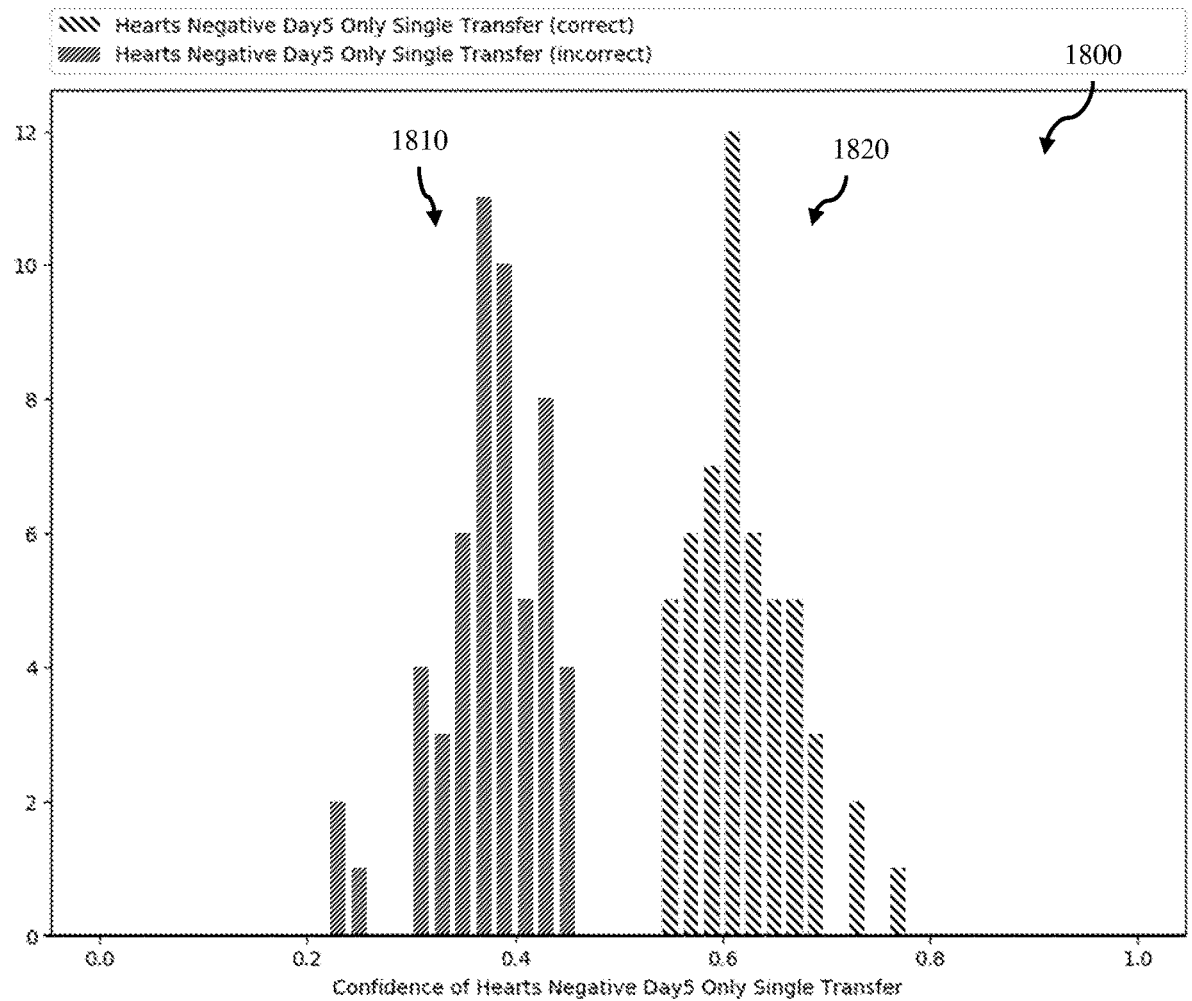
FIG. 18 is a plot of the distribution of inference scores for non-viable embryos (unsuccessful clinical pregnancy) using the ensemble model, when applied to the blind validation dataset of Study 2.

It is clear from Table 14 that in the case of distorted images and poor quality image (ie failing a quality assessment), not only will the ensemble based AI model performance drop, but a larger proportion of the images will be assigned a non-viable prediction. Further analysis of the ensemble based AI model behaviour on alternative camera setups, and a method for handling such artefacts to improve the result, is discussed in below. The distribution of the inferences, displayed as histograms 1700 and 1800, are shown in FIGS. 17 and 18. Just as in Study 1, FIGS. 17 and 18 both show a clear separation between the correct (1720; 1820; boxes filled with thick downward diagonal lines) and incorrect predictions (1710; 1810; boxes filled with thin upward diagonal lines) for both the viable and non-viable embryos. The shapes of the distributions between FIGS. 17 and 18 are also similar to each other, although there is a higher rate of False Positives than is the case for the False Negatives.

Study 3—EmbryoScope Validation

In Study 3, the potential performance of the ensemble based AI model on a dataset sourced from a completely different camera setup is explored. A limited number of EmbryoScope images were obtained from Alpha Fertility Centre, with the intention of testing the ensemble based AI model, which has been trained on phase contrast microscope images predominantly. The EmbryoScope images have a clear bright ring around the embryo coming from the incubator's lamp, and a dark region outside this ring, which is not present in a typical phase contrast microscope image from Study 1. Application of the model on the EmbryoScope images without any additional treatment results in an uneven prediction, where a high proportion of the images are predicted to be non-viable, leading to a high rate of False Negatives, and a low sensitivity, as shown in Table 15. However, using computer vision imaging techniques, a coarse, first-pass application to bring the image closer to its expected form results in a significant rebalancing of the inferences, and an increase in accuracy.

TABLE 15

Accuracy of the ensemble based AI model, when applied to the blind validation dataset of Study 3 from Alpha Fertility Centre. Results show the accuracy in identifying viable embryos, non-viable embryos, and the total accuracy for both viable and non-viable embryos.

| Pixelink images only | Viable | Non-viable | Total |
| --- | --- | --- | --- |
| Accuracy before image treatment | 8/30 = 26.67% | 27/32 = 84.38% | 35/62 = 56.45% |
| Accuracy after image treatment | 17/62 = 56.67% | 23/62 = 71.88% | 40/62 = 64.52% |

While this dataset is small, it nevertheless provides evidence that computer vision techniques that reduce the variability in the form of the image can be used to improve the generalizability of the ensemble based AI model. A comparison with the embryologist was also conducted. While no scores were provided directly by Alpha Fertility Centre, it was found that the conservative assumption that embryos are predicted to be likely viable (to avoid False Negatives) leads to a very similar accuracy to the true embryologist accuracy in the case of Study 1. Therefore, by making this assumption, the comparison between the ensemble based AI model accuracy and the embryologist accuracy can be carried out in the same way, as shown in Table 16. In this Study, a percentage improvement of 33.33% was found, similarly to the total improvement obtained from Study 1, 31.85%.

TABLE 16

Embryologist comparison. In this case where no embryologist scores were recorded, it is assumed that all embryos are conservatively predicted as likely viable, as a substitute measure. The expected embryologist accuracy is similar to those of the clinics in Study 1

| EmbryoScope validation dataset | Embryologist total | Percentage improvement | Model correct, embryologist incorrect | Model incorrect, embryologist correct |
| --- | --- | --- | --- | --- |
| Model accuracy | 30/62 = 48.39% | 33.33% | 23 | 13 |

Figure 19:
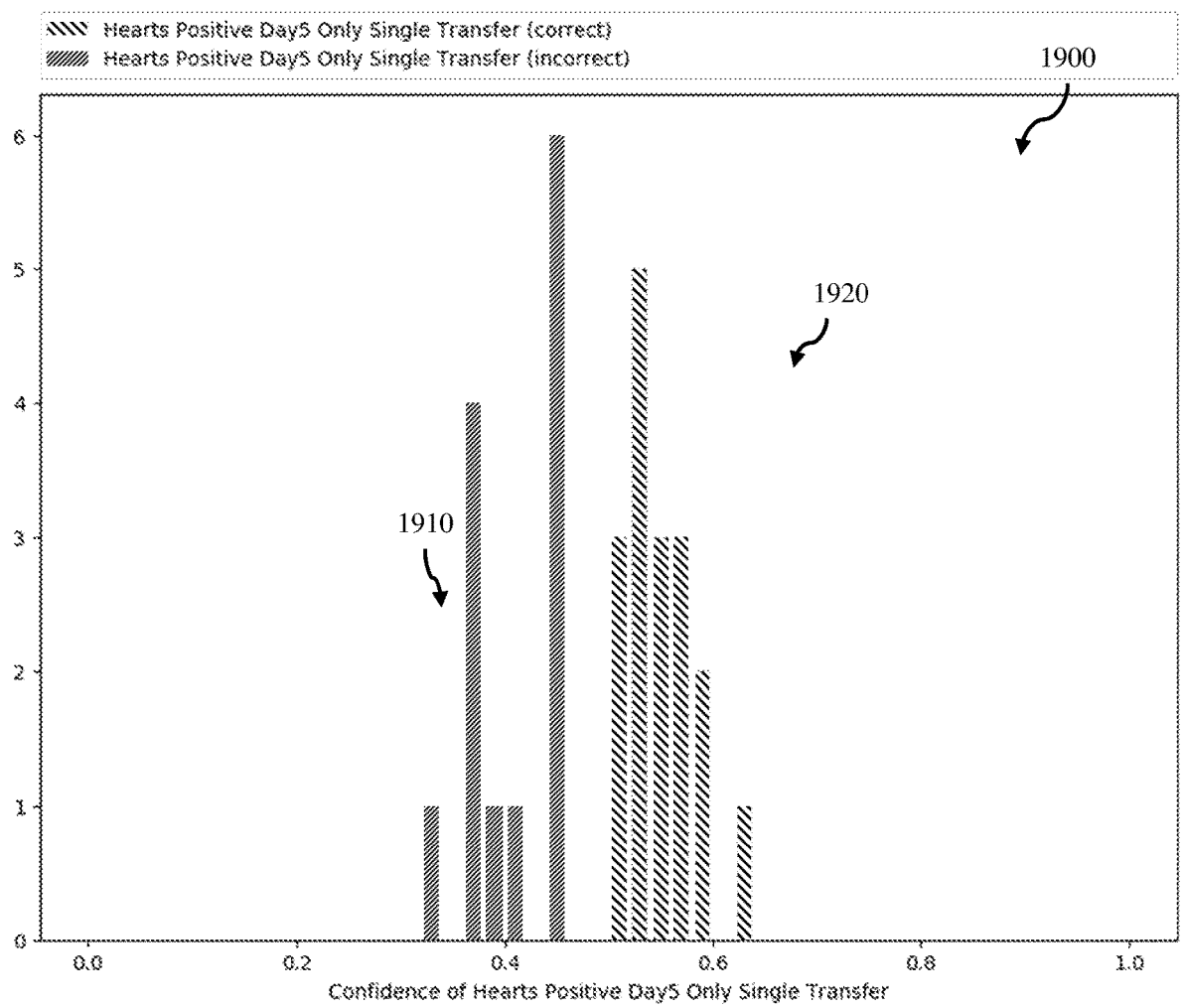
FIG. 19 is a plot of the distribution of inference scores for viable embryos (successful clinical pregnancy) using the ensemble model, when applied to the blind validation dataset of Study 3.
Figure 20:
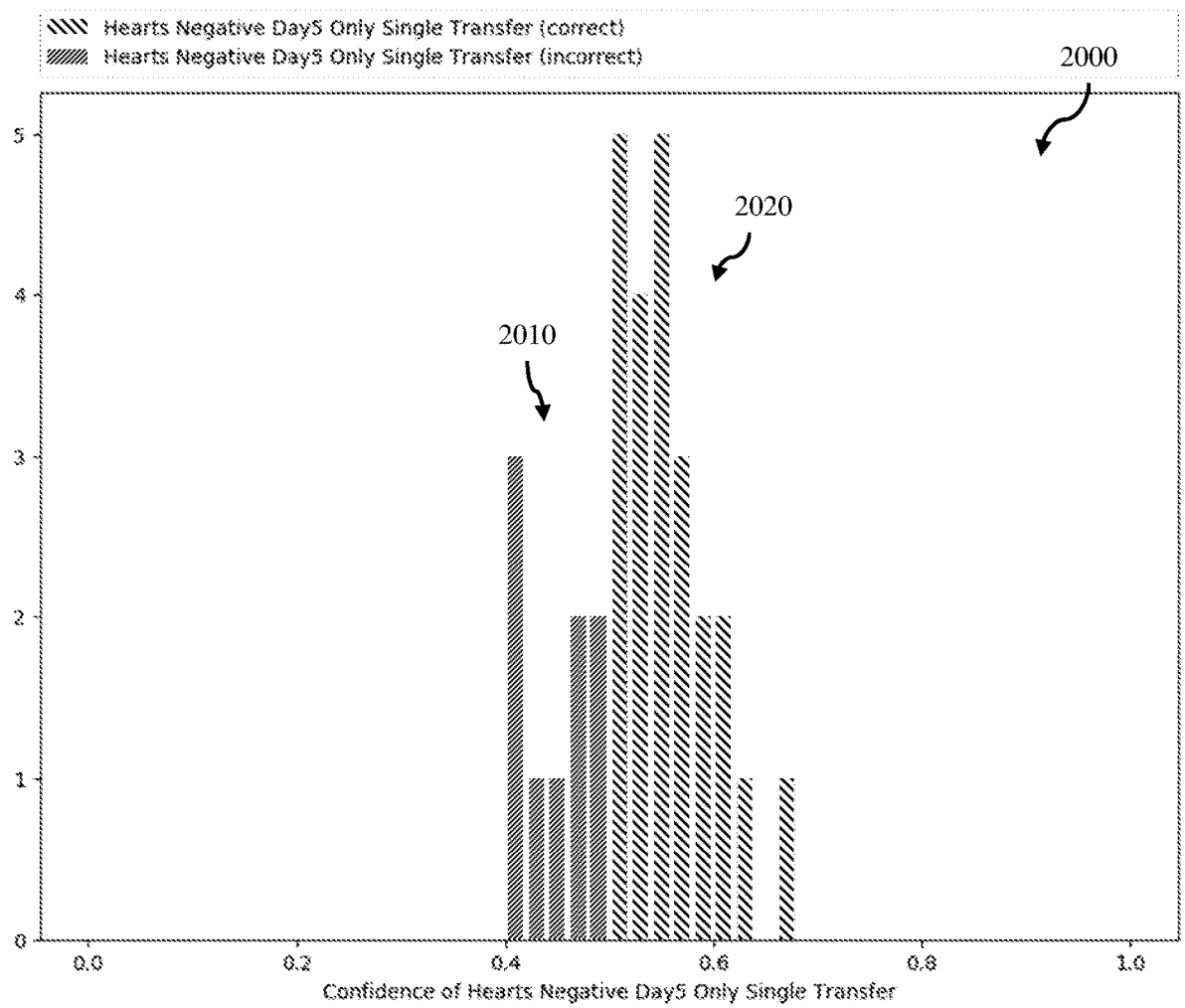
FIG. 20 is a plot of the distribution of inference scores for non-viable embryos (successful clinical pregnancy) using Ensemble model, when applied to the blind validation dataset of Study 3.

The distribution of inferences can also be obtained in this study, as shown in FIGS. 19 and 20. FIG. 19 is a plot of the distribution of inference scores for viable embryos (successful clinical pregnancy) using the ensemble based AI model 1900 (False Negatives 1910 boxes filled with thin upward diagonal lines; True Positives 1920 boxes filled with thick downward diagonal lines). FIG. 20 is a plot of the distribution of inference scores for non-viable embryos (successful clinical pregnancy) using the ensemble based AI model 2000 (False Negatives 1220 boxes filled with thin upward diagonal lines; True Positives 2020 boxes filled with thick downward diagonal lines). While the limited size of the study (62 images) does not allow the distribution to be very clear, it can nevertheless be observed that, in this case, the separation between the correct (1920; 2020) and incorrect predictions (1910; 2010) for both viable and non-viable embryos are much less distinct. This is to be expected for images that exhibit quite different additional features as artefacts from the EmbryoScope camera setup. These additional artefacts effectively add noise to the images, making it more difficult to extract the relevant features that indicate embryo health.

Furthermore, the accuracy in the viable category is significantly lower than the non-viable category, leading to a high rate of False Negatives. However, it was found that this effect was much reduced after even a preliminary computer vision treatment of the images, providing evidence for the improvement of handling images from different camera sources. In addition, it is expected that the addition of EmbryoScope images during a subsequent training or fine-tuning phase will also lead to improved performance.

SUMMARY

The efficacy of AI models including deep learning and computer vision models to predict the viability of embryos based on microscope images was explored in an Australian pilot study, and three cross-clinic studies to develop a general ensemble based AI model.

The pilot study involving a single Australian clinic was able to produce an overall accuracy of 67.7% in identifying embryo viability, with 74.1% accuracy for viable embryos and 65.3% accuracy for non-viable embryos. This improves upon the embryologists' classification rate by a factor of 30.8%. The success of these results prompted a more thorough cross-clinic study.

In 3 separate cross-clinic studies, a general AI selection model was developed, validated, and tested on a range of demographics from different clinics across the US, New Zealand and Malaysia. In Study 1, it was found that the ensemble based AI model is capable of achieving a high accuracy when compared to embryologists from each of the clinics, with a mean improvement of 31.85% in a cross-clinic blind validation study—similar to the improvement rate in the Australian pilot study. In addition, the distribution of the inference scores obtained from the ensemble based AI model exhibited a clear separation between the correct and incorrect predictions for both viable and non-viable embryos, which provides evidence that the model is translating correctly to future blind datasets.

A comparative study with embryologist scores was expanded to consider the effect of the order of the embryo rank. By transforming the ensemble based AI model inferences and the embryologist rank into an integer between 1 and 5, a direct comparison could be made as to how the ensemble based AI model will differ in ranking the embryos from most viable to least viable, compared to the embryologist. It was found that the ensemble based AI model again outperformed the embryologist, with 40.08% of the images being provided an improved ranking, whereas only 25.19% of the images were provided a worse ranking, 34.73% of the images unchanged in their ranking.

The ensemble based AI model was applied to a second blind validation set, which exhibited accuracy within a few percent of Study 1. The ability of the ensemble based AI model to perform on damaged or distorted images was also assessed. It was found that images that do not conform to the standard phase-contrast microscope images, or are low quality, blurred, compressed or poorly cropped are likely to be assessed as non-viable, and the ensemble based AI model confidence in the embryo image predicted is reduced.

In order to understand the issue of different camera hardware and how that affects the outcome of a study, a dataset of EmbryoScope images was obtained, and it was found that the ensemble based AI model when naively applied to this dataset does not reach the high accuracy achieved on the original set in Study 1. However, a preliminary data cleaning treatment of the images to handle artefacts and reduce noise systematically present in the EmbryoScope images markedly improved the results, bringing the accuracy of the ensemble based AI model much closer to its optimal value on Study 1. Because of the ability of the ensemble based AI model to be improved by incorporating larger and more diverse datasets into the training process, and thus fine-tuning the models so that it can self-improve over time, the 3 Studies in this document provide compelling evidence for the efficacy of AI models as important vital tools for the robust and consistent assessment of embryo viability in the near future.

Further, whilst the examples above use phase contrast images from light microscopes and EmbryoScope systems, further test has shown that the method may be used on images captured using a range of imaging systems. This testing has shown that the method is robust to a range of image sensors and images (i.e. beyond just embryoscopes and phase contrast images) including images extracted from video and time lapse systems. When using images extracted from video and time lapse system, a reference capture time point may be defined, and the image extracted from such systems may be the image closest in time to this reference capture time point, or the first image captured after the reference time. Quality assessment may be performed on images to ensure a selected image passes minimum quality criteria.

Embodiments of methods and systems for the computational generation of AI models configured to generate embryo viability score from an image using one or more deep learning models have been described. Given a new set of embryo images for training, a new AI model for estimating embryo viability can be generated by segmenting images to identify Zona Pellucida and IZC regions, which annotate the images into key morphological components. At least one Zona Deep Learning model is then trained on the Zona Pellucida masked images. In some embodiments a plurality of AI models including deep learning models and/or computer vision models are generated and models that exhibits stability, transferability from the validation set to the blind test set are selected and prediction accuracy are retained. These AI models may be combined for example using an ensemble model that selects models based on contrasting and diversity criterion, and which are combined using a confidence based voting strategy. Once a suitable AI model is trained, it can then be deployed to estimate viability of newly collected images. This can be provided as a cloud service allowing IVF clinics or embryologists to upload captured images and get a viability score to assist in deciding whether to implant an embryo, or where multiple embryo's are available, selecting which embryo (or embryo's) are most likely to be viable. Deployment may comprise exporting the model coefficients and model metadata to a file and then loading onto another computing system to process new images, or reconfiguring the computational system to receive new images and generate a viability estimate.

Implementations of ensemble based AI model include numerous choices, and embodiments described herein include several novel and advantageous features. Image preprocessing steps such as segmentation to identify Zona Pellucida and IZC regions, object detection, normalisation of images, cropping of images, image cleaning such as removal of old images or non-conforming images (e.g. containing artefacts) can be performed.

In relation to the deep learning models, the use of segmentation to identify the Zona Pellucida has a significant effect, with the final ensemble based AI model featuring four Zona models. Further deep learning models were generally found to outperform computer vision models, with the final model comprising of an ensemble of 8 deep learning AI models. However useful results can still be generated using a single AI model based on Zona images, or an ensemble (or similar) AI models comprising a combination of Deep Learning and CV models. The use of some deep learning models in which segmentation is performed prior to deep learning is thus preferred, and assists in producing contrasting deep learning models for use in the ensemble based AI model. Image augmentation was also found to improve robustness. Several architecture that performed well included ResNet-152, and DenseNet-161 (although other variants can be used). Similarly Stochastic Gradient Descent generally outperformed all other optimisation protocols for altering neuron weights in almost all trials (followed by Adam). The use of a custom loss function which modified the optimisation surface to make global minima more obvious improved robustness. Randomisation of the data sets before training, and in particular checking that the distribution of the dataset is even (or similar) across the test and training sets was also found to have a significant effect. Image of viable embryos are quite diverse, and thus checking the randomisation provides robustness against the diversity effects. Using a selection process to choose contrasting models (i.e. their results are independent as possible, and the scores are well distributed) for building the ensemble based AI model also improved performance. This can be assessed by examining the overlap in the set of viable images for two models. Prioritisation of the reduction of false negatives (i.e. data cleansing) also assists in improving the accuracy. As described herein, in the case of the embryo viability assessment model, models using images taken 5 days after in-vitro fertilisation outperformed models taken using earlier images (e.g. day 4 or before).

AI models using computer vision and deep learning methods can be generated using one or more of these advantageous features, and could be applied to other image sets besides embryos. With reference to FIG. 1, the embryo model 100 could be replaced with an alternative model, trained and used on other image data, whether of a medical nature or not. The methods could also be more generally for deep learning based models including ensemble based deep learning models. These could be trained and implemented using systems such as those illustrated in FIGS. 3A and 3B and described above.

Models trained as described herein can be usefully deployed to classify new images and thus assist embryologists in making implantation decisions, thus increasing success rates (ie pregnancies). Extensive testing of an embodiment of the ensemble based AI model was performed in which the ensemble based AI model was configured to generate an embryo viability score of an embryo from an image of the embryo taken five days after in-vitro fertilisation. The testing showed the model was able to clearly separate viable and non-viable embryos (see FIG. 13), and Tables 10 to 12 and FIGS. 14 to 16 illustrate that the model outperformed embryologist. In particular as illustrated in the above studies, an embodiment of an ensemble based AI model was found to have high accuracy in both identifying viable embryos (74.1%) and non-viable embryos (65.3%) and significantly outperform experienced embryologists in assessing viability of images by more than 30%.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software or instructions, middleware, platforms, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two, including cloud based systems. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, or other electronic units designed to perform the functions described herein, or a combination thereof. Various middleware and computing platforms may be used.

In some embodiments the processor module comprises one or more Central Processing Units (CPUs) or Graphical processing units (GPU) configured to perform some of the steps of the methods. Similarly a computing apparatus may comprise one or more CPUs and/or GPUs. A CPU may comprise an Input/Output Interface, an Arithmetic and Logic Unit (ALU) and a Control Unit and Program Counter element which is in communication with input and output devices through the Input/Output Interface. The Input/Output Interface may comprise a network interface and/or communications module for communicating with an equivalent communications module in another device using a predefined communications protocol (e.g. Bluetooth, Zigbee, IEEE 802.15, IEEE 802.11, TCP/IP, UDP, etc.). The computing apparatus may comprise a single CPU (core) or multiple CPU's (multiple core), or multiple processors. The computing apparatus is typically a cloud based computing apparatus using GPU clusters, but may be a parallel processor, a vector processor, or be a distributed computing device. Memory is operatively coupled to the processor(s) and may comprise RAM and ROM components, and may be provided within or external to the device or processor module. The memory may be used to store an operating system and additional software modules or instructions. The processor (s) may be configured to load and executed the software modules or instructions stored in the memory.

Software modules, also known as computer programs, computer codes, or instructions, may contain a number a number of source code or object code segments or instructions, and may reside in any computer readable medium such as a RAM memory, flash memory, ROM memory, EPROM memory, registers, hard disk, a removable disk, a CD-ROM, a DVD-ROM, a Blu-ray disc, or any other form of computer readable medium. In some aspects the computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media. In another aspect, the computer readable medium may be integral to the processor. The processor and the computer readable medium may reside in an ASIC or related device. The software codes may be stored in a memory unit and the processor may be configured to execute them. The memory unit may be implemented within the processor or external to the processor, in which case it can be communicatively coupled to the processor via various means as is known in the art.

Further, it should be appreciated that modules and/or other appropriate means for performing the methods and techniques described herein can be downloaded and/or otherwise obtained by computing device. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a computing device can obtain the various methods upon coupling or providing the storage means to the device. Moreover, any other suitable technique for providing the methods and techniques described herein to a device can be utilized.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgment of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

The invention claimed is:

1. A method for computationally generating an Artificial Intelligence (AI) model configured to estimate an embryo viability score from an image, the method comprising:
   receiving a plurality of images and associated metadata, wherein each image is captured during a pre-determined time window after In-Vitro Fertilization (IVF) and the pre-determined time window is 24 hours or less, and the metadata associated with the image comprises at least a pregnancy outcome label;
   pre-processing each image comprising at least segmenting the image to identify a Zona Pellucida region;
   generating an Artificial Intelligence (AI) model configured to generate an embryo viability score from an input image by:
      training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model; and
      training one or more additional AI models wherein each additional AI model is either a computer vision model trained using a machine learning method that uses a combination of one or more computer vision descriptors extracted from an image to estimate an embryo viability score, a deep learning model trained on images localized to the embryo comprising both Zona Pellucida and IntraZonal Cavity (IZC) regions, and a deep learning model trained on a set of IntraZonal Cavity (IZC) images in which all regions apart from the IZC are masked, and either using an ensemble method to combine at least two of the at least one Zona deep learning model and the one or more additional AI models to generate the AI model embryo viability score from an input image or using a distillation method to train an AI model to generate the AI model embryo viability score using the at least one Zona deep learning model and the one or more additional AI models to generate the AI model; and
   deploying the AI model.

2. The method of claim 1, wherein the set of Zona Pellucida images comprising images in which regions bounded by the Zona Pellucida region are masked.

3. The method of claim 1, wherein the AI model is generated using an ensemble model comprising selecting at least two contrasting AI models from the at least one Zona deep learning model and the one or more additional AI models, and selection of AI models is performed to generate a set of contrasting AI models and applying a voting strategy to the at least two contrasting AI models that defines how the selected at least two contrasting AI models are combined to generate an outcome score for an image.

4. The method of claim 1, wherein selecting at least two contrasting AI models comprises:
   generating a distribution of embryo viability scores from a set of images for each of the at least one Zona deep learning model and the one or more additional AI models; and
   comparing the distributions and discarding a model if the associated distributions is too similar to another distribution to select AI models with contrasting distributions.

5. The method of claim 1, wherein the pre-determined time window is a 24 hour timer period beginning 5 days after fertilization.

6. The method of claim 1, wherein the pregnancy outcome label is a ground-truth pregnancy outcome measurement performed within 12 weeks after embryo transfer.

7. The method of claim 6, wherein the ground-truth pregnancy outcome measurement is whether a fetal heartbeat is detected.

8. The method of claim 1, further comprising cleaning the plurality of image comprising identifying images with likely incorrect pregnancy outcome labels, and excluding or re-labelling the identified images.

9. The method of claim 1, wherein each AI model generates an outcome score wherein the outcome is a n-ary outcome having n states, and training an AI model comprises a plurality of training-validation cycles further comprises randomly allocating the plurality of images to one of a training set, a validation set or a blind validation set, such that the training dataset comprises at least 60% of the images, the validation dataset comprises at least 10% of the images, and the blind validation dataset comprises at least 10% of the images, and after allocating the images to the training set, validation set and blind validation set, calculating the frequency of each of the n-ary outcome states in each of the training set, validation set and blind validation set, and testing that the frequencies are similar, and if the frequencies are not similar then discarding the allocation and repeating the randomization until a randomization is obtained in which the frequencies are similar.

10. The method of claim 1, wherein training a computer vision model comprising performing a plurality of a training-validation cycles, and during each cycle the images are clustered based on the computer vision descriptors using an unsupervised clustering algorithm to generate a set of clusters, and each image is assigned to a cluster using a distance measure based on the values of the computer vision descriptors of the image, and a supervised learning method is use to determine whether a particular combination of these features corresponds to an outcome measure, and frequency information of the presence of each computer vision descriptor in the plurality of images.

11. The method of claim 1, wherein the deep learning method uses a loss function configured to modify an optimization protocol is to emphasize global minima.

12. The method of claim 11, wherein the loss function includes a residual term defined in terms of the network weights, which encodes the collective difference in the predicted value from the model and the target outcome for each image, and includes it as an additional contribution to the normal cross entropy loss function.

13. The method of claim 1, wherein the method is performed on a cloud based computing system using a webserver, a database, and a plurality of training servers, wherein the webserver receives one or more model training parameters from a user, and the webserver initiates a training process on one or more of the plurality of training servers, comprising uploading training code to one of the plurality the training server, and the training server requests the plurality of images and associated metadata from a data repository, and performs the steps of preparing each image, generating a plurality of computer vision models and generating a plurality of deep learning models, and each training server is configured to periodically save the models to a storage service, and accuracy information to one or more log files to allow a training process to be restarted.

14. The method of claim 1, wherein the ensemble model is trained to bias residual inaccuracies to minimize false negatives.

15. The method of claim 1, wherein each image is a phase contrast image.

16. A method for computationally generating an embryo viability score from an image, the method comprising:
generating, in a computational system, an Artificial Intelligence (AI) model configured to generate an embryo viability score from an image according to the method comprising:
receiving a plurality of images and associated metadata, wherein each image is captured during a pre-determined time window after In-Vitro Fertilization (IVF) and the pre-determined time window is 24 hours or less, and the metadata associated with the image comprises at least a pregnancy outcome label;
pre-processing each image comprising at least segmenting the image to identify a Zona Pellucida region; and
generating the Artificial Intelligence (AI) model which is configured to generate an embryo viability score from an input image by:
training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model; and
training one or more additional AI models wherein each additional AI model is either a computer vision model trained using a machine learning method that uses a combination of one or more computer vision descriptors extracted from an image to estimate an embryo viability score, a deep learning model trained on images localized to the embryo comprising both Zona Pellucida and IntraZonal Cavity (IZC) regions, and a deep learning model trained on a set of IntraZonal Cavity (IZC) images in which all regions apart from the IZC are masked, and either using an ensemble method to combine at least two of the at least one Zona deep learning model and the one or more additional AI models to generate the AI model embryo viability score from an input image or using a distillation method to train an AI model to generate the AI model embryo viability score using the at least one Zona deep learning model and the one or more additional AI models to generate the AI model;
receiving, from a user via a user interface of the computational system, an image captured during a pre-determined time window after In-Vitro Fertilization (IVF);
pre-processing the image according to the pre-processing steps used to generate the AI model;
providing the pre-processed image to the AI model to obtain an estimate of the embryo viability score; and
sending the embryo viability score to the user via the user interface.

17. A method for obtaining an embryo viability score from an image, comprising:
uploading, via a user interface, an image captured during a pre-determined time window after In-Vitro Fertilization (IVF) to a cloud based Artificial Intelligence (AI) model configured to generate an embryo viability score from an image wherein the AI model is generated according to the method comprising:
receiving a plurality of images and associated metadata, wherein each image is captured during a pre-determined time window after In-Vitro Fertilization (IVF) and the pre- determined time window is 24 hours or less, and the metadata associated with the image comprises at least a pregnancy outcome label;
pre-processing each image comprising at least segmenting the image to identify a Zona Pellucida region; and
generating the Artificial Intelligence (AI) model which is configured to generate an embryo viability score from an input image by:
training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model; and
training one or more additional AI models wherein each additional AI model is either a computer vision model trained using a machine learning method that uses a combination of one or more computer vision descriptors extracted from an image to estimate an embryo viability score, a deep learning model trained on images localized to the embryo comprising both Zona Pellucida and IntraZonal Cavity (IZC) regions, and a deep learning model trained on a set of IntraZonal Cavity (IZC) images in which all regions apart from the IZC are masked, and either using an ensemble method to combine at least two of the at least one Zona deep learning model and the one or more additional AI models to generate the AI model embryo viability score from an input image or using a distillation method to train an AI model to generate the AI model embryo viability score using the at least one Zona deep learning model and the one or more additional AI models to generate the AI model;
receiving an embryo viability score from the cloud based AI model via the user interface.

18. A cloud based computational system comprising one or more computing apparatus, comprising one or more processors and one or more memories, configured to computationally generate an Artificial Intelligence (AI) model configured to estimate an embryo viability score from an image according to the method comprising:
receiving a plurality of images and associated metadata, wherein each image is captured during a pre-determined time window after In-Vitro Fertilization (IVF) and the pre-determined time window is 24 hours or less, and the metadata associated with the image comprises at least a pregnancy outcome label;
pre-processing each image comprising at least segmenting the image to identify a Zona Pellucida region; and
generating the Artificial Intelligence (AI) model which is configured to generate an embryo viability score from an input image by:
training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model; and
training one or more additional AI models wherein each additional AI model is either a computer vision model trained using a machine learning method that uses a combination of one or more computer vision descriptors extracted from an image to estimate an embryo viability score, a deep learning model trained on images localized to the embryo comprising both Zona Pellucida and IntraZonal Cavity (IZC) regions, and a deep learning model trained on a set of IntraZonal Cavity (IZC) images in which all regions apart from the IZC are masked, and either using an ensemble method to combine at least two of the at least one Zona deep learning model and the one or more additional AI models to generate the AI model embryo viability score from an input image or using a distillation method to train an AI model to generate the AI model embryo viability score using the at least one Zona deep learning model and the one or more additional AI models to generate the AI model.

19. A cloud based computational system comprising one or more computing apparatus, comprising one or more processors and one or more memories, configured to computationally generate an embryo viability score from an image, wherein the computational system comprises:
an Artificial Intelligence (AI) model deployed to the cloud based computational system and configured to generate an embryo viability score from an image wherein the AI model is generated according to the method comprising:
receiving a plurality of images and associated metadata, wherein each image is captured during a pre-determined time window after In-Vitro Fertilization (IVF) and the pre-determined time window is 24 hours or less, and the metadata associated with the image comprises at least a pregnancy outcome label;
pre-processing each image comprising at least segmenting the image to identify a Zona Pellucida region; and
generating the Artificial Intelligence (AI) model which is configured to generate an embryo viability score from an input image by:
training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model;
training one or more additional AI models wherein each additional AI model is either a computer vision model trained using a machine learning method that uses a combination of one or more computer vision descriptors extracted from an image to estimate an embryo viability score, a deep learning model trained on images localized to the embryo comprising both Zona Pellucida and IntraZonal Cavity (IZC) regions, and a deep learning model trained on a set of IntraZonal Cavity (IZC) images in which all regions apart from the IZC are masked, and either using an ensemble method to combine at least two of the at least one Zona deep learning model and the one or more additional AI models to generate the AI model embryo viability score from an input image or using a distillation method to train an AI model to generate the AI model embryo viability score using the at least one Zona deep learning model and the one or more additional AI models to generate the AI model;
a user interface configured to:
receive, from a user, an image captured during a pre-determined time window after In-Vitro Fertilization (IVF);
provide the image to the AI model to obtain an embryo viability score; and
send the embryo viability score to the user via the user interface.

20. A computational system configured to generate an embryo viability score from an image, wherein the computational system comprises at least one processor, and at least one memory comprising instructions to configure the at least one processor to:
receive an image captured during a pre-determined time window after In-Vitro Fertilization (IVF)
upload, via a user interface, the image captured during a pre-determined time window after In-Vitro Fertilization (IVF) to an Artificial Intelligence (AI) model deployed on a cloud based computational system configured to generate an embryo viability score from an image wherein the AI model is generated according to the method comprising:
receiving a plurality of images and associated metadata, wherein each image is captured during a pre-determined time window after In-Vitro Fertilization (IVF) and the pre-determined time window is 24 hours or less, and the metadata associated with the image comprises at least a pregnancy outcome label;
pre-processing each image comprising at least segmenting the image to identify a Zona Pellucida region; and
generating the Artificial Intelligence (AI) model which is configured to generate an embryo viability score from an input image by:
training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model;
training one or more additional AI models wherein each additional AI model is either a computer vision model trained using a machine learning method that uses a combination of one or more computer vision descriptors extracted from an image to estimate an embryo viability score, a deep learning model trained on images localized to the embryo comprising both Zona Pellucida and IntraZonal Cavity (IZC) regions, and a deep learning model trained on a set of IntraZonal Cavity (IZC) images in which all regions apart from the IZC are masked, and either using an ensemble method to combine at least two of the at least one Zona deep learning model and the one or more additional AI models to generate the AI model embryo viability score from an input image or using a distillation method to train an AI model to generate the AI model embryo viability score using the at least one Zona deep learning model and the one or more additional AI models to generate the AI model;

receive an embryo viability score from the cloud based AI model; and display the embryo viability score via the user interface.

21. A method for computationally generating an Artificial Intelligence (AI) model configured to estimate an embryo viability score from an image, the method comprising:

receiving a plurality of images and associated metadata, wherein each image is captured during a pre-determined time window after In-Vitro Fertilization (IVF) and the pre-determined time window is 24 hours or less, and the metadata associated with the image comprises at least a pregnancy outcome label;

pre-processing each image comprising at least segmenting the image to identify a Zona Pellucida region;

generating an Artificial Intelligence (AI) model configured to generate an embryo viability score from an input image by training at least one Zona Deep Learning Model using a deep learning method, comprising training a deep learning model on a set of Zona Pellucida images in which the Zona Pellucida regions are identified, and the associated pregnancy outcome labels are at least used to assess the accuracy of a trained model; and deploying the AI model, wherein the deep learning method uses a loss function configured to modify an optimization protocol to emphasize global minima, and wherein the loss function includes a residual term defined in terms of the network weights, which encodes the collective difference in the predicted value from the model and the target outcome for each image, and includes it as an additional contribution to the normal cross entropy loss function.

* * * * *